(12) United States Patent
Zhang

(10) Patent No.: US 9,717,733 B2
(45) Date of Patent: Aug. 1, 2017

(54) EDIBLE PLANT-DERIVED MICROVESICLE COMPOSITIONS INCLUDING CONJUGATED THERAPEUTIC AGENTS AND METHODS FOR USING THE SAME

(71) Applicant: University of Louisville Research Foundation, Inc., Louisville, KY (US)

(72) Inventor: Huang-Ge Zhang, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/825,957

(22) Filed: Aug. 13, 2015

(65) Prior Publication Data

US 2016/0045448 A1 Feb. 18, 2016

Related U.S. Application Data

(60) Provisional application No. 62/036,850, filed on Aug. 13, 2014.

(51) Int. Cl.
| | | |
|---|---|---|
| *A61K 31/12* | (2006.01) | |
| *A61K 31/519* | (2006.01) | |
| *A61K 9/51* | (2006.01) | |
| *A61K 36/752* | (2006.01) | |
| *A61K 36/81* | (2006.01) | |
| *A61K 36/87* | (2006.01) | |
| *A61K 36/23* | (2006.01) | |
| *A61K 36/28* | (2006.01) | |
| *A61K 36/31* | (2006.01) | |

(52) U.S. Cl.
CPC .......... *A61K 31/519* (2013.01); *A61K 9/5176* (2013.01); *A61K 36/23* (2013.01); *A61K 36/28* (2013.01); *A61K 36/31* (2013.01); *A61K 36/752* (2013.01); *A61K 36/81* (2013.01); *A61K 36/87* (2013.01)

(58) Field of Classification Search
USPC ....................................... 514/679, 249, 449
See application file for complete search history.

(56) References Cited

U.S. PATENT DOCUMENTS 7,396,546 B2 * 7/2008 Rosenbloom ........ A61K 36/185
424/440

OTHER PUBLICATIONS

Sun et al., Molecular Therapy, 2010, 18(9): 1606-1614.*
Powell, JJ, Faria, N, Thomas-Mckay, E, and Pele, LC (2010). Origin and fate of dietary nanoparticles and microparticles in the gastro-intestinal tract. J Autoimmun 34: J226-233.
Powell, JJ, Thoree, V, and Pele, LC (2007). Dietary microparticles and their impact on tolerance and immune responsiveness of the gastrointestinal tract. Br J Nutr 98 Suppl 1: S59-63.
Schneider, JC (2007). Can microparticles contribute to inflammatory bowel disease: innocuous or inflammatory? Exp Biol Med (Maywood) 232: 1-2.
Badens, E, Magnan, C, and Charbit, G (2001). Microparticles of soy lecithin formed by supercritical processes. Biotechnology and Bioengineering 72: 194-204.
Bauer, C, et al. (2010). Colitis induced in mice with dextran sulfate sodium (DSS) is mediated by the NLRP3 Inflammasome. Gut 59: 1192-1199.
Wang, Q, et al. (2013). Delivery of therapeutic agents by nanoparticles made of grapefruit-derived lipids. Nat Commun 4.
Ju, S, et al. (2013). Grape Exosome-like Nanoparticles Induce Intestinal Stem Cells and Protect Mice From DSS-Induced Colitis. Mol Ther 21: 1345-1357.
Sho, JY, Chi, S-G, and Chun, HS (2011). Oral administration of docosahexaenoic acid attenuates colitis induced by dextran sulfate sodium in mice. Molecular Nutrition & Food Research 55: 239-246.
Stremmel, W, Merle, U, Zahn, A, Autschbach, F, Hinz, U, and Ehehalt, R (2005). Retarded release phosphatidylcholine benefits patients with chronic active ulcerative colitis. Gut 54: 966-971.
Dou, W, et al. (2013). Protective effect of naringenin against experimental colitis via suppression of Toll-like receptor 4/NF-κb signalling. British Journal of Nutrition FirstView: 1-10.
Yan, F, et al (2011). Colon-specific delivery of a probiotic-derived soluble protein ameliorates intestinal inflammation in mice through an EGFR-dependent mechanism. The Journal of Clinical Investigation 121: 2242-2253.
Liu, C, et al. (2006). Murine Mammary Carcinoma Exosomes Promote Tumor Growth by Suppression of NK Cell Function. The Journal of Immunology 176: 1375-1385.
Laulagnier, K, et al. (2004). Mast cell- and dendritic cell-derived exosomes display a specific lipid composition and an unusual membrane organization. Biochem J 380: 161-171.
Morteau, O, et al. (2000). Impaired mucosal defense to acute colonic injury in mice lacking cyclooxygenase-1 or cyclooxygenase-2. The Journal of Clinical Investigation 105: 469-478.
Conner, SD, and Schmid, SL (2003). Regulated portals of entry into the cell. Nature 422: 37-44.
Ghigo, E, et al. (2008). Ameobal Pathogen Mimivirus Infects Macrophages through Phagocytosis. PLoS Pathog 4: e1000087.
Pollock, S, et al. (2010). Uptake and trafficking of liposomes to the endoplasmic reticulum. The FASEB Journal 24: 1866-1878.
Lee, T-S, and Chau, L-Y (2002). Heme oxygenase-1 mediates the anti-inflammatory effect of interleukin-10 in mice. Nat Med 8: 240-246.

(Continued)

*Primary Examiner* — Rei-Tsang Shiao
(74) *Attorney, Agent, or Firm* — Stites & Harbison, PLLC; Terry L. Wright

(57) ABSTRACT

A composition is provided that includes a microvesicle derived from an edible plant and a therapeutic agent conjugated to the microvesicle. The therapeutic agent can be chemically-linked to a plasma membrane of the microvesicle with a cross-linking agent and the edible plant can be a fruit or a vegetable. Methods for treating an inflammatory disorder or a cancer are further provided and include administering to a subject in need thereof an effective amount of a composition including a microvesicle derived from an edible plant and having a therapeutic agent conjugated to the microvesicle.

14 Claims, 43 Drawing Sheets

(56) References Cited

OTHER PUBLICATIONS

Sheikh, SZ, et al. (2011). An Anti-Inflammatory Role for Carbon Monoxide and Heme Oxygenase-1 in Chronic Th2-Mediated Murine Colitis. The Journal of Immunology 186: 5506-5513.
Majumdar, S, and Aggarwal, BB (2001). Methotrexate Suppresses NF-κb Activation Through Inhibition of IκBα Phosphorylation and Degradation. The Journal of Immunology 167: 2911-2920.
Desai, N (2012). Challenges in Development of Nanoparticle-Based Therapeutics. AAPS J 14: 282-295.
Pabst, O, and Mowat, AM (2012). Oral tolerance to food protein. Mucosal Immunol 5: 232-239.
Yamanaka, YJ, and Leong, KW (2008). Engineering strategies to enhance nanoparticle-mediated oral delivery. Journal of Biomaterials Science—Polymer Edition 19: 1549-1570.
Wilson, DS, Dalmasso, G, Wang, L, Sitaraman, SV, Merlin, D, and Murthy, N (2010). Orally delivered thioketal nanoparticles loaded with TNF-α-siRNA target inflammation and inhibit gene expression in the intestines. Nat Mater 9: 923-928.
Friend, DR (2005). New oral delivery systems for treatment of inflammatory bowel disease. Advanced Drug Delivery Reviews 57: 247-265.
Jourdan, PS, McIntosh CA, and Mansell, RL (1985). Naringin Levels in Citrus Tissues : II. Quantitative Distribution of Naringin in Citrus paradisi MacFad. Plant Physiol 77: 903-908.
Newberry, RD, Stenson, WF, and Lorenz, RG (1999). Cyclooxygenase-2-dependent arachidonic acid metabolites are essential modulators of the intestinal immune response to dietary antigen. Nat Med 5: 900-906.
Newberry, RD, McDonough, JS, Stenson, WF, and Lorenz, RG (2001). Spontaneous and Continuous Cyclooxygenase-2-Dependent Prostaglandin E2 Production by Stromal Cells in the Murine Small Intestine Lamina Propria: Directing the Tone of the Intestinal Immune Response. The Journal of Immunology 166: 4465-4472.
Tai, H-H, Ensor, CM, Tong, M, Zhou, H, and Yan, F (2002). Prostaglandin catabolizing enzymes. Prostaglandins & Other Lipid Mediators 68-69: 483-493.
Sun, D, et al (2010). A Novel Nanoparticle Drug Delivery System: The Anti-inflammatory Activity of Curcumin Is Enhanced When Encapsulated in Exosomes. Mol Ther 18: 1606-1614.
Deng, ZB, et al. (2012). Intestinal mucus-derived nanoparticles mediate activation of Wnt/beta-catenin signaling plays a role in induction of liver NKT cell anergy. Hepatology.
Wanjie, SW, Welti, R, Moreau, RA, and Chapman, KD (2005). Identification and quantification of glycerolipids in cotton fibers: reconciliation with metabolic pathway predictions from DNA databases. Lipids 40: 773-785.
Majoros, IJ, Thomas, TP, Menta, CB, and Baker, JR (2005). Poly(amidoamine) Dendrimer-Based Multifunctional Engineered Nanodevice for Cancer Therapy. Journal of Medicinal Chemistry 48: 5892-5899.
Vaishnava, S, et al. (2011). The Antibacterial Lectin RegIIIγ Promotes the Spatial Segregation of Microbiota and Host in the Intestine. Science 334: 255-258.
Katz, JP, et al. (2002). The zinc-finger transcription factor Klf4 is required for terminal differentiation of goblet cells in the colon. Development 129: 2619-2628.
Fuhrer, A, Sprenger, N, Kurakevich, E, Borsig, L, Chassard, C, and Hennet, T (2010). Milk sialyllactose influences colitis in mice through selective intestinal bacterial colonization. The Journal of Experimental Medicine 207: 2843-2854.
Denning, TL, Wang, Y-C, Patel, SR, Williams, IR, and Pulendran, B (2007). Lamina propria macrophages and dendritic cells differentially induce regulatory and interleukin 17-producing T cell responses. Nat Immunol 8: 1086-1094.
Ismail, AS, et al. (2011). γδ intraepithelial lymphocytes are essential mediators of host—microbial homeostasis at the intestinal mucosal surface. Proceedings of the National Academy of Sciences 108: 8743-8748.
Wang, Y, et al. (2010). Lymphotoxin Beta Receptor Signaling in Intestinal Epithelial Cells Orchestrates Innate Immune Responses against Mucosal Bacterial Infection. Immunity 32: 403-413.
Allen, IC, et al. (2010). The NLRP3 inflammasome functions as a negative regulator of tumorigenesis during colitis-associated cancer. The Journal of Experimental Medicine 207: 1045-1056.
Riehl, TE, et al. (2006). Azoxymethane protects intestinal stem cells and reduces crypt epithelial mitosis through a COX-1-dependent mechanism. American Journal of Physiology—Gastrointestinal and Liver Physiology 291: G1062-G1070.
Kamada, N, et al. (2005). Abnormally Differentiated Subsets of Intestinal Macrophage Play a Key Role in Th1-Dominant Chronic Colitis through Excess Production of IL-12 and IL-23 in Response to Bacteria. The Journal of Immunology 175: 6900-6908.
Xiang, X, et al., Induction of myeloid-derived suppressor cells by tumor exosomes. International journal of cancer. Journal international du cancer 124, 2621-2633 (2009).
Wang B, et al. (2014). Targeted drug delivery to intestinal macrophages by bioactive nanovesicles released from grapefruit. Mol Ther. 22(3):522-34.

* cited by examiner

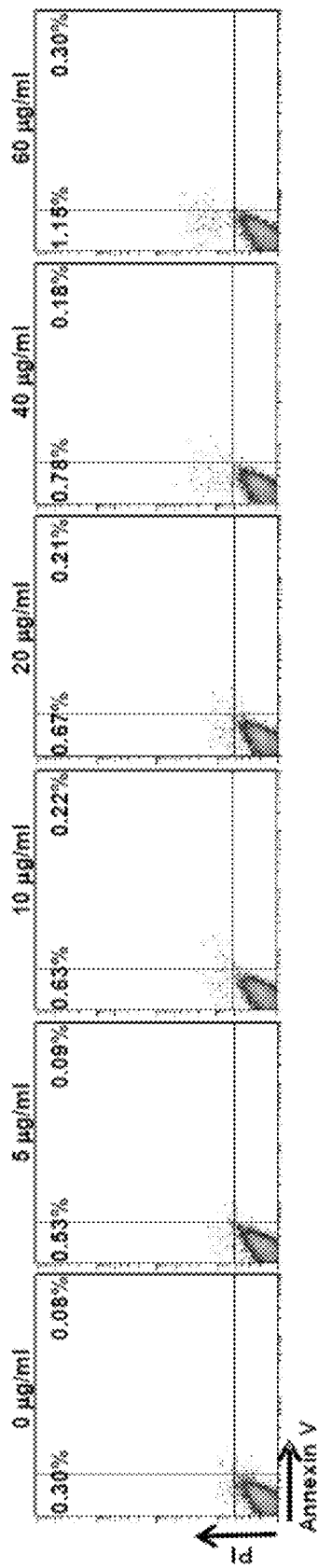
FIG. 12
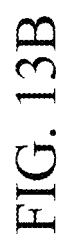
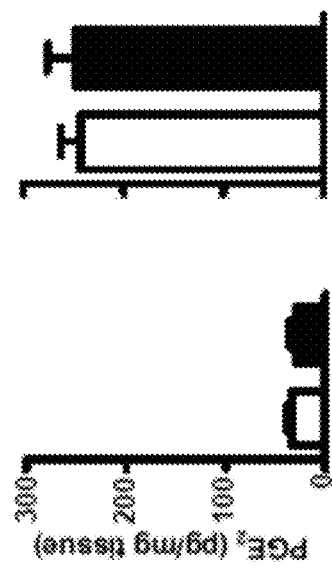
FIG. 13A　　FIG. 13B

US 9,717,733 B2

1

EDIBLE PLANT-DERIVED MICROVESICLE COMPOSITIONS INCLUDING CONJUGATED THERAPEUTIC AGENTS AND METHODS FOR USING THE SAME

RELATED APPLICATIONS

This application claims priority from U.S. Provisional Application Ser. No. 62/036,850, filed Aug. 13, 2014, the entire disclosure of which is incorporated herein by this reference.

TECHNICAL FIELD

The presently-disclosed subject matter relates to edible plant-derived microvesicle compositions and methods of using the same for the diagnosis and treatment of disease. In particular, the presently-disclosed subject matter relates to compositions that include edible plant-derived microvesicles including one or more therapeutic agents conjugated directly to the microvesicles and that are useful in the diagnosis and treatment of disease.

BACKGROUND

The gut immune system plays an important role in preventing inflammation induced by food derived antigens. However, the role the immune system plays in ensuring that plant based materials are modified to be beneficial as opposed to being perceived as antigens is not clear. Numerous naturally occurring nanoparticles exist in our diet and are absorbed through the intestine daily. How they influence our mucosal and systemic immune system though is poorly understood.

Inflammatory bowel diseases (IBD), including Crohn's disease (CD) and ulcerative colitis (UC), are chronic, relapsing inflammatory disorders of the gastrointestinal tract. Intestinal macrophages are important in maintaining mucosal tolerance and suppressing inflammation to maintain the host's steady-state. However, under pathophysiological conditions, such as IBD, intestinal macrophages lose their tolerogenic properties which results in uncontrolled intestinal inflammation. Thus, manipulating the function of intestinal macrophages is considered an important strategy in the treatment of IBD patients. Conventional therapies for IBD are steroidal drugs and immunosuppressants. Yet, these therapies generally fail to produce satisfactory results due to their lack of specific targeting and their toxicity to normal cells. Therefore, development of a new or an alternative delivery system to locate immunosuppressants selectively to intestinal inflammatory cells is essential for patients with IBD.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this Summary does not list or suggest all possible combinations of such features.

The presently-disclosed subject matter includes edible plant-derived microvesicle compositions and methods of using the same for the diagnosis and treatment of disease. In some embodiments, a composition is provided that comprises a microvesicle derived from an edible plant; and a therapeutic agent conjugated to the microvesicle. In some embodiments, to conjugate the therapeutic agent to the microvesicle, the therapeutic agent is chemically-linked to a plasma membrane of the microvesicle with a cross-linking agent. In some embodiments, such a cross-linking agent is selected from the group consisting of N-ethylcarbodiimide (EDC), dicyclohexyl carbodiimide (DCC), homobifunctional disuccinimidyl, disuccinimidyl tartrate, 3-3'-dithiobispropionimidate (DTBP), and ethylene glycol bis-succinimidyl succinate (EGS).

With respect to the edible plants used to produce the microvesicles of the presently-disclosed subject matter, in some embodiments, the edible plant is a fruit or a vegetable. For instance, in some embodiments, the fruit or vegetable used to produce the microvesicles is selected from a grape, a grapefruit, a tomato, a ginger, a carrot, a broccoli, a cabbage, a lettuce, a blackberry, a cauliflower, and a spinach.

Numerous therapeutic agents can be conjugated to the edible plant-derived microvesicles of the presently-disclosed subject matter. In some embodiments, the therapeutic agent is selected from a phytochemical agent and a chemotherapeutic agent. For example, in some embodiments, the therapeutic agent is a phytochemical agent, such as, in certain embodiments, curcumin, resveratrol, baicalein, equol, fisetin, and quercetin. As another example, in some embodiments, the therapeutic agent is a chemotherapeutic agent, such as, in certain embodiments, retinoic acid, 5-fluorouracil, vincristine, actinomycin D, adriamycin, cisplatin, docetaxel, doxorubicin, and taxol.

In other embodiments, the therapeutic agent conjugated to the edible plant-derived microvesicles of the presently-disclosed subject matter comprises a nucleic acid molecule selected from an siRNA, a microRNA, and a mammalian expression vector. In some embodiments, the therapeutic agent comprises an anti-inflammatory agent, such as, in some embodiments, methotrexate. Each of the edible plant-derived compositions can also, in some embodiments, be further provided as a pharmaceutical composition where the edible plant-derived compositions are combined with a pharmaceutically-acceptable vehicle, carrier, or excipient.

Still further provided, in some embodiments of the presently-disclosed subject matter, are methods for treating an inflammatory disorder or a cancer. In some embodiments, a method for treating an inflammatory disorder is provided that comprises administering to a subject in need thereof an effective amount of an edible plant-derived microvesicle composition as described herein. In some embodiments, the inflammatory disorder is selected from the group consisting of sepsis, septic shock, colitis, inflammation-promoted cancer, and arthritis. In some particular embodiments, the inflammatory disorder is inflammation-promoted cancer, and the inflammation-promoted cancer is colon cancer. In other particular embodiments, the inflammatory disorder is colitis.

For administration of an edible plant-derived microvesicle composition described herein, in some embodiments, the composition is administered orally or intranasally to thereby treat the inflammatory disorder. In some embodiments, administering the composition reduces an amount of an inflammatory cytokine in a subject, including, in some embodiments, a reduction in an amount of tumor necrosis factor-α, interleukin-1β, and/or interleukin-6.

Further features and advantages of the present invention will become evident to those of ordinary skill in the art after a study of the description, figures, and non-limiting examples in this document.

BRIEF DESCRIPTION OF THE DRAWINGS

FIG. 12 is a graph showing the cytotoxicity effect of GDNs on RAW264.7 mouse macrophages after 24 h incubation, where RAW264.7 cells were incubated with indicated concentrations of GDNs for 24 h and then stained with Annexin-V/PI to detect the mode of cell death, and where Annexin V$^+$ alone indicates early apoptosis and PI$^+$ alone represents necrosis, with cells at the final stage of apoptosis taking up both stains.

FIGS. 13A-13B include graphs showing PGE$_2$ production in colonic mucosa during both steady-state (FIG. 13A) and on day 7 of DSS induced colitis (FIG. 13B).

DESCRIPTION OF EXEMPLARY EMBODIMENTS

Figure 1A:
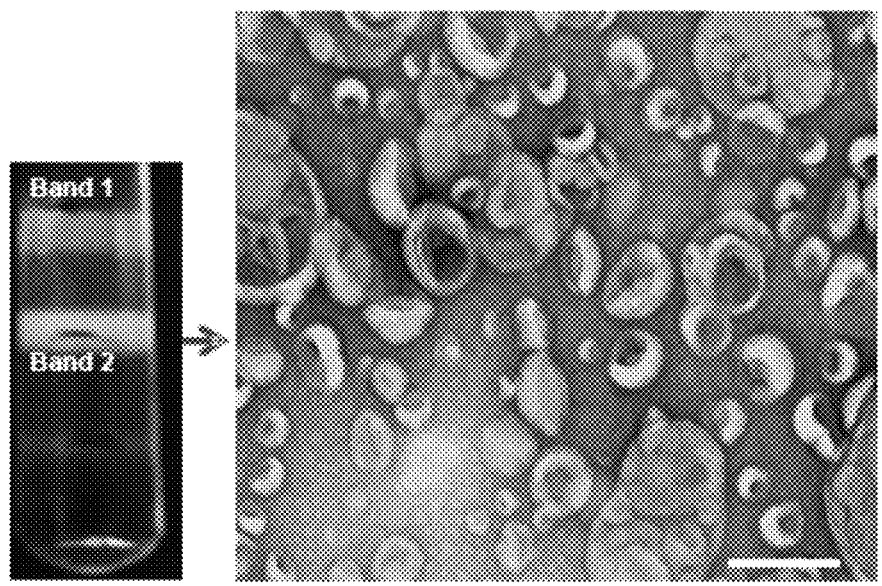
FIGS. 1A-1F include graphs and images showing the characterization of grapefruit-derived nanoparticles (GDNs) including: images showing a sucrose-gradient band (band 2, indicated by the arrow) that was collected for electron microscopy (EM) imaging and examination of GDNs (FIG. 1A, scale bar indicates 200 nm); graphs showing particle size and surface charge measured using a Zetasizer (FIG. 1B); a pie chart of the lipid profile of GDNs, reported as percentage of total lipids in GDNs (PS: Phosphatidylserine; PI: Phosphatidylinositol; PE: Phosphatidylethanolamines; PC: Phosphatidylcholines; and PG: Phosphatidylglycerol) (FIG. 1C); representative high-performance liquid chromatography (HPLC) chromatograms of the standards naringin (NAR), naringenin (NE), and GDN extract and the quantification of the content of NAR and NE in GDNs (FIG. 1D); and graphs showing the particle size (FIG. 1E) and surface charge (FIG. 1F) of GDNs using a Zetasizer (n=6) and after GDNs were incubated in either distilled water, a 0.5N HCl or a 0.5N NaOH solution at 37° C. for 30 min.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Microvesicles are naturally existing nanoparticles that are in the form of small assemblies of lipid particles, are about 50 to 1000 nm in size, and are not only secreted by many types of in vitro cell cultures and in vivo cells, but are commonly found in vivo in body fluids, such as blood, urine and malignant ascites. Indeed, microvesicles include, but are not limited to, particles such as exosomes, epididimosomes, argosomes, exosome-like vesicles, microparticles, promininosomes, prostasomes, dexosomes, texosomes, dex, tex, archeosomes, and oncosomes.

As noted above, microvesicles can be formed by a variety of processes, including the release of apoptotic bodies, the budding of microvesicles directly from the cytoplasmic membrane of a cell, and exocytosis from multivesicular bodies. For example, exosomes are commonly formed by their secretion from the endosomal membrane compartments of cells as a consequence of the fusion of multivesicular bodies with the plasma membrane. The multivesicular bodies are formed by inward budding from the endosomal membrane and subsequent pinching off of small vesicles into the luminal space. The internal vesicles present in the MVBs are then released into the extracellular fluid as so-called exosomes.

As part of the formation and release of microvesicles, unwanted molecules are eliminated from cells. However, cytosolic and plasma membrane proteins are also incorporated during these processes into the microvesicles, resulting in microvesicles having particle size properties, lipid bilayer functional properties, and other unique functional properties that allow the microvesicles to potentially function as effective nanoparticle carriers of therapeutic agents. In this regard, the term "microvesicle" is used interchangeably herein with the terms "nanoparticle," "liposome," "exosome," "exosome-like particle," "nanovesicle," "nano-vector" and grammatical variations of each of the foregoing.

With further respect to microvesicles, the presently-disclosed subject matter is based, at least in part, on the discovery of edible plant-derived microvesicles, which are enriched for phosphatidylethanolamine (PE) and phosphatidylcholine (PC) and which are capable of demonstrating anti-oxidant, anti-inflammatory, and anti-colitic effects. In particular, it has been determined that a number of therapeutic agents, such as the anti-inflammatory agent methotrexate (MTX), can be conjugated to such edible plant-derived microvesicles and that the therapeutic effects of those conjugated therapeutic agents can be significantly enhanced, while their side effects are remarkably reduced.

The presently-disclosed subject matter thus includes compositions comprising edible plant-derived microvesicles and therapeutic agents, which are conjugated to the edible plant-derived microvesicles and are useful in the treatment of various diseases, including inflammatory disorders and cancers. The term "edible plant" is used herein to describe organisms from the kingdom Plantae that are capable of producing their own food, at least in part, from inorganic matter through photosynthesis, and that are fit for consumption by a subject, as defined herein below. Such edible plants include, but are not limited to, vegetables, fruits, nuts, and the like. In some embodiments of the microvesicle compositions described herein, the edible plant is a fruit or a vegetable. In some embodiments, the edible plant is selected from a grape, a grapefruit, a tomato, a ginger, or a carrot, a broccoli, a cabbage, a lettuce, a blackberry, a cauliflower, and a spinach.

The phrase "derived from an edible plant," when used in the context of a microvesicle derived from an edible plant, refers to a microvesicle that, by the hand of man, exists apart from its native environment and is therefore not a product of nature. In this regard, in some embodiments, the phrase "derived from an edible plant" can be used interchangeably with the phrase "isolated from an edible plant" to describe a microvesicle of the presently-disclosed subject matter whose lipid bilayer and other components are obtained from an edible plant and are subsequently manipulated and made to form a microvesicle that is useful for being conjugated with one or more therapeutic agents.

The phrase "conjugated to a microvesicle," or grammatical variations thereof is used herein to refer to therapeutic agents who are connected or are otherwise joined directly to a microvesicle. For instance, in some embodiments, one or more therapeutic agents can be chemically-linked to an edible plant derived microvesicle, such that the one or more therapeutic agents are joined (e.g., by covalent or ionic bonds) directly to the lipid bilayer of the edible plant-derived microvesicle. In some embodiments, the conjugation of various therapeutic agents to the microvesicles can be achieved by first mixing the one or more therapeutic agents with an appropriate cross-linking agent (e.g., N-ethylcarbodiimide ("EDC"), which is generally utilized as a carboxyl activating agent for amide bonding with primary amines and also reacts with phosphate groups) in a suitable solvent. After a period of incubation sufficient to allow the therapeutic agent to attach to the cross-linking agent, the cross-linking agent/therapeutic agent mixture can then be combined with the microvesicles and, after another period of incubation, subjected to a sucrose gradient (e.g., and 8, 30, 45, and 60% sucrose gradient) to separate the free therapeutic agent and free microvesicles from the therapeutic agents conjugated to the microvesicles. As part of combining the mixture with a sucrose gradient, and an accompanying centrifugation step, the microvesicles conjugated to the therapeutic agents are then seen as a band in the sucrose gradient, such that the conjugated microvesicles can then be collected, washed, and dissolved in a suitable solution for use as described herein below.

With further respect to the conjugation of various therapeutic agents to an edible plant-derived microvesicle of the presently-disclosed subject matter, in some embodiments, EDC can be used as a preferred conjugating or cross-linking agent to join the carboxyl groups of the microvesicles to therapeutic agents including primary amines or phosphate groups. In some embodiments that make use of therapeutic agents having a poor water solubility, however, dicyclohexyl carbodiimide ("DCC") can be used to conjugate a therapeutic agent to an exemplary edible plant-derived microvesicle. In some embodiments, still further cross-linking agents may be utilized including, but not limited to, homobifunctional disuccinimidyl, disuccinimidyl tartrate, 3-3'-dithiobis-propionimidate (DTBP), and ethylene glycol bis-succinimidyl succinate (EGS). In some embodiments, the cross-linking agent is selected from N-ethylcarbodiimide (EDC), dicyclohexyl carbodiimide (DCC), homobifunctional disuccinimidyl, disuccinimidyl tartrate, 3-3'-dithiobis-propionimidate (DTBP), and ethylene glycol bis-succinimidyl succinate (EGS). For example, in some embodiments, DCC can used as a cross-linking agent for conversion of carboxylic acids into amides. As another example, in other embodiments that make use of DTBP as the cross-linking agent, by using alkanes and mercaptans as the nucleophiles with DTBP as the oxidant, oxidative C/H/S-H coupling can be achieved. Of course, depending on the particular therapeutic agent selected, numerous other cross-linking agents can also be selected and used as a cross-linking agent without departing from the spirit and scope of the subject matter described herein.

In some embodiments of the presently-disclosed compositions, the therapeutic agent is a phytochemical agent. As used herein, the term "phytochemical agent" refers to a non-nutritive plant-derived compound, or an analog thereof. Examples of phytochemical agents include, but are not limited to compounds such as monophenols; flavonoids, such as flavonols, flavanones, flavones, flavan-3-ols, anthocyanins, anthocyanidins, isoflavones, dihydroflavonols, chalcones, and coumestans; phenolic acids; hydroxycinnamic acids; lignans; tyrosol esters; stillbenoids; hydrolysable tannins; carotenoids, such as carotenes and xanthophylls; monoterpenes; saponins; lipids, such as phytosterols, tocopherols, and omega-3,6,9 fatty acids; diterpenes; triterpinoids; betalains, such as betacyanins and betaxanthins; dithiolthiones; thiosulphonates; indoles; and glucosinolates. As another example of a phytochemical agent disclosed herein, the phytochemical agent can be an analog of a plant-derived compound, such as oltipraz, which is an analog of 1,2-dithiol-3-thione, a compound that is found in many cruciferous vegetables. In some embodiments of the presently-disclosed subject matter, the therapeutic agent is a phytochemical agent selected from curcumin, resveratrol, baicalein, fisetin, and quercetin. In some embodiments, the phytochemical agent is curcumin.

In some embodiments of the compositions of the presently-disclosed subject matter, the therapeutic agent that is conjugated to the exosome is a chemotherapeutic agent. Examples of chemotherapeutic agents that can be used in accordance with the presently-disclosed subject matter include, but are not limited to, platinum coordination compounds such as cisplatin, carboplatin or oxalyplatin; taxane compounds, such as paclitaxel or docetaxel; topoisomerase I inhibitors such as camptothecin compounds for example irinotecan or topotecan; topoisomerase II inhibitors such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example VELCADE® (Millennium Pharmaceuticals, Cambridge, Mass.); or YONDELIS® (Johnson & Johnson, New Brunswick, N.J.). In some embodiments, the chemotherapeutic agent that is conjugated to a microvesicle in accordance with the presently-disclosed subject matter is selected from retinoic acid, 5-fluorouracil, vincristine, actinomycin D, adriamycin, cisplatin, docetaxel, doxorubicin, and taxol.

In further embodiments of the compositions of the presently-disclosed subject matter, the therapeutic agent conjugated to microvesicles is an anti-inflammatory agent. Examples of anti-inflammatory agents that can be used in accordance with the compositions and methods of the presently-disclosed subject matter include, but are not limited to, non-steroidal anti-inflammatory agents (NSAIDS), such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone, acetaminophen, and combinations thereof; COX-2 inhibitors, such as nimesulide, flosulid, celecoxib, rofecoxib, parecoxib sodium, valdecoxib, etoricoxib, etodolac, meloxicam, and combinations thereof glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, rapamycin; or others or analogues of these agents or combinations thereof. In some embodiments, the anti-inflammatory agent is methotrexate, which is also useful in treating cancer. As such, in some embodiments, the term anti-inflammatory agent can be used to describe other classes of therapeutic agents including, for example, phytochemical agents and chemotherapeutic agents.

In other embodiments of the presently-disclosed subject matter, therapeutic agents conjugated to the microvesicle compositions comprise nucleic acid molecules selected from a siRNA, a microRNA, and an expression vector, such as a mammalian expression vector. In some embodiments, and because the microvesicles described herein have numerous carboxylic acids and amine groups, conjugating or cross-linking carboxylic acids to primary amines is performed using the carbodiimide compounds EDC and DCC as both have high capacity to carry nucleic acids such as RNA and cDNA by crosslinking. In this regard, the term "nucleic acid" thus refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) Nucleic Acid Res 19:5081; Ohtsuka et al. (1985) J Biol Chem 260:2605-2608; Rossolini et al. (1994) Mol Cell Probes 8:91-98). The terms "nucleic acid" or "nucleic acid sequence" can also be used interchangeably with gene, open reading frame (ORF), cDNA, mRNA, siRNA, microRNA, and the like.

The terms "small interfering RNA," "short interfering RNA," "small hairpin RNA," "siRNA," and "shRNA" are used interchangeably herein to refer to any nucleic acid molecule capable of mediating RNA interference (RNAi) or gene silencing. See, e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. In one embodiment, the siRNA can comprise a double stranded polynucleotide molecule comprising complementary sense and antisense regions, wherein the antisense region comprises a sequence complementary to a region of a target nucleic acid molecule. In another embodiment, the siRNA can comprise a single stranded polynucleotide having self-complementary sense and antisense regions, wherein the antisense region comprises a sequence complementary to a region of a target nucleic acid molecule. In yet another embodiment, the siRNA can comprise a single stranded polynucleotide having one or more loop structures and a stem comprising self-complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

MicroRNAs are naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression. There are three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

In some embodiments of the presently-disclosed subject matter, a pharmaceutical composition is provided that comprises an edible plant-derived microvesicle composition disclosed herein and a pharmaceutical vehicle, carrier, or excipient. In some embodiments, the pharmaceutical composition is pharmaceutically-acceptable in humans. Also, as described further below, in some embodiments, the pharmaceutical composition can be formulated as a therapeutic composition for delivery to a subject.

A pharmaceutical composition as described herein preferably comprises a composition that includes a pharmaceutical carrier, such as aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

In some embodiments, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of capsules, tablets or lozenges formulated in conventional manner.

Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, the microvesicle compositions of the presently-disclosed subject matter can also be formulated as rectal compositions, such as suppositories or retention enemas, e.g., containing conventional suppository bases such as cocoa butter or other glycerides. Further, the microvesicle compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

Further provided, in some embodiments of the presently-disclosed subject matter, are methods for treating an inflammatory disorder or a cancer. In some embodiments, a method for treating an inflammatory disorder is provided that comprises administering to a subject in need thereof an effective amount of a microvesicle composition of the presently-disclosed subject matter.

As used herein, the terms "treatment" or "treating" relate to any treatment of a condition of interest (e.g., an inflammatory disorder or a cancer), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

As used herein, the term "inflammatory disorder" includes diseases or disorders which are caused, at least in part, or exacerbated by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cancer, or other agents or conditions.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to atherosclerosis; arthritis; asthma; autoimmune uveitis; adoptive immune response; dermatitis; multiple sclerosis; diabetic complications; osteoporosis; Alzheimer's disease; cerebral malaria; hemorrhagic fever; autoimmune disorders; and inflammatory bowel disease. In embodiments, the term "inflammatory disorder" is further inclusive of inflammation-promoted cancers, such that the term "inflammatory disorder" can be used to refer to cancers caused or promoted by inflammation, such as colon cancer. In some embodiments, the inflammatory disorder is selected from the group consisting of sepsis, septic shock, colitis, colon cancer, and arthritis.

For administration of a therapeutic composition as disclosed herein (e.g., an edible plant-derived microvesicle conjugated to a therapeutic agent), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082).

Regardless of the route of administration, the compositions of the presently-disclosed subject matter are typically administered in amount effective to achieve the desired response. As such, the term "effective amount" is used herein to refer to an amount of the therapeutic composition (e.g., a microvesicle conjugated to a therapeutic agent, and a pharmaceutically vehicle, carrier, or excipient) sufficient to produce a measurable biological response (e.g., a decrease in inflammation). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

In some embodiments of the therapeutic methods disclosed herein, administering an edible plant-derived microvesicle composition of the presently-disclosed subject matter reduces an amount of an inflammatory cytokine in a subject. In some embodiments, the inflammatory cytokine can be interleukin-1β (IL-1β), tumor necrosis factor-alpha (TNF-α), or interleukin-6 (IL-6).

Various methods known to those skilled in the art can be used to determine a reduction in the amount of inflammatory cytokines in a subject. For example, in certain embodiments, the amounts of expression of an inflammatory cytokine in a subject can be determined by probing for mRNA of the gene encoding the inflammatory cytokine in a biological sample obtained from the subject (e.g., a tissue sample, a urine sample, a saliva sample, a blood sample, a serum sample, a plasma sample, or sub-fractions thereof) using any RNA identification assay known to those skilled in the art. Briefly, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, Calif.). Because the probes to which the nucleic acid molecules of the sample are bound are known, the molecules in the sample can be identified. In this regard, DNA probes for one or more of the mRNAs encoded by the inflammatory genes can be immobilized on a substrate and provided for use in practicing a method in accordance with the presently-disclosed subject matter.

With further regard to determining levels of inflammatory cytokines in samples, mass spectrometry and/or immunoassay devices and methods can also be used to measure the inflammatory cytokines in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the antibody to the inflammatory molecule can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the inflammatory molecules is also contemplated by the present invention. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

Mass spectrometry (MS) analysis can be used, either alone or in combination with other methods (e.g., immunoassays), to determine the presence and/or quantity of an inflammatory molecule in a subject. Exemplary MS analyses that can be used in accordance with the present invention include, but are not limited to: liquid chromatography-mass spectrometry (LC-MS); matrix-assisted laser desorption/ionization time-of-flight MS analysis (MALDI-TOF-MS), such as for example direct-spot MALDI-TOF or liquid chromatography MALDI-TOF mass spectrometry analysis; electrospray ionization MS (ESI-MS), such as for example liquid chromatography (LC) ESI-MS; and surface enhanced laser desorption/ionization time-of-flight mass spectrometry analysis (SELDI-TOF-MS). Each of these types of MS analysis can be accomplished using commercially-available spectrometers, such as, for example, triple quadrupole mass spectrometers. Methods for utilizing MS analysis to detect the presence and quantity of peptides, such as inflammatory cytokines, in biological samples are known in the art. See, e.g., U.S. Pat. Nos. 6,925,389; 6,989,100; and 6,890,763 for further guidance, each of which are incorporated herein by this reference.

With still further regard to the various therapeutic methods described herein, although certain embodiments of the methods disclosed herein only call for a qualitative assessment (e.g., the presence or absence of the expression of an inflammatory cytokine in a subject), other embodiments of the methods call for a quantitative assessment (e.g., an amount of increase in the level of an inflammatory cytokine in a subject). Such quantitative assessments can be made, for example, using one of the above mentioned methods, as will be understood by those skilled in the art.

The skilled artisan will also understand that measuring a reduction in the amount of a certain feature (e.g., cytokine levels) or an improvement in a certain feature (e.g., inflammation) in a subject is a statistical analysis. For example, a reduction in an amount of inflammatory cytokines in a subject can be compared to control level of inflammatory cytokines, and an amount of inflammatory cytokines of less than or equal to the control level can be indicative of a reduction in the amount of inflammatory cytokines, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Still further provided, in some embodiments, are methods for treating a cancer. In some embodiments, a method for treating a cancer is provided that comprises administering to a subject in need thereof an effective amount of an edible-plant derived microvesicle composition of the presently-disclosed subject matter (i.e., where an edible plant-derived microvesicle is conjugated to a therapeutic agent). In some embodiments, the therapeutic agent conjugated to the microvesicle and used to treat the cancer is selected from a phytochemical agent and a chemotherapeutic agent, as such agents have been found to be particularly useful in the treatment of cancer. As used herein, the term "cancer" refers to all types of cancer or neoplasm or malignant tumors found in animals, including leukemias, carcinomas, melanoma, and sarcomas.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. In some embodiments, the cancer is selected from the group consisting of skin cancer, head and neck cancer, colon cancer, breast cancer, brain cancer, and lung cancer.

As used herein, the term "subject" includes both human and animal subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

The gut mucosal immune system is considered to play an important role in counteracting potential adverse effects of food derived antigens including nanovesicles. The following examples demonstrate that grapefruit derived nanovesicles (GDNs) are selectively taken up by intestinal macrophages and ameliorate dextran sulfate sodium (DSS)-induced mouse colitis. These effects were mediated by up-regulating the expression of heme oxygenase-1 (HO-1) and inhibiting the production of IL-1β and TNF-α in intestinal macrophages. The biocompatibility and biodegradability, stability at wide ranges of pH values, and targeting of intestinal macrophages led to the further development of a novel GDN-based oral delivery system. Incorporating methotrexate (MTX), an anti-inflammatory agent, into GDNs and delivering the MTX-GDNs to mice significantly lowered the MTX toxicity when compared to free MTX, and remarkably increased its therapeutic effects in DSS-induced mouse colitis. These findings demonstrate that GDNs can serve as immune modulators in the intestine, maintain intestinal macrophage homeostasis and can be developed for oral delivery of small molecule drugs to attenuate inflammatory responses in human disease.

Materials and Methods

Preparation and Characterization of Grapefruit-Derived Nanovesicles (GDNs). Grapefruit skin was removed and the fruit pulp homogenized in a high-speed blender for 1 min at 4° C. The collected juice was sequentially centrifuged at 2000 g for 20 min and then 10,000 g for 1 h to exclude debris. The nanovesicles were pelleted at 150,000 g for 1.5 h, washed once with PBS and then purified and separated using sucrose gradients (8, 30, 45 and 60%, respectively). Band 1 at the 8%/30% interface and band 2 at the 30%/45% interface were separately harvested. The concentration of samples was represented as protein concentration using the Bio-Rad protein quantification assay kit (Bio-Rad, Hercules, Calif.).

Particle Size and Surface Charge Analysis.

The particle size and zeta potential were measured using a Zetasizer Nano ZS (Malvern Instrument, UK) with the following settings: 11 measurements per samples, 25° C. and baseline viscosity for water established at 0.8872 cP.

Electron Microscopy.

Particle pellets were fixed and processed for EM using a conventional procedure and observed with a JEOL model 1200EX electron microscope (JEOL, Tokyo, Japan). Digital images were acquired using an AMT Advantage HR (Advanced Microscopy Techniques, MA) high definition CCD, 1.3 megapixel TEM camera.

Lipid Extraction and Lipidomic Analysis.

Total lipid extraction of GDNs was performed according to the method of Bligh and Dyer, and the lipids were dissolved in chloroform for analysis. The lipid composition was analyzed on a triple quadrupole tandem mass spectrometer (API 4000, Applied Biosystems, CA) as previously described. The data were reported as percentage of total signal of the molecular species after normalization of the signals to internal standards of the same lipid class.

Proteomic Analysis.

Total proteins were extracted from GDNs using Trizol (Invitrogen) following the manufacturer's instruction and the proteins re-suspended in 1% SDS with 0.8 M urea. Proteins were electrophoresed on 10% SDS-polyacrylamide gels, stained with Coomassie blue and then the individual protein bands were cut and sent for proteomics analysis as described previously.

Extraction of Naringin from GDNs.

The extraction procedure was performed as previously described. In brief, 5 mg of GDNs (based on protein concentration) were resuspended in 800 μl of 50% ethanol, heated to 90° C. immediately and allowed to stand for 2 hours. The extracts were cooled to 22° C. and filtered for HPLC analysis.

High-Performance Liquid Chromatography (HPLC).

Chromatography was performed on an Agilent 1120 system. An Eclipse Plus C18 column was employed. The mobile phase consisted of 20 mM HCl (A)/Acetonitrile (B). The separation was performed as previously described. The UV detector was set at 280 nm. The analyses were performed at 25° C. with a 1 ml/min flow rate and the injection volume was 100 µl.

In Vitro Digestion.

In vitro digestion conditions were based on a previous description. One ml of GDNs in a water solution were incubated with slow rotation at 37° C. for 30 min after the addition of 1.34 µl of 18.5% w/v HCl (pH 2.0) and 24 µl of a pepsin solution (80 mg/ml in 0.1 N of HCl, pH 2.0, Sigma). Then, 80 µl of a mixture containing 24 mg/ml of bile extract and 4 mg/ml of pancreatin (Sigma) in 0.1 N of $NaHCO_3$ was added. The pH value of the bulk solution was adjusted to 6.5 with 1 N $NaHCO_3$ and GDNs were incubated for another 30 min under the same conditions. The stability of GDNs was evaluated by changes of particle size and surface charge.

Preparation of GDN-MTX Conjugates (GMTX).

GMTX was prepared as previous described. In brief, MTX (2 mg, Sigma) with EDC (1.5 mg, Thermo Scientific) was dissolved in DMSO (0.125 ml). The solution was incubated at 50° C. for 15 min, cooled to 22° C. and then added to GDN solution (25 mg in 3 ml PBS pH 7.4). After 2 h of reaction, GMTX conjugates were purified using a sucrose gradient. The concentration of MTX in the conjugates was determined by using UV-spectrophotometry at a wavelength of 307 nm (Nanodrop 8000, Thermo scientific) with unconjugated GDNs as blanks. The GDNs content in the conjugates was represented by their protein concentration.

In Vitro Release of MTX.

Free MTX (0.5 mg) and GMTX (MTX equaled to 0.5 mg) were each dissolved in 0.5 ml of PBS. The solutions were dispensed into a dialysis cassette (cutoff 10 kDa, Pierce). The cassettes were placed into capped dishes containing 1.5 ml of PBS as a release medium. These dishes were placed on a shaker (15 rpm/min) at 37° C. Every hour, 0.1 ml of release medium was removed from the incubated dishes, and replaced with 0.1 ml fresh PBS. Collected samples were assayed spectrophotometrically for MTX at 307 nm.

Experimental Animals.

Six-to eight-week old C57BL/6J male mice were purchased from The Jackson Laboratory (Bar Harbor, Me.). All experiments were approved by the Institutional Animal Care and Use Committee at the University of Louisville.

Biodistribution and Cellular Target of Orally Administrated GDNs.

Mice fasted overnight were orally given 30 mg/kg of either near-infrared lipophilic carbocyanine dye (1,1'-dioctadecyl-3,3,3'3'-tetramethyl-indotricarbocyanine-iodide, DiR, Invitrogen, Carlsbad, Calif.) or PKH26 fluorescent dye (Sigma) labeled GDNs twice, i.e., at 2 h and 4 h before tissues were harvested. Mice were sacrificed and small intestine, colon, Peyer's patch, mesenteric lymph node (MLN), spleen and liver tissues were used for immunofluorescence staining and imaging.

DSS-Induced Colitis.

Colitis was induced in mice by addition of 2% (wt/vol) DSS (MW 36-50 KD molecular weight, MP Biomedicals, OH) in their drinking water for the duration of the study. DSS solution was freshly prepared every other day. Body weight and physical activity were monitored daily. To test the protective effect of GDNs, mice fasted for 4 h were orally given either PBS or 10 mg/kg of GDNs daily for 7 days and then treated with 2% DSS in drinking water for 7 days to induce colitis with continued administration of GDNs. To test the therapeutic effect of GMTX, colitis was first induced in mice by providing 2% DSS in their drinking water. On day 3, 5 and 6 of DSS-induced colitis, mice were treated with free MTX (5 mg/kg body weight) or GMTX (MTX equaled to 5 mg/kg) by oral administration. Five mg/kg was pre-determined to have optimal therapeutic effect.

AST and ALT Measurement.

To test for hepatotoxicity, levels of ALT and AST activity in serum were measured using the Infinity Enzymatic Assay Kit (Thermo Scientific).

Detection of Mouse Commensal Bacteria.

DNA from mouse feces was extracted using the QIAgen stool kit for stool pathogen detection. qPCR assays were performed on a CFX96 Real-Time System (BioRad) using SYBR Green Master Mix (Bio-Rad laboratories) and bacteria or phyla-specific primers.

Histology.

For histopathology, tissues were fixed in 10% neutral formalin and then embedded in paraffin. Tissue samples were cut at 5 µm thicknesses and stained with either hematoxylin and eosin or Alcian blue and nuclear fast red. Histological examination was performed in a blinded fashion and the severity of colitis was scored as described previously. For immunofluorescence analysis, tissue sections were first blocked at 22° C. for 1 h with 5% BSA in PBS. Slides were incubated at 4° C. overnight with the primary antibodies: E-cadherin (1:1000, BD Bioscience) and F4/80 (1:200, Biolegend). E-cadherin and F4/80 binding was detected by Alexa Fluor 488 conjugated goat antimouse IgG or goat anti-rat IgG (1:600, Invitrogen), respectively. Apoptosis in colon tissues was identified by TUNEL assay using the in situ Cell Death Detection kit from Roche Applied Science (Indianapolis, Ind.). Tissues were counterstained with DAPI and images were captured on a Zeiss LSM 510 confocal microscope equipped with a digital image analysis system (Pixera).

Internalization Assay.

Macrophages were plated on Lab-Tek chamber slide (Sigma) and incubated for 24 h in growth medium. Before the uptake assay, GDNs were labeled with PKH26, sucrose gradient purified and diluted in PBS. Uptake was performed by incubating cell cultures with 2 µg/ml of GDNs for 3 h in a humid chamber (37° C., 5% $CO_2$). For inhibition experiments, cell cultures were pre-incubated with individual inhibitors for 30 min before performing the uptake experiments.

Isolation of Intestinal Epithelial Cells, Intestinal Leukocytes and Flow Cytometry.

Intestinal epithelial cells (IEC), intraepithelial leukocytes (IEL) and lamina propria leukocytes (LPL) were isolated as described previously. Briefly, intestines were flushed with PBS, everted, and rinsed in cold PBS three times. For epithelial isolation, tissues were treated with 0.5 mM dithiothreitol for 30 min at 37° C. with slow rotation, followed by vortexing for 1 min. The liberated IEC were collected and subjected to Percoll (GE Healthcare) discontinuous gradient centrifugation. IEC were recovered at the interface of the 20 and 40% Percoll solutions. For lymphocyte isolation, tissues were incubated twice in 25 ml of IEL medium (RPMI 1640 containing penicillin/streptomycin, 0.02 M HEPES and 2% FBS) for 20 min at 37° C. with slow rotation (150 rpm/min).

IELs were removed by vigorous vortexing and filtering through a 100 μm cell strainer and new IEL solution was added. After a second round incubation, the tissues were washed in HBSS, cut into small pieces and placed in 5 ml of digestion solution (IEL medium with 1 mg/ml Collagenase type VIII and 50 μg/ml DNase I (Sigma)) at 37° C. for two rounds of incubation at 25 min each with slow rotation. Cells were filtered through a cell strainer and subjected to Percoll discontinuous gradient centrifugation. IELs and LPLs were recovered at the interface of the 40 and 80% Percoll solutions. IELs and LPLs were suspended in PBS/0.5% BSA and stained for 45 min with anti-CD3 Ab (145 2C11, eBioscience), anti-TCRγδ Ab (eBioGL3, eBioscience), anti-F4/80 (C1:A3-1, Serotec), anti-CD4 Ab (GK1.5), anti-CD8 Ab (53-6.7), anti-CD11b Ab (M1/70) and Gr1 Ab (RB6-8C5) (all from Biolegend unless otherwise noted). In some experiments, stained cells were sorted to purify indicated populations on a BD FACS Aria III.

For intracellular staining, cells were stimulated with 20 ng/ml PMA (phorbol 12-myristate 13-acetate, Sigma) and 0.5 μg/ml ionomycin (Sigma) for 5 h in the presence of Golgistop (BD Bioscience) in the media. After stimulation, cells were first stained with surface Ab and fixed, then permeabilized, and stained for intercellular TNF-α. The relevant isotype Abs were used as controls.

For FACS analysis of cell proliferation, RAW264.7 cells labeled with carboxyfluorescein diacetate succinimidyl ester (CFSE, invitrogen) were plated in a 24-well plate and incubated for 72 h with MTX or GMTX at the indicated concentration. Proliferation was measured by CFSE dilution.

Flow cytometry analysis was performed using a FACS Calibur (BD Bioscience) and analyzed using FlowJo software (Tree Star Inc.).

Colon Organ Culture.

To assess the local levels of IL-6, IL-1β, TNF-α, organ cultures were generated from naïve, GDN, PBS/DSS and GDN/DSS challenged mice. In brief, the distal most 2 cm of colon was washed with PBS containing penicillin/streptomycin and then further cut into 1 $cm^2$ sections. Colon sections were cultured in serum free RPMI 1640 medium supplemented with penicillin/streptomycin. After 24 h, cell-free supernatants were harvested and assayed for cytokine secretion by ELISA kits (eBioscience). The local levels of $PGE_2$ were determined by a $PGE_2$-specific EIA (Cayman Chemical, Ann Arbor, Mich.) as described previously.

Real-Time PCR.

Total RNA was extracted from either distal colon or GDN treated intestinal macrophages using Trizol (Invitrogen) and reverse-transcribed with random primers (Invitrogen Superscript III). qPCR analysis was done using the SYBR Green Master Mix (Bio-Rad laboratories) and specific primers (for primer sequences, see U.S. Provisional Patent Application No. 62/036,850, which is incorporated herein by reference). Signals were normalized to GPDH and β-actin levels within each sample and normalized data were used to calculate ΔΔCt and determine the relative levels of gene expression.

ELISA.

To test the potential immunomodulation effect of GDNs on lamina propria macrophages (LPMs), Freshly isolated LPMs ($10^6$/ml) were stimulated by heat killed *E. coli* bacteria (MOI=50) for 24 h at 37° C. Culture supernatants were collected and the production of IL-10 and TNF-α were assessed using ELISA kits (eBioscience).

Statistical Analysis.

Data are represented as mean±standard error (SEM). Statistical significance was calculated using either the student's t-test for two samples with unequal variances or one-way ANOVA with Holm's post hoc test for three variables with *$p<0.05$ and **$p<0.01$ as levels of significance.

Example 1—Characterization of Grapefruit Derived Nanovesicles (GDNs)

Figure 1B:
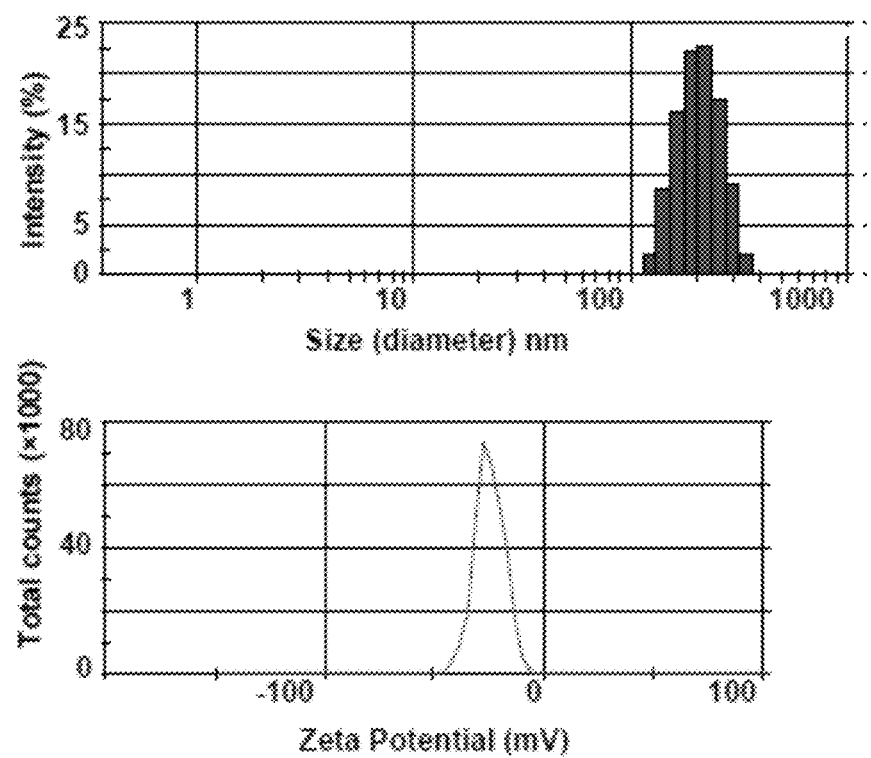
Figure 1C:
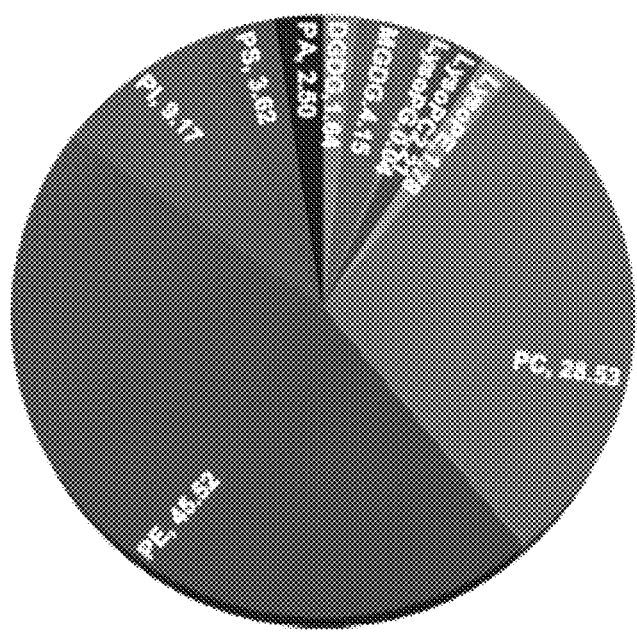
Figure 1D:
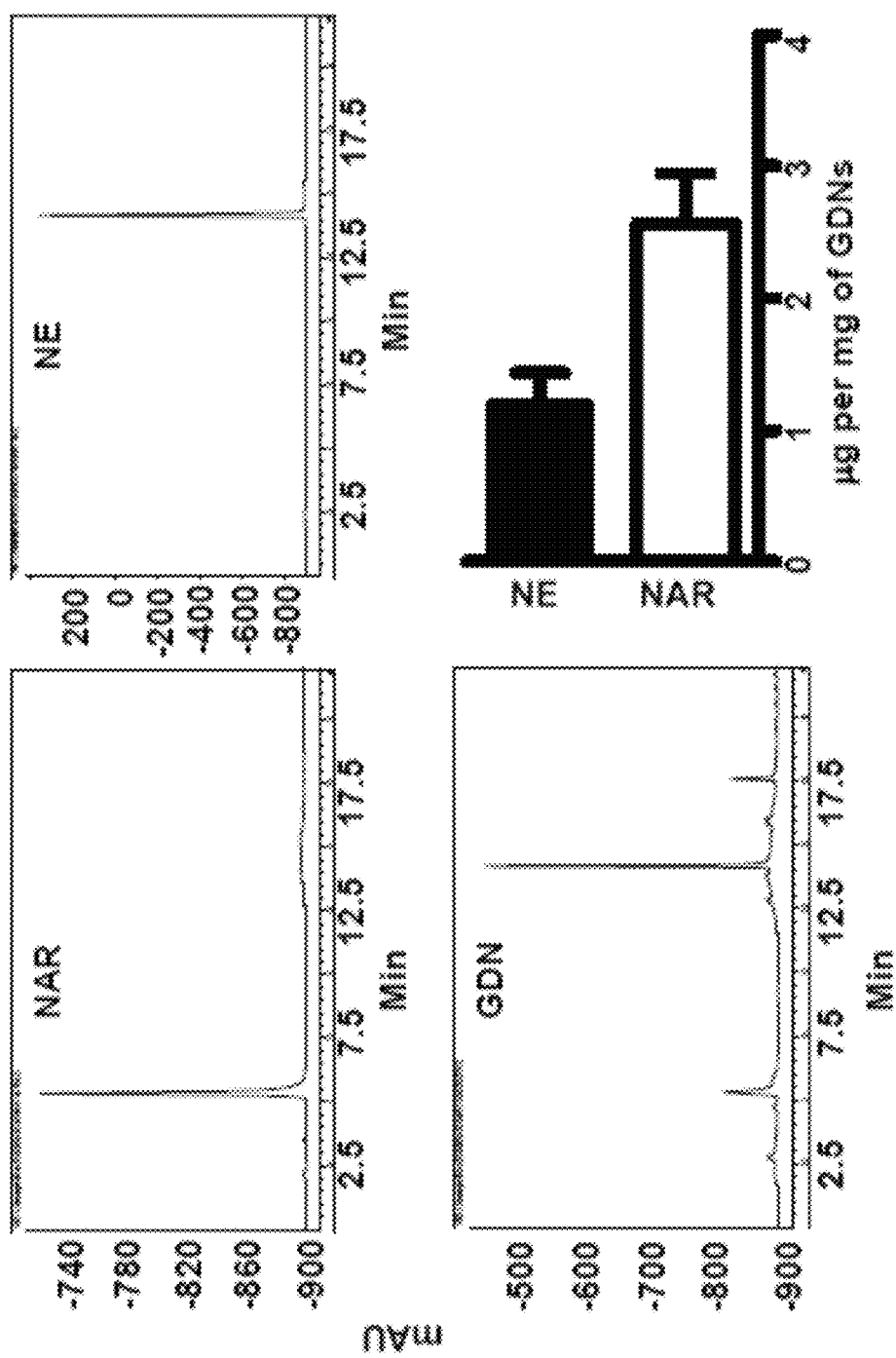

Grapefruit juice nanovesicles were isolated from the fruit pulp using a sucrose gradient centrifugation method. The majority of the nanovesicles accumulated at the 8%/30% interface (band 1), and 30%/45% interface (band 2) of the sucrose gradient. Vesicles from band 1 were excluded in the following studies because preliminary data suggested that their role in preventing or ameliorating DSS-induced colitis in a mouse model could not be determined. Vesicles integrity and size was evaluated by EM (FIG. 1A) and a nano zetasizer (FIG. 1B). The results indicated that the vesicles were nano-size and that the size distribution range of isolated GDNs spanned a diameter from 105.7 to 396.1 nm and the average diameter of the vesicles population was 210.8±48.62 nm. Zeta potential measurements indicated that GDNs had a negative zeta potential value ranging from −49.2 mV to −1.52 mV. Like the lipid profile of mammalian microvesicles, lipidomic data indicated that GDNs were enriched with PE (45.52%) and PC (28.53%) (FIG. 1C). In particular, PE (34:2) and PC (34:2) were highly enriched (Table I) and, interestingly, among the lipids that were analyzed naringin and its metabolite, the functional component naringenin were detected (FIG. 1D). Similar to exosome-like nanoparticles identified in grapes, mass spectrometer analysis of the GDN protein profile indicated that a number of proteins identified in GDNs regulate carbohydrates/lipid metabolism (Table II).

TABLE I

Composition of phosphocholine (PC) and phosphoethanolamine (PE) found in GDN.

| Formula | Name | Percentage |
|---|---|---|
| PC | | |
| C40H80O8PN | PC(32:0) | 1.53 |
| C42H76O8PN | PC(34:4) | 0.86 |
| C42H78O8PN | PC(34:3) | 10.67 |
| C42H80O8PN | PC(34:2) | 28.63 |
| C42H82O8PN | PC(34:1) | 13.88 |
| C44H76O8PN | PC(36:6) | 0.48 |
| C44H78O8PN | PC(36:5) | 4.07 |
| C44H80O8PN | PC(36:4) | 11.34 |
| C44H82O8PN | PC(36:3) | 18.36 |
| C44H84O8PN | PC(36:2) | 8.49 |
| C44H86O8PN | PC(36:1) | 0.72 |
| C46H80O8PN | PC(38:6) | 0.05 |
| C46H82O8PN | PC(38:5) | 0.02 |
| C46H84O8PN | PC(38:4) | 0.07 |
| C46H86O8PN | PC(38:3) | 0.32 |
| C46H88O8PN | PC(38:2) | 0.33 |
| C48H86O8PN | PC(40:5) | 0.00 |
| C48H88O8PN | PC(40:4) | 0.01 |
| C48H90O8PN | PC(40:3) | 0.08 |
| C48H92O8PN | PC(40:2) | 0.09 |
| PE | | |
| C37H68O8PN | PE(32:3) | 0.02 |
| C37H70O8PN | PE(32:2) | 0.39 |
| C37H72O8PN | PE(32:1) | 2.28 |
| C37H74O8PN | PE(32:0) | 0.17 |
| C39H70O8PN | PE(34:4) | 0.37 |
| C39H72O8PN | PE(34:3) | 7.78 |
| C39H74O8PN | PE(34:2) | 37.01 |

TABLE I-continued

Composition of phosphocholine (PC) and phosphoethanolamine (PE) found in GDN.

| Formula | Name | Percentage |
|---|---|---|
| C39H76O8PN | PE(34:1) | 7.62 |
| C41H70O8PN | PE(36:6) | 0.30 |
| C41H72O8PN | PE(36:5) | 3.04 |
| C41H74O8PN | PE(36:4) | 14.98 |
| C41H76O8PN | PE(36:3) | 18.10 |
| C41H78O8PN | PE(36:2) | 5.12 |
| C41H80O8PN | PE(36:1) | 0.34 |
| C43H74O8PN | PE(38:6) | 0.04 |
| C43H76O8PN | PE(38:5) | 0.00 |
| C43H78O8PN | PE(38:4) | 0.12 |
| C43H80O8PN | PE(38:3) | 0.37 |
| C45H84O8PN | PE(40:3) | 0.29 |
| C45H86O8PN | PE(40:2) | 0.51 |
| C47H86O8PN | PE(42:4) | 0.01 |
| C47H88O8PN | PE(42:3) | 0.14 |
| C47H90O8PN | PE(42:2) | 1.01 |

TABLE II

Identities of proteins found in GDNs

| Protein name | Accession number | Molecular weight |
|---|---|---|
| (E)-beta-farnesene synthase | G8Z362 (+1) | 64 kDa |
| (E)-beta-ocimene synthase | Q5CD81 | 71 kDa |
| 1,2 rhamnosyltransferase | D0UZK1 (+2) | 51 kDa |
| 1,6-rhamnosyltransferase | A7ISD3 | 53 kDa |
| 280 kDa protein | Q80H98 | 280 kDa |
| 286 kDa polyprotein | Q15GA4 (+2) | 286 kDa |
| 2-phospho-D-glycerate hydrolase | D7NHW9 | 48 kDa |
| 349 kDa polyprotein | D0EAL9 | 348 kDa |
| 349-kDa polyprotein | Q9DTG5 | 349 kDa |
| Acidic cellulase | O22297 | 55 kDa |
| Acidic class I chitinase | Q8H986 | 34 kDa |
| Aconitate hydratase 1 | D3GQL0 | 98 kDa |
| Actin | K7N8A0 | 42 kDa |
| Alcohol acyl transferase | A8W8Y0 | 51 kDa |
| Allene oxide synthase | Q84V85 | 59 kDa |
| Aminopeptidase | F8WL79 | 102 kDa |
| Apocytochrome f | Q09MG5 | 35 kDa |
| Ascorbate peroxidase | J7EIR8 | 28 kDa |
| Ascorbate peroxidase | B9VRH6 | 28 kDa |
| Auxin-response factor | G9I820 | 94 kDa |
| Beta-amylase | J7ICW8 | 65 kDa |
| Beta-galactosidase | Q8L5Q9 | 82 kDa |
| Beta-pinene synthase | A7BG60 | 69 kDa |
| Beta-tubulin | C0KLD1 | 50 kDa |
| Capsid protein | Q91QZ1 | 41 kDa |
| Capsid protein | Q3SAK9 | 31 kDa |
| Cation chloride cotransporter | D2U833 | 108 kDa |
| Chalcone synthase | C3VPJ0 (+3) | 43 kDa |
| Chloride channel protein | D5LM39 | 86 kDa |
| Cinnamate 4-hydroxylase CYP73 | Q9M4U0 | 61 kDa |
| Citrin | Q39627 | 55 kDa |
| Coat protein | G2XKD3 | 25 kDa |
| Coat protein | Q3L2I6 | 25 kDa |
| CRT/DRE binding factor | D5FV16 | 24 kDa |
| CTV.2 | Q8H6S5 | 124 kDa |
| CTV.20 | Q8H6Q8 | 364 kDa |
| CTV.22 | Q8H6Q7 | 155 kDa |
| Cytochrome P450 | Q1I1D7 | 54 kDa |
| Dehydrin | Q7Y045 | 27 kDa |
| DNA excision repair protein | F8WLD2 | 74 kDa |
| DNA-directed RNA polymerase subunit beta" | Q09MI8 | 159 kDa |
| Ethylene response 1 | D2WKC9 | 83 kDa |
| Ethylene response sensor 1 | D2WKD2 | 71 kDa |
| Ethylene-insensitive 3-like 1 protein | D7PVG7 | 70 kDa |
| Eukaryotic translation initiation factor 3 subunit E | G3CHK8 | 52 kDa |
| Fatty acid hydroperoxide lyase | A9NJG4 (+3) | 56 kDa |

TABLE II-continued

Identities of proteins found in GDNs

| Protein name | Accession number | Molecular weight |
|---|---|---|
| F-box family protein | B8Y9B5 | 53 kDa |
| Fe(III)-chelate reductase | Q000W4 | 80 kDa |
| Fructokinase | Q6Q3H4 | 38 kDa |
| Gag-pol polyprotein | F8WL95 | 177 kDa |
| Gamma-terpinene synthase, chloroplastic | Q8L5K4 | 70 kDa |
| Glucose-1-phosphate adenylyltransferase | Q9SP43 | 57 kDa |
| Glutathione S-transferase | Q3HM93 | 24 kDa |
| GRAS family transcription factor | D0VEW6 | 57 kDa |
| Heat shock protein | F8WL87 | 34 kDa |
| Hsp90 | H9NHK0 | 80 kDa |
| Jp18 | Q8H6R4 | 23 kDa |
| Leucine-rich repeat family protein | G3CHK6 | 51 kDa |
| Limonoid UDP-glucosyltransferase | B2YGX9 (+1) | 57 kDa |
| MADS-box protein | Q05KK0 | 30 kDa |
| Mechanosensitive ion channel domain-containing protein | F8WLB4 | 79 kDa |
| Monoterpene synthase | Q5CD82 | 70 kDa |
| MYB transcription factor | F8WLC4 | 23 kDa |
| NAC domain protein | A5YWA9 | 35 kDa |
| NAD(P)H-quinone oxidoreductase subunit 5, chloroplastic | Q09MC9 | 84 kDa |
| NBS-LRR type disease resistance protein | Q8H6R9 | 102 kDa |
| NBS-LRR type disease resistance protein | Q8H6S0 | 101 kDa |
| NBS-LRR type disease resistance protein | Q8H6R6 | 101 kDa |
| p1a | J9WR93 | 348 kDa |
| P23 | Q1X8V8 | 24 kDa |
| P23 | E7DSS0 (+4) | 24 kDa |
| p27 | G0Z9I6 | 27 kDa |
| p33 | I3XHN0 | 34 kDa |
| p33 protein | B8YDL3 | 34 kDa |
| p33 protein | B9VB22 | 34 kDa |
| P346 | P87587 | 347 kDa |
| p349 protein | B9VB56 | 349 kDa |
| p349 protein | I3RWW7 | 347 kDa |
| p349 protein | B9VB20 | 348 kDa |
| p349 protein | Q9WID7 | 347 kDa |
| P353 | Q2XP16 | 353 kDa |
| Pectinesterase 1 | O04886 (+1) | 64 kDa |
| Peptidyl-prolyl cis-trans isomerase | F8WL74 | 58 kDa |
| Peroxidase | Q0ZA67 | 37 kDa |
| Phosphoenolpyruvate carboxylase | F1CT41 | 100 kDa |
| Phytoene synthase | B1PBV7 (+2) | 50 kDa |
| Plastid-lipid-associated protein, chloroplastic | Q9ZWQ8 | 35 kDa |
| Pol polyprotein | Q94FM1 | 33 kDa |
| Pol polyprotein | Q94FM0 | 80 kDa |
| Poly C-binding protein | G9I825 | 62 kDa |
| Polygalacturonase inhibitor | O64460 (+7) | 36 kDa |
| Polyprotein | I3XHM8 | 349 kDa |
| Polyprotein | C0STR9 | 175 kDa |
| Polyprotein | H6U1F0 | 148 kDa |
| Polyprotein | B8QHP8 | 242 kDa |
| Polyprotein | I3V6C0 | 241 kDa |
| Polyprotein | C0STS0 | 175 kDa |
| Polyprotein | K0FGH5 | 241 kDa |
| Polyprotein | Q3HWZ1 | 241 kDa |
| PPR containing protein | F8WLA5 | 64 kDa |
| Probable phospholipid hydroperoxide glutathione peroxidase | Q06652 (+1) | 19 kDa |
| Profilin | P84177 | 14 kDa |
| Protein ycf2 | Q09MB4 | 268 kDa |
| PSI reaction center subunit II | A8C183 | 23 kDa |
| Putative 2b protein | A5JVP6 | 22 kDa |
| Putative eukaryotic translation initiation factor 1 | D0EFM2 | 32 kDa |
| Putative gag-pol polyprotein | Q18L98 | 152 kDa |
| Putative movement protein | B5AMI9 | 40 kDa |
| Putative multiple stress-responsive zinc-finger protein | A1ECK5 | 18 kDa |
| Putative replicase polyprotein | B5AMJ0 | 227 kDa |
| Putative RNA-dependent RNA polymerase | I7CYN5 | 186 kDa |
| Putative terpene synthase | Q8RVR2 | 64 kDa |
| Putative uncharacterized protein | B5TE89 | 169 kDa |
| Putative uncharacterized protein | Q8JVF3 | 54 kDa |
| Putative uncharacterized protein ORF43 | F8WLB0 | 52 kDa |

TABLE II-continued

Identities of proteins found in GDNs

| Protein name | Accession number | Molecular weight |
|---|---|---|
| Putative viral replicase | A5JVP4 | 121 kDa |
| Replicase | M1JAW3 | 285 kDa |
| Replicase polyprotein | H6VXK8 | 230 kDa |
| Replicase protein 1a | J9UF50 (+1) | 118 kDa |
| Replicase protein 2a | J9RV45 | 95 kDa |
| Replicase-associated polyprotein | Q5EGG5 | 240 kDa |
| RNA recognition motif protein 1 | G9I823 | 86 kDa |
| RNA-dependent RNA polymerase | J7EPC0 | 187 kDa |
| RNA-directed RNA polymerase L | Q6DN67 | 280 kDa |
| SEPALLATA1 homolog | A9CQM4 | 28 kDa |
| Sucrose synthase | Q9SLS2 | 92 kDa |
| Sucrose synthase | Q9SLV8 (+1) | 93 kDa |
| Temperature-induced lipocalin | Q38JC1 | 22 kDa |
| Tetratricopeptide domain-containing thioredoxin | D0ELH6 | 37 kDa |
| Thaumatin-like protein | D2KU75 | 27 kDa |
| Translation elongation factor | C3VIC2 | 48 kDa |
| Ubiquitin/ribosomal fusion protein | D5LY07 | 18 kDa |
| UDP-glucosyltransferase family 1 protein | C6KI43 | 56 kDa |
| Vacuolar citrate/H+ symporter | A0FKR1 | 57 kDa |
| Vacuolar invertase | Q944C8 | 65 kDa |
| V-type proton ATPase subunit E | Q9MB46 | 26 kDa |
| WD-40 repeat family protein | F8WL82 | 58 kDa |

Figure 1E:
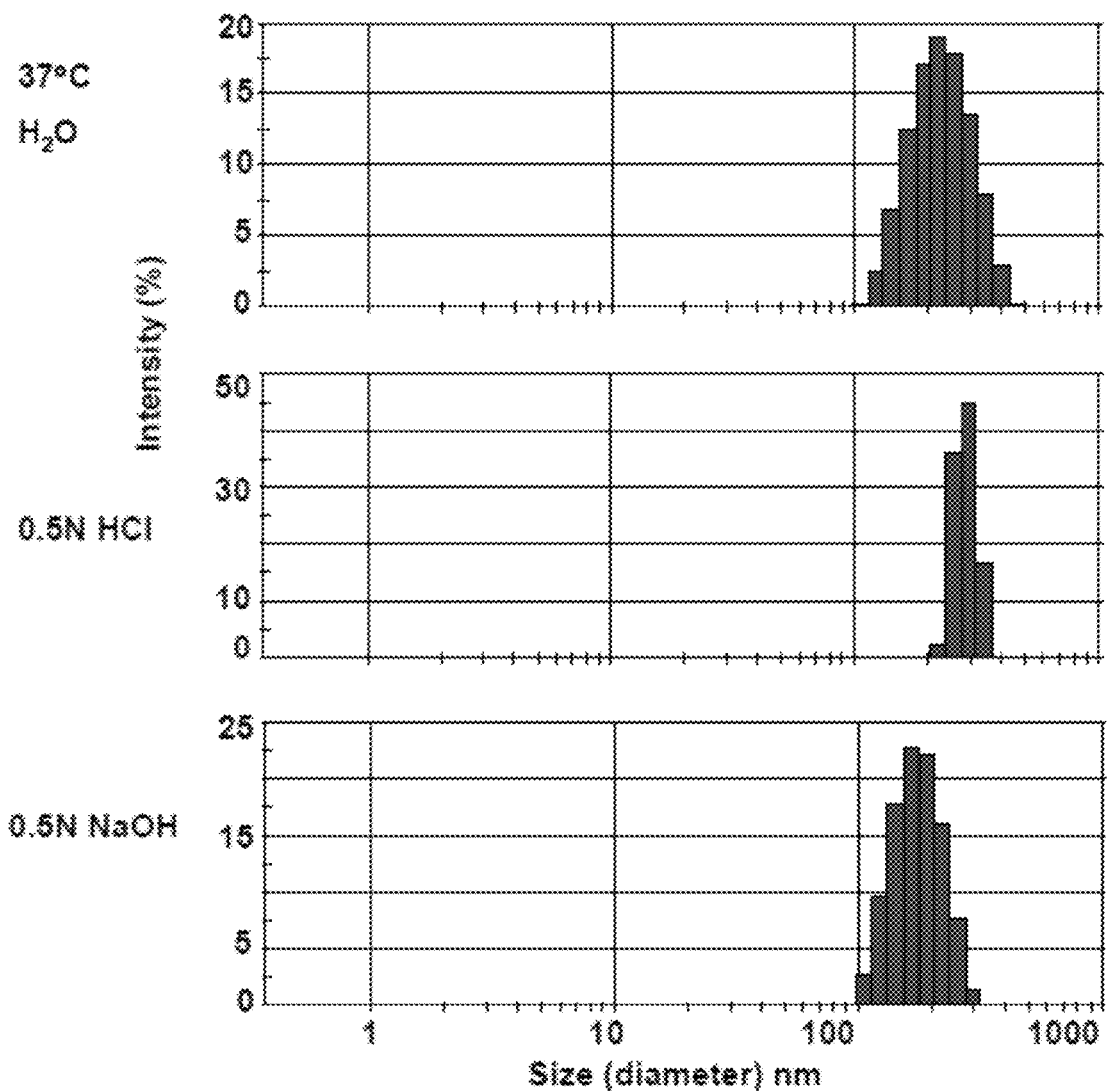
Figure 1F:
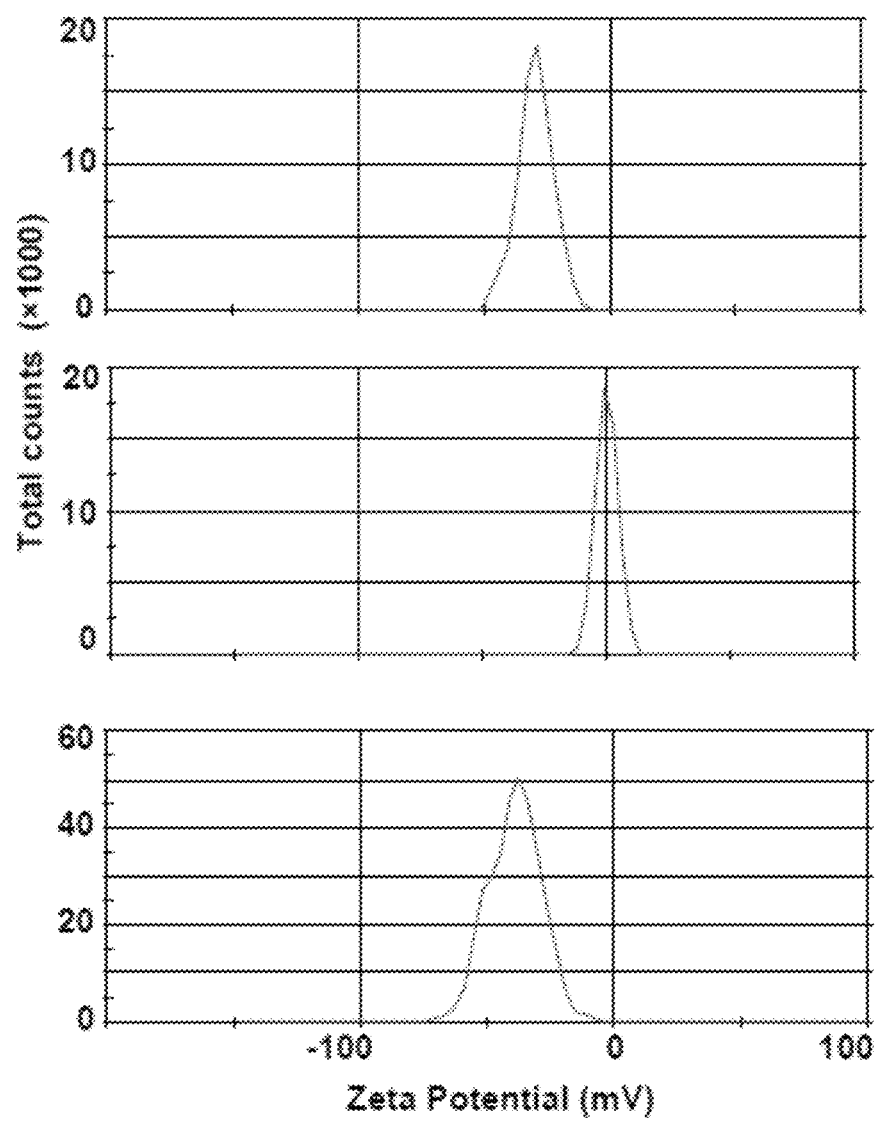
Figure 9A:
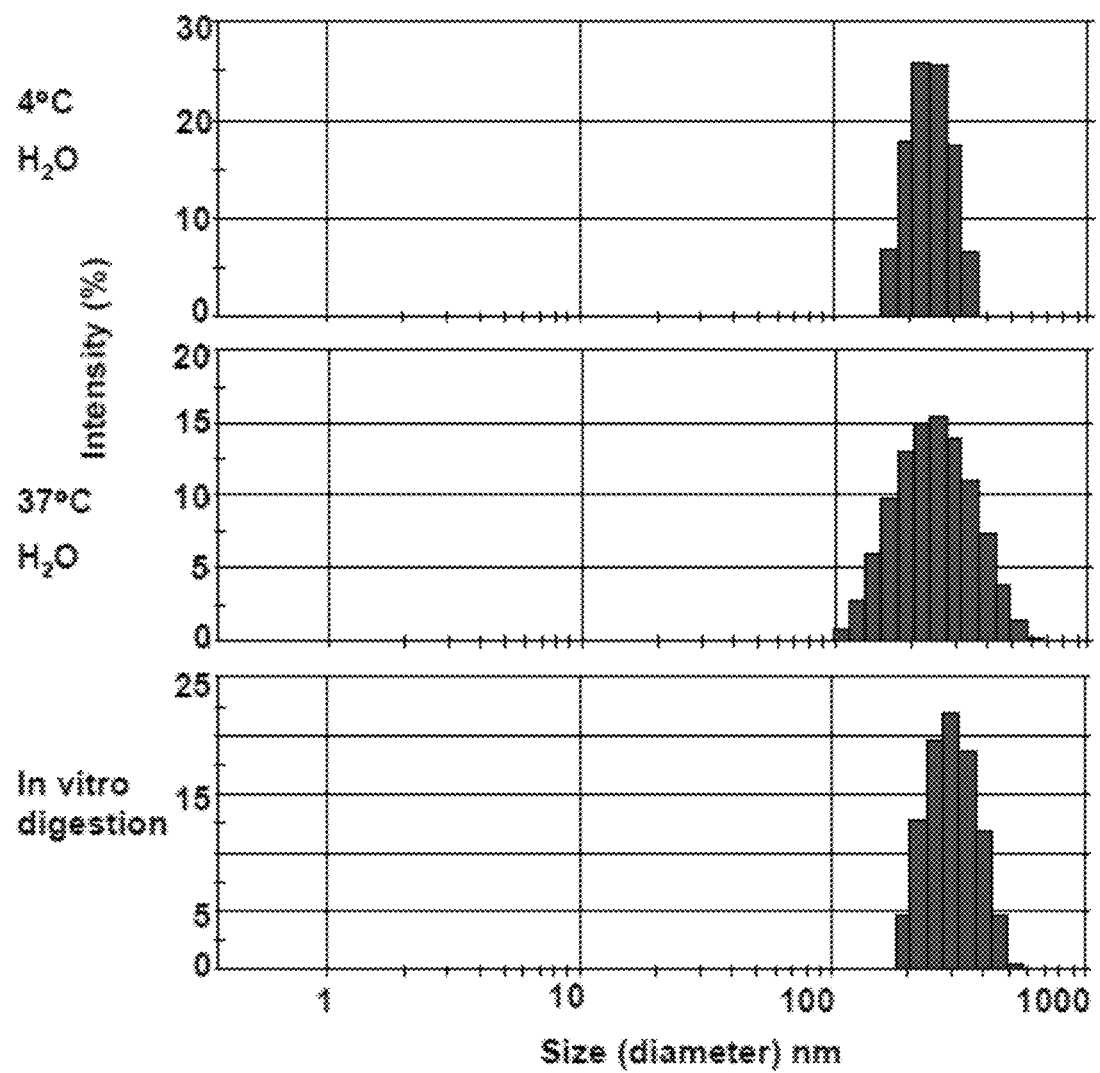
FIGS. 9A-9B include graphs showing that GDNs are resistant to gastric and intestinal enzymatic digestion, where GDNs were incubated first in pepsin solution at 37° C. for 30 min, then with pancreatin and bile extract solution for another 30 min, and where the change of particle size (FIG. 9A) and surface charge (FIG. 9B) were measured using a Zetasizer (n=5).
Figure 9B:
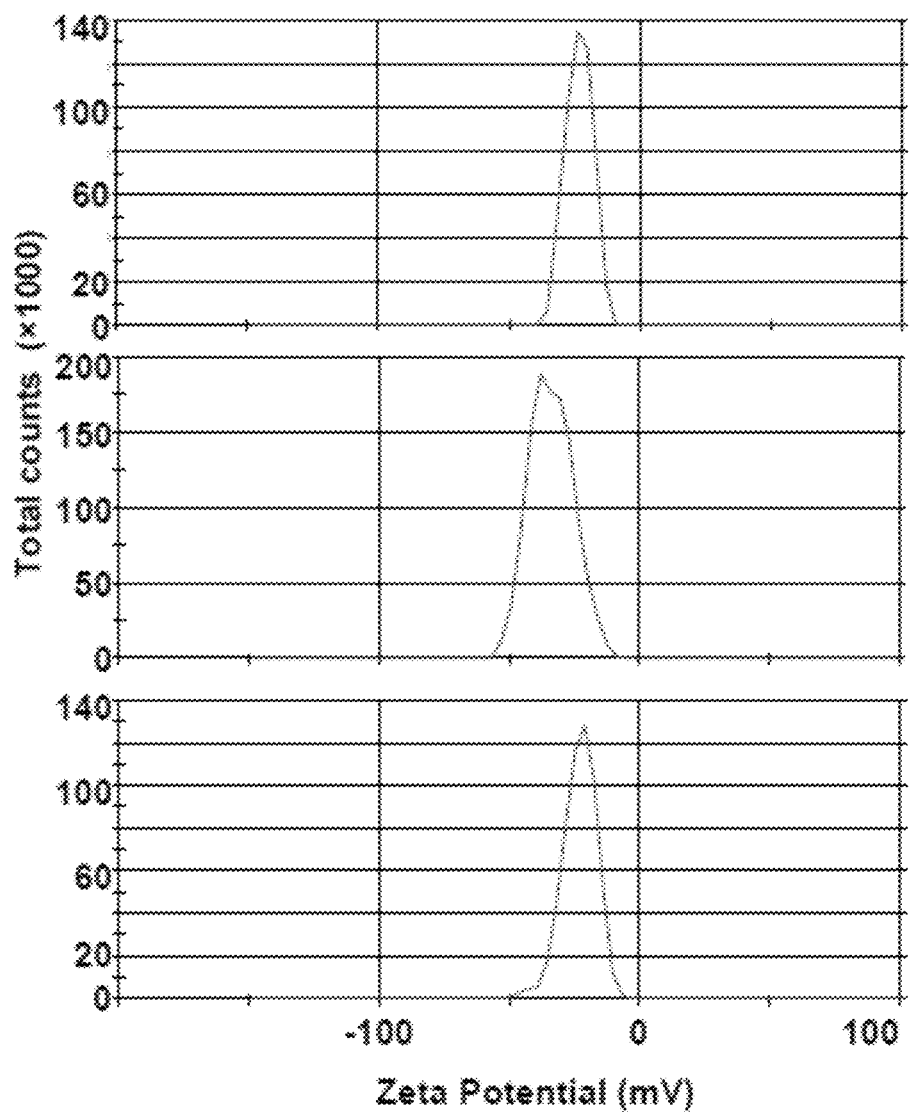

To test the stability of GDNs under physiological conditions, in vivo conditions were first mimicked by suspending GDNs in water, a 0.5N HCl solution, or a 0.5N NaOH solution, incubating the GDNs at 37° C. for 30 min, and then analyzing the change in GDN size and surface charge. The results (FIG. 1E) showed that GDNs were very stable at physiologic temperature (37° C.). Interestingly, compared to the size of GDNs in water, the heterogeneity of diameter of GDNs was reduced in an acidic solution, but no changes in an alkaline solution. The results suggested that the GDN surface at neutral pH or in an alkaline environment is negatively charged (FIG. 1F); whereas, in an acid environment, GDNs are weakly positive charged. The stability of GNDs was then evaluated after serial digestion in gastric and intestinal enzymatic solutions. Strikingly, as shown in FIG. 9, GDNs were highly resistant to the digestion by both gastric pepsin solution and intestinal pancreatin and bile extract solution.

Example 2—Toxicity of Orally Administrated GDNs

Figure 10A:
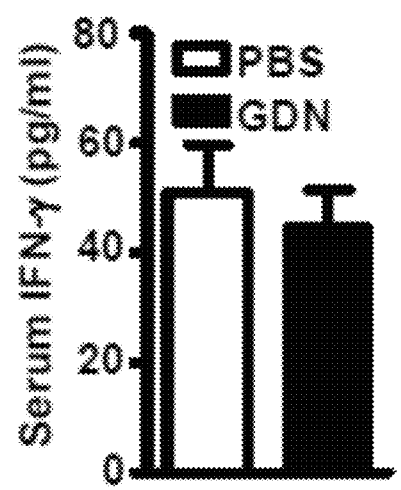
FIGS. 10A-10D include graphs and images showing that the oral administration of GDNs does not induce systemic toxicity and change intestinal morphology in mice that were gavaged with PBS or GDNs for 7 days, including: graphs showing the serum levels of IFN-γ (FIG. 10A), alanine aminotransferase (ALT) (FIG. 10B), and aspartate aminotransferase (AST) (FIG. 10C) measured after the last gavage; and images and graphs showing hematoxylin and eosin or Alcian blue and nuclear fast red stained slides of jejunum and colon that were examined for morphology (FIG. 10D).
Figure 10B:
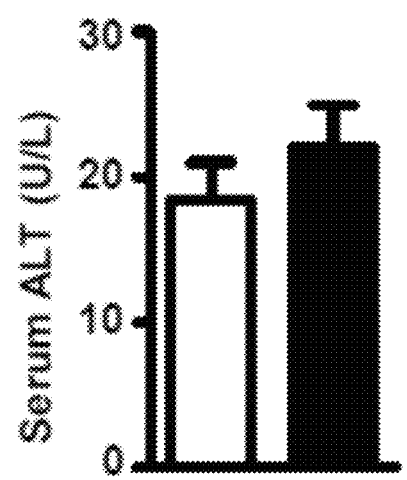
Figure 10C:
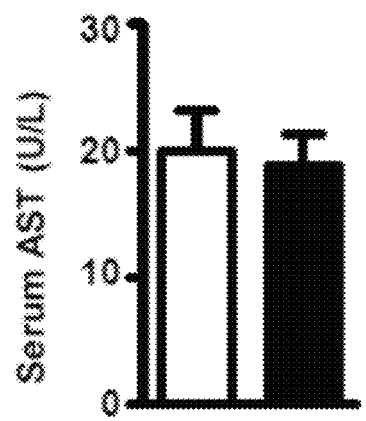
Figure 10D:
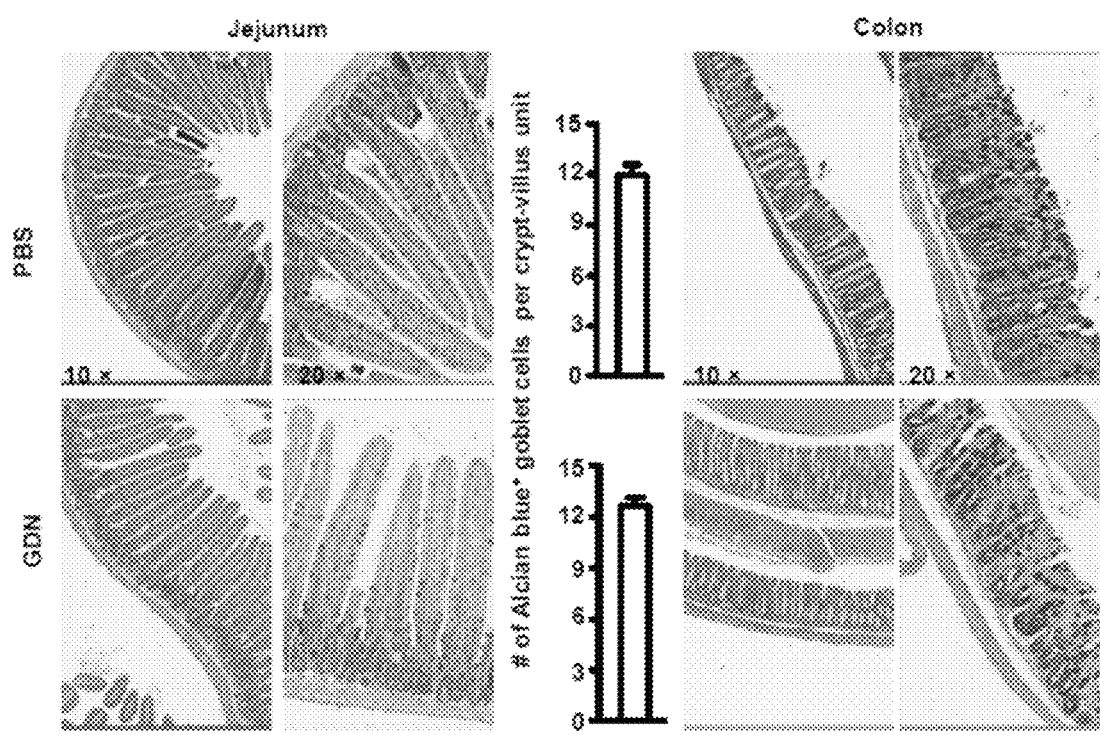
Figure 11A:
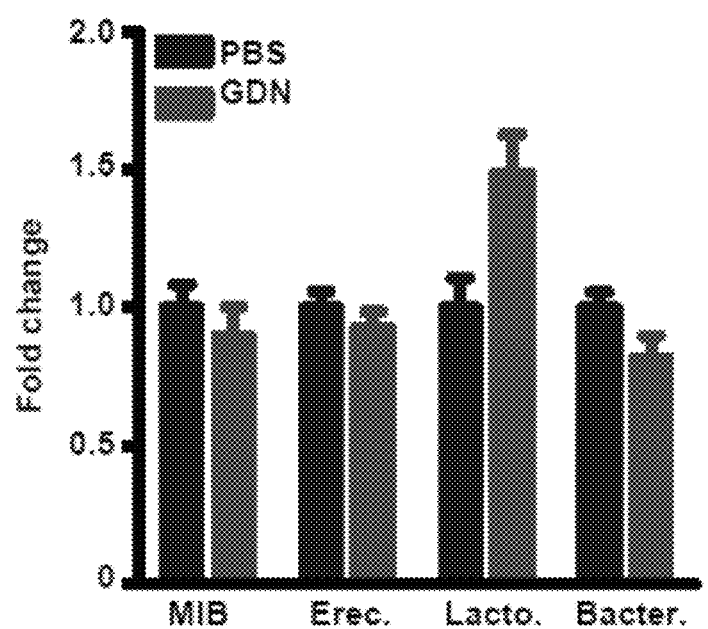
FIGS. 11A-11F are graphs showing that oral administration of GDNs does not alter the intestinal microenvironment during steady-state in mice gavaged with GDNs for 7 days, including: a graph showing 16S rDNA gene copies of different types of bacteria quantified by real-time PCR from stool pellets (FIG. 11A); a graph showing the frequency of γδ T cells in both intraepithelial lymphocytes (IEL) and lamina propria lymphocytes (LPL) of small intestine (FIG. 11B); graphs showing the percentage of CD11b$^+$Ly6C$^+$ monocytes (FIG. 11C), CD11b$^+$Ly6G$^+$ neutrophils (FIG. 11D), and Foxp3$^+$ regulatory T cells (FIG. 11E) in both small intestine (SI) and large intestine (LI), and the frequency of TNF-α secreting T cells in MLN as analyzed by FACS (FIG. 11F).
Figure 11B:
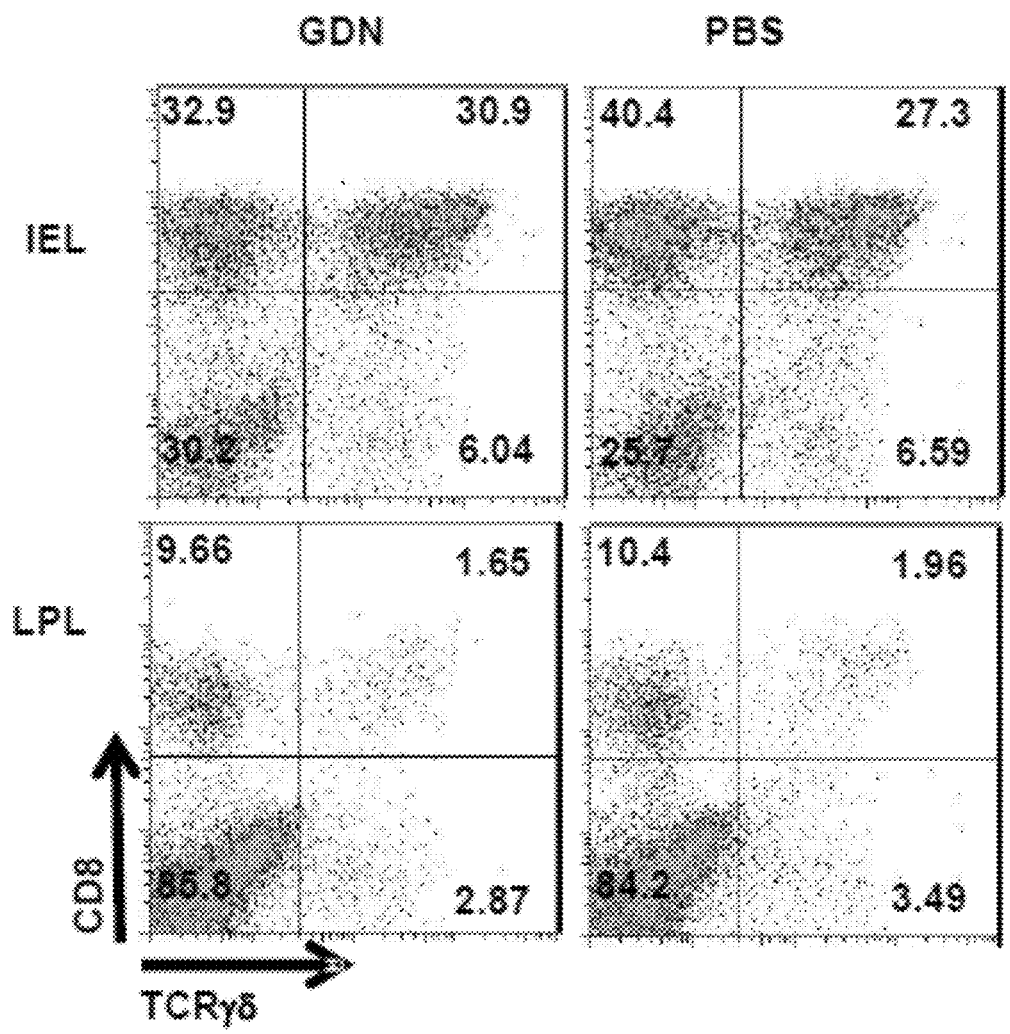
Figure 11C:
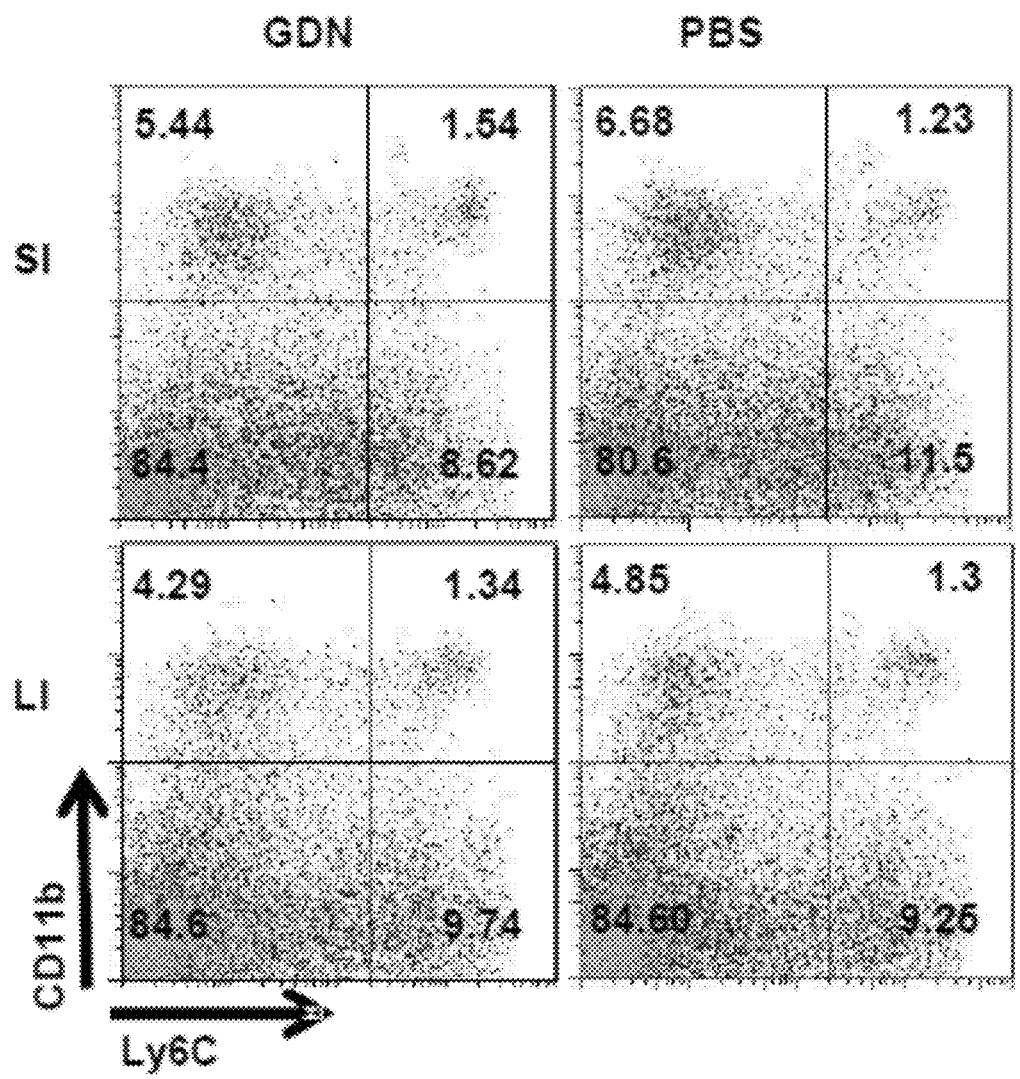
Figure 11D:
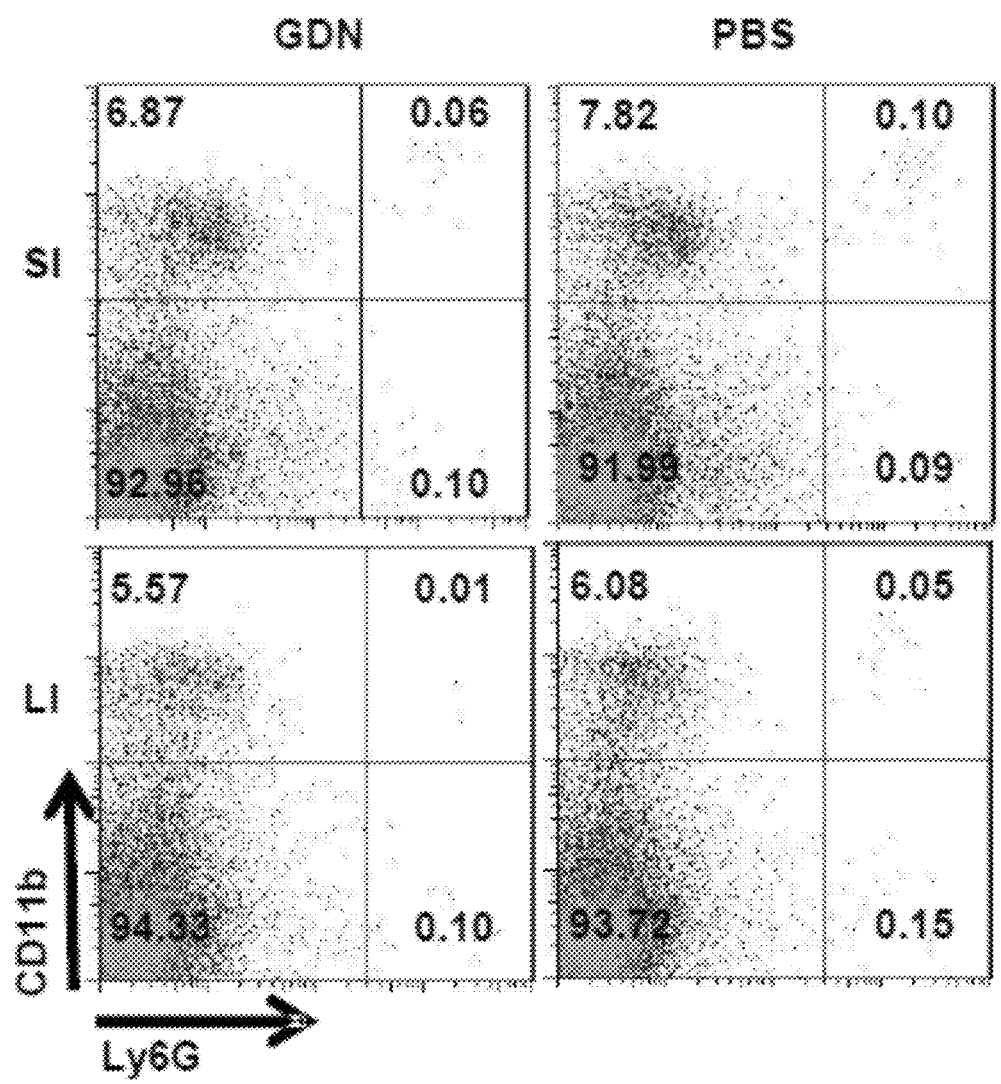
Figure 11E:
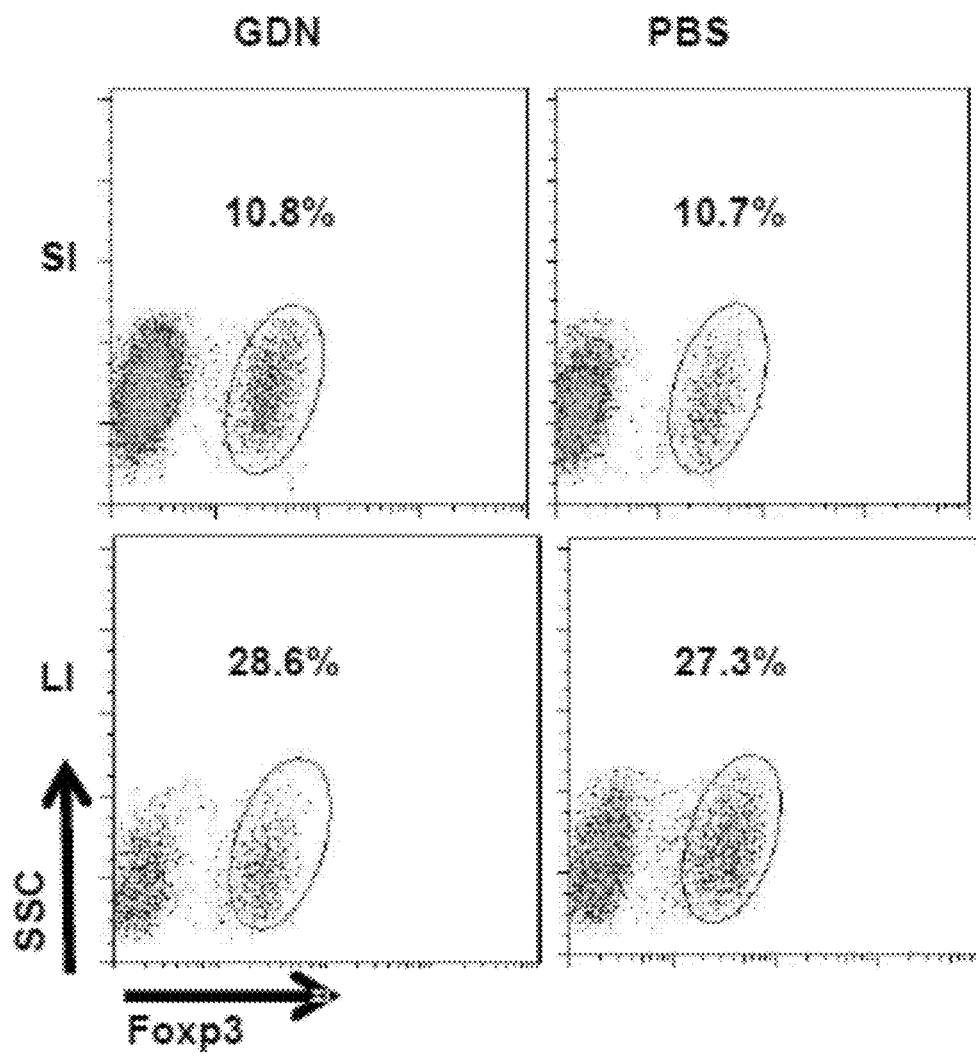
Figure 11F:
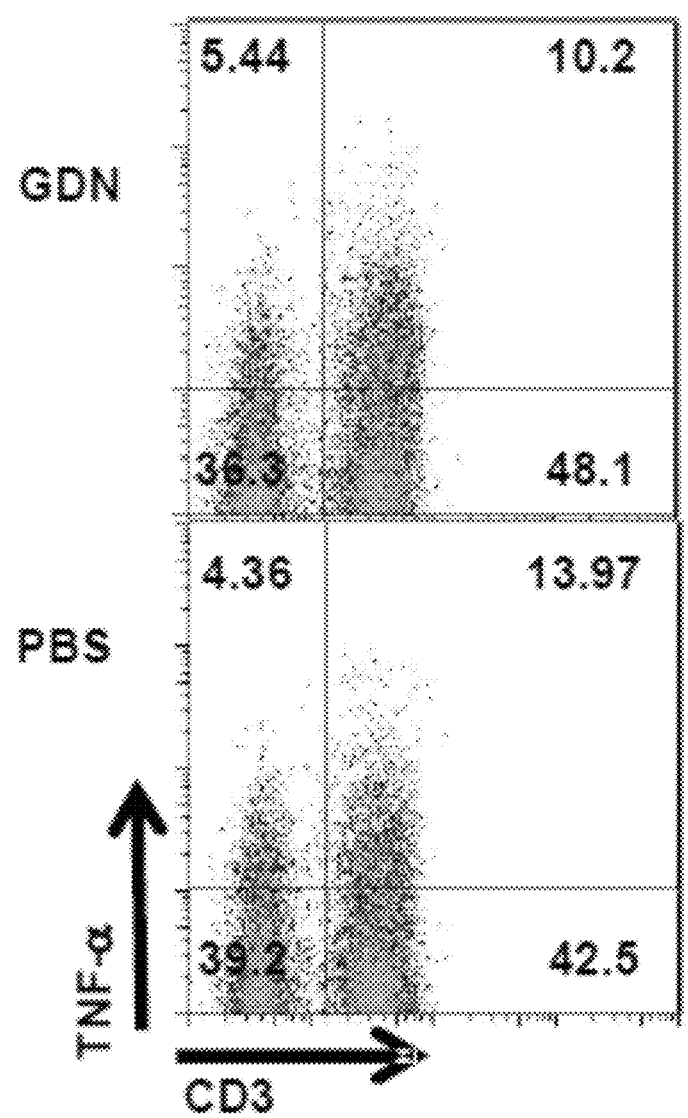

To evaluate the potential systemic toxicity of orally administrated GDNs, mice were daily given 10 mg/kg GDNs (the dose was pre-determined as the lowest dose with a protective effect in the colitis model) for 7 days and blood samples were collected 24 h after the last dose. Oral gavage of GDNs did not change the serum levels of IFN-γ and the liver enzymes, AST and ALT (FIGS. 10A-10C). No effects were detected on intestinal morphology or the number of alcian blue+ secretory goblet cells (FIG. 10D). The number of beneficial *Lactobacillus* bacteria tended to be higher in GDN-fed mice, yet not statistically significant when compared to mice fed PBS (FIG. 11A). In addition, GDN treatment did not alter the immune cell composition in the lamina propria (LP) (FIGS. 11B-11E) or the percentage of TNF-α producing cells in mesenteric lymph nodes (FIG. 11F). Moreover, the potential cytotoxicity of GDNs was directly evaluated in an in vitro cultured mouse macrophage cell line. The Annexin V/PI assay, which indicates cell apoptosis/necrosis, revealed that GDN exposure to concentrations up to 60 μg/ml did not increase the percentage of treated cell death (FIG. 12). Together, these data suggested that oral administration of edible nanovesicles from grapefruit had no observed side effects at the local or systemic level.

Figure 2A:
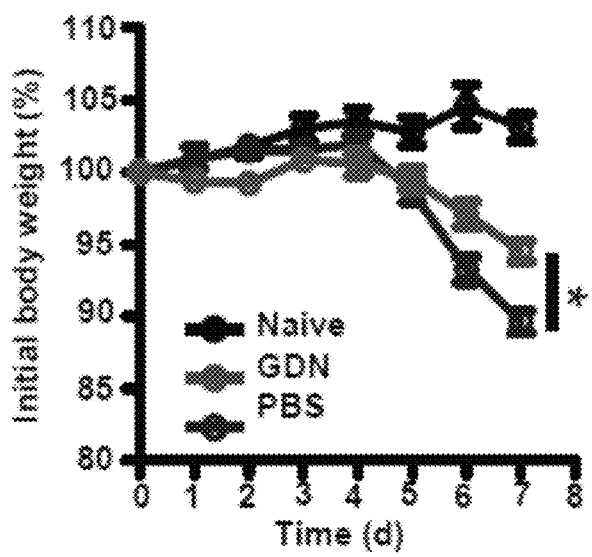
FIGS. 2A-2I include graphs and images showing that GDN pretreatment ameliorates dextran sulfate sodium (DSS)-induced colitis in C57/B6 mice treated with either PBS/DSS or GDN/DSS, including: a graph showing body weight (FIG. 2A, n=15); a graph showing colon length, where values are represented as percentage of untreated control mice and where colons were harvested on day 7 of DSS treatment (FIG. 2B, n=15); images showing histological analysis of the colons (FIG. 2C, n=15); a graph showing histological scoring as evaluated by the combined score of epithelial damage and extension of leukocyte infiltration (FIG. 2D, n=15); images showing immunofluorescent staining for E-cadherin of representative inflamed areas of colon, where the dotted line indicate basement membrane (FIG. 2E); graphs showing qPCR analysis of inflammatory cytokines and chemokines in harvested distal colons, where values are shown relative to the mRNA levels of naïve mice (FIG. 2F, n=15); and graphs showing FACS analysis where, on day 7 of DSS treatment, colons were harvested and digested, doublets were excluded from colonic digests on the basis of FSC-A and FSC-H, hematopoietic cells were gated on CD45.2 (FIG. 2G) and myeloid-derived cells were selected as CD11b$^+$, and where the resulting cells were then analyzed for Ly6C (FIG. 2H) or Ly6G (FIG. 2I) (n=15).
Figure 2B:
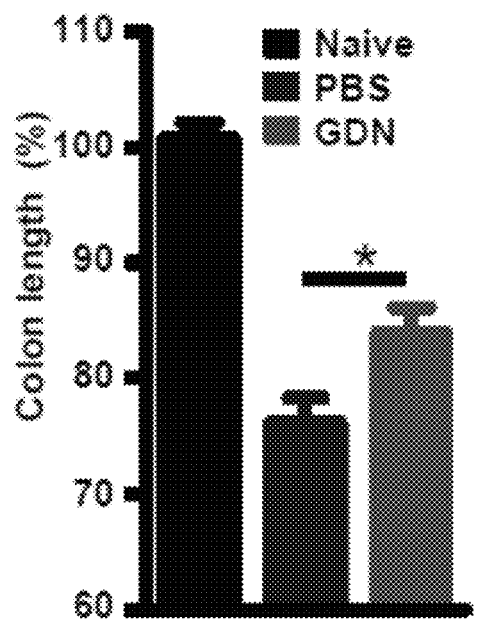
Figure 2C:
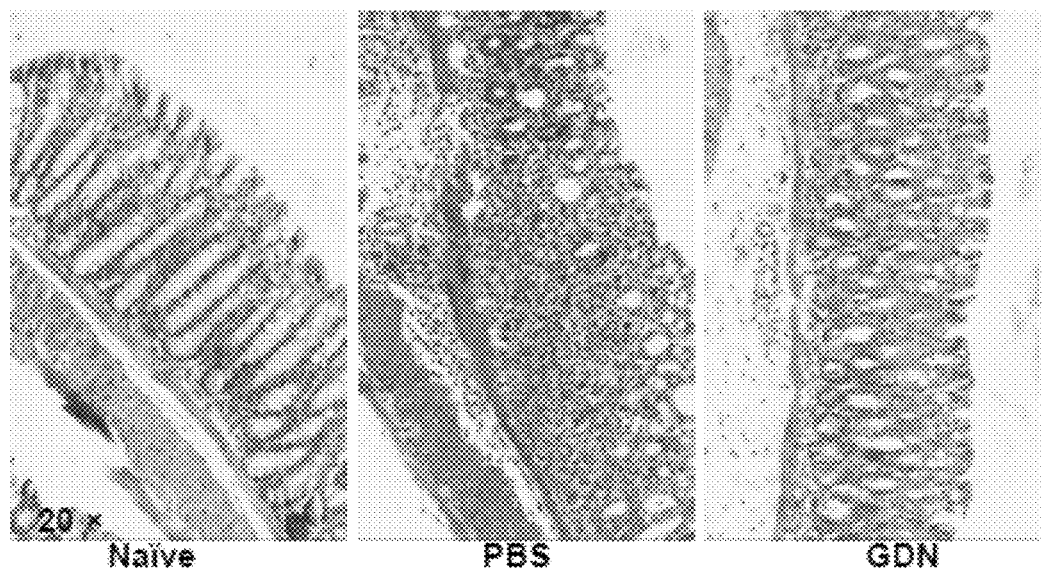
Figure 2D:
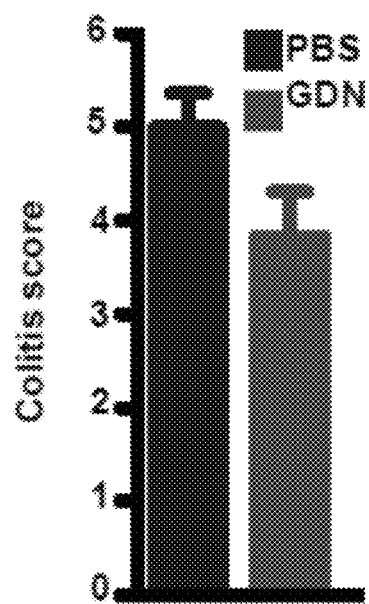

Example 3—GDN Pre-Treatment Increases the Resistance of Mice to DSS-Induced Colitis It is well documented that fruit is beneficial for human health and considered as a preventive medicine supplement. Pre-treatment with GDNs significantly increased the resistance of C57BL/6 mice to DSS-induced colitis, as evidenced by less weight loss and less colon shortening when compared to PBS treated mice (FIGS. 2A-2B). Histological analysis revealed a reduced severity of colitis in GDN-treated mice (FIG. 2C) and the colitis score was generally lower than that of PBS-treated mice (P=0.052, FIG. 2D). These data demonstrated a protective role of GDNs in DSS-induced colonic injury.

Figure 2E:
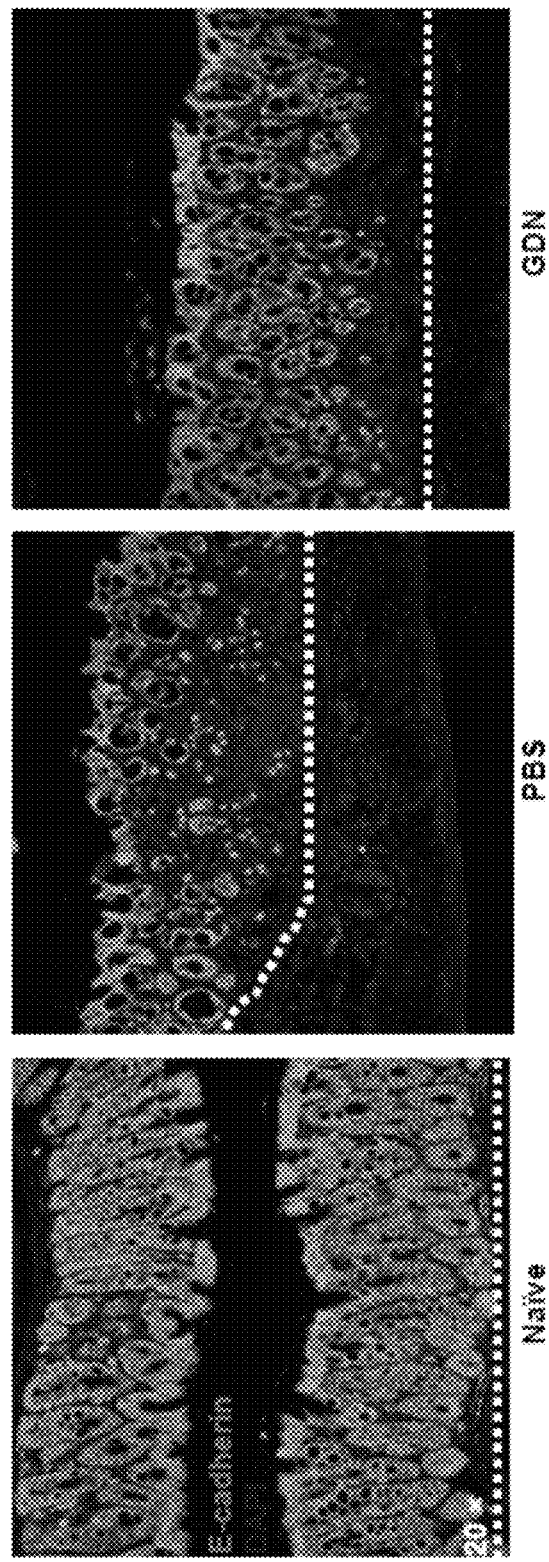
Figure 2F:
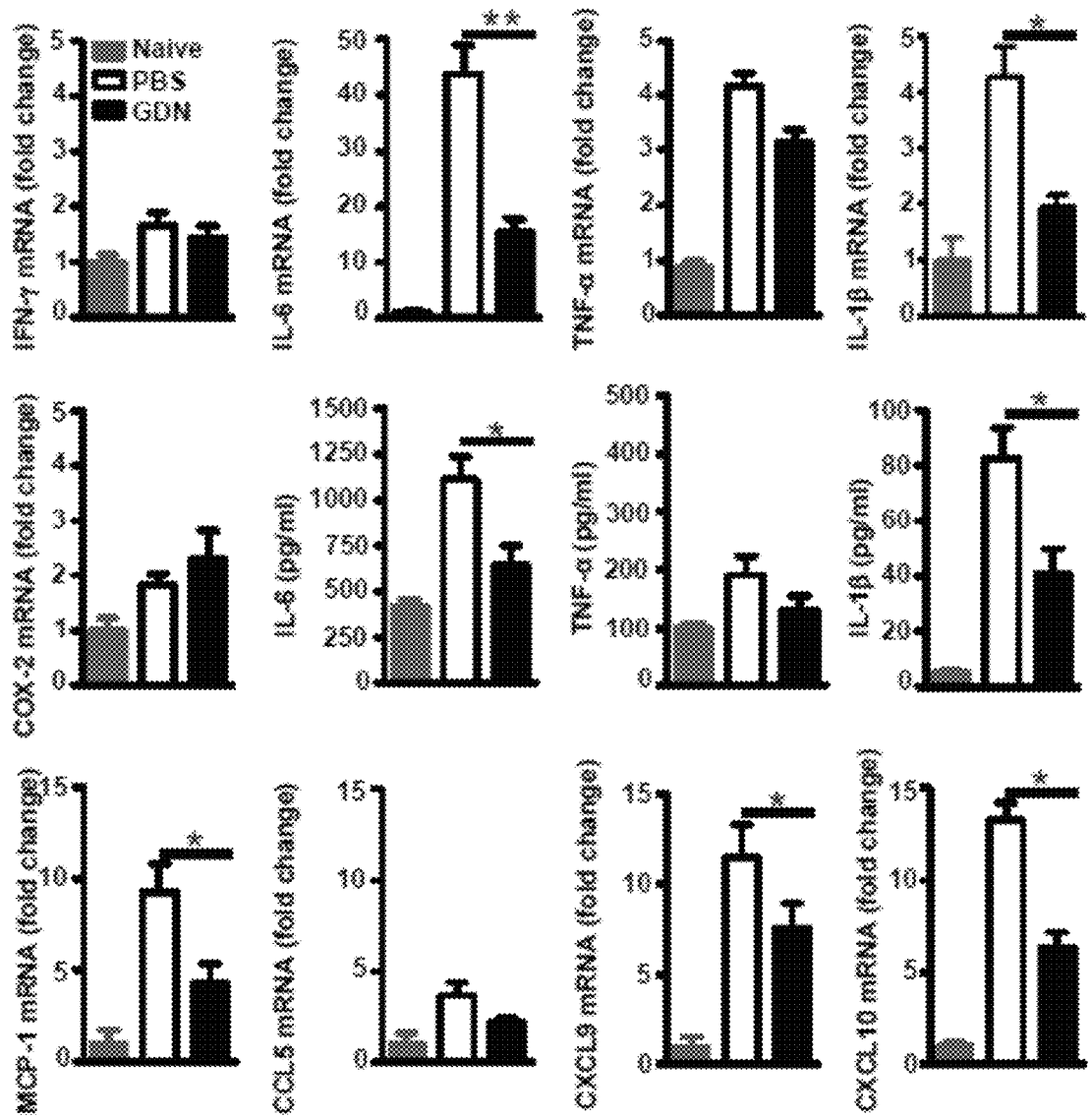
Figure 2G:
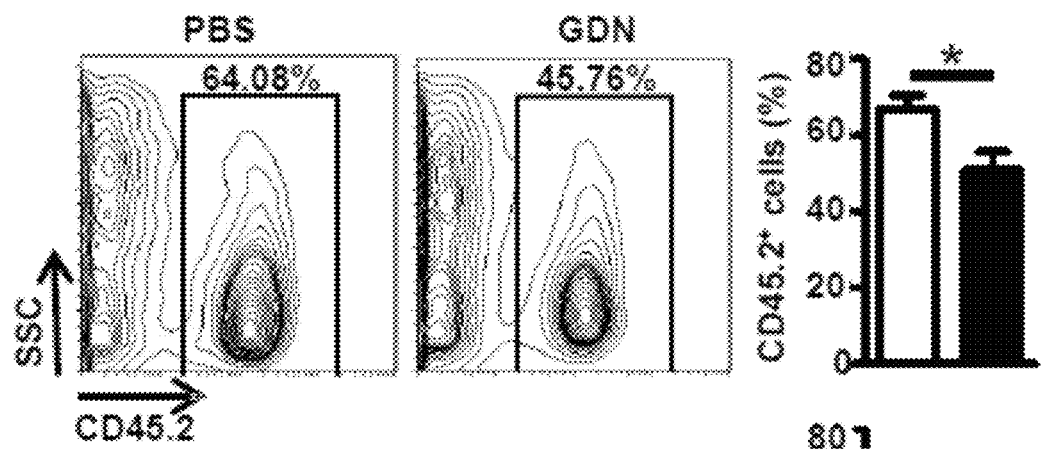
Figure 2H:
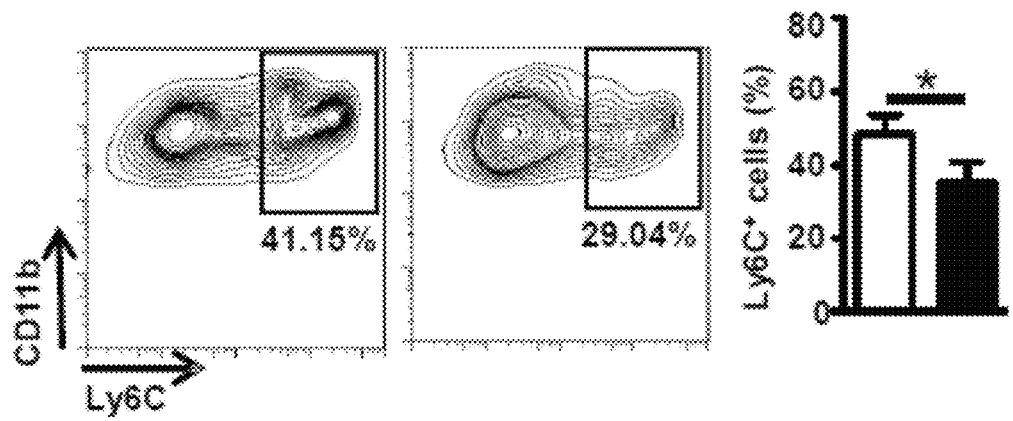
Figure 2I:
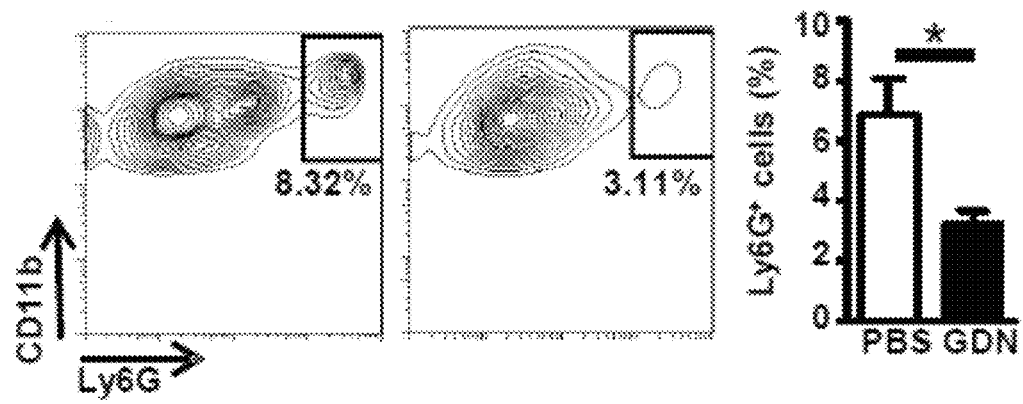

E-cadherin is a major component of adherent junctions. Impaired expression of E-cadherin has been linked to a disturbed intestinal barrier function and homeostasis. Immunofluorescence analysis revealed that in PBS/DSS treated mice, the expression of E-cadherin on colonic epithelial cells was dramatically reduced when compared to GDN/DSS treated mice (FIG. 2E). Prostaglandin $E_2$ ($PGE_2$) plays a critical role in the regeneration of the epithelial crypts after DSS-induced colitis. GDN treatment did not induce significant change in COX-2 expression (FIG. 2F) or $PGE_2$ production (FIG. 13). The induction of proinflammatory cytokines and chemokines plays a causative role in DSS induced colitis. The expression of IL-6 and IL-1β were reduced significantly in the colon of GDN/DSS-treated mice compared to those in the PBS/DSS group (FIG. 2F). The ELISA analysis results further confirmed that colons from GDN/DSS mice secreted significantly less IL-6 and IL-1β than PBS/DSS mice (IL-6: 641.99±75.36 vs. 1116.73±85.45 pg/ml, P<0.05; IL-1β: 41.15±6.15 vs. 82.77±7.75 pg/ml, P<0.05). Furthermore, the administration of GDNs resulted in significantly reduced mRNA levels of the chemokines MCP-1, CXCL9 and CXCL10, which are all known for playing an important role in the recruitment of inflammatory monocytes and T cells. FACS analysis of the infiltrating immune cells in lamina propria of colonic tissues revealed significant reduction of CD45.2 cells in GDN treated mice (50.72±4.20%) compared to the control group (67.03±3.27%) (FIG. 2G). Infiltration of CD11b+Ly6C$^{high}$ inflammatory neutrophils after GDN treatment were both reduced significantly (FIGS. 2H-2I). The fact that daily administration of GDNs attenuates DSS-induced colon inflammation suggested that GDNs can function as immunomodulators and enhance the anti-inflammation capacity of intestinal immune cells.

Example 3—Uptake of Orally-Delivered GDNs by Intestinal Macrophages

Figure 3A:
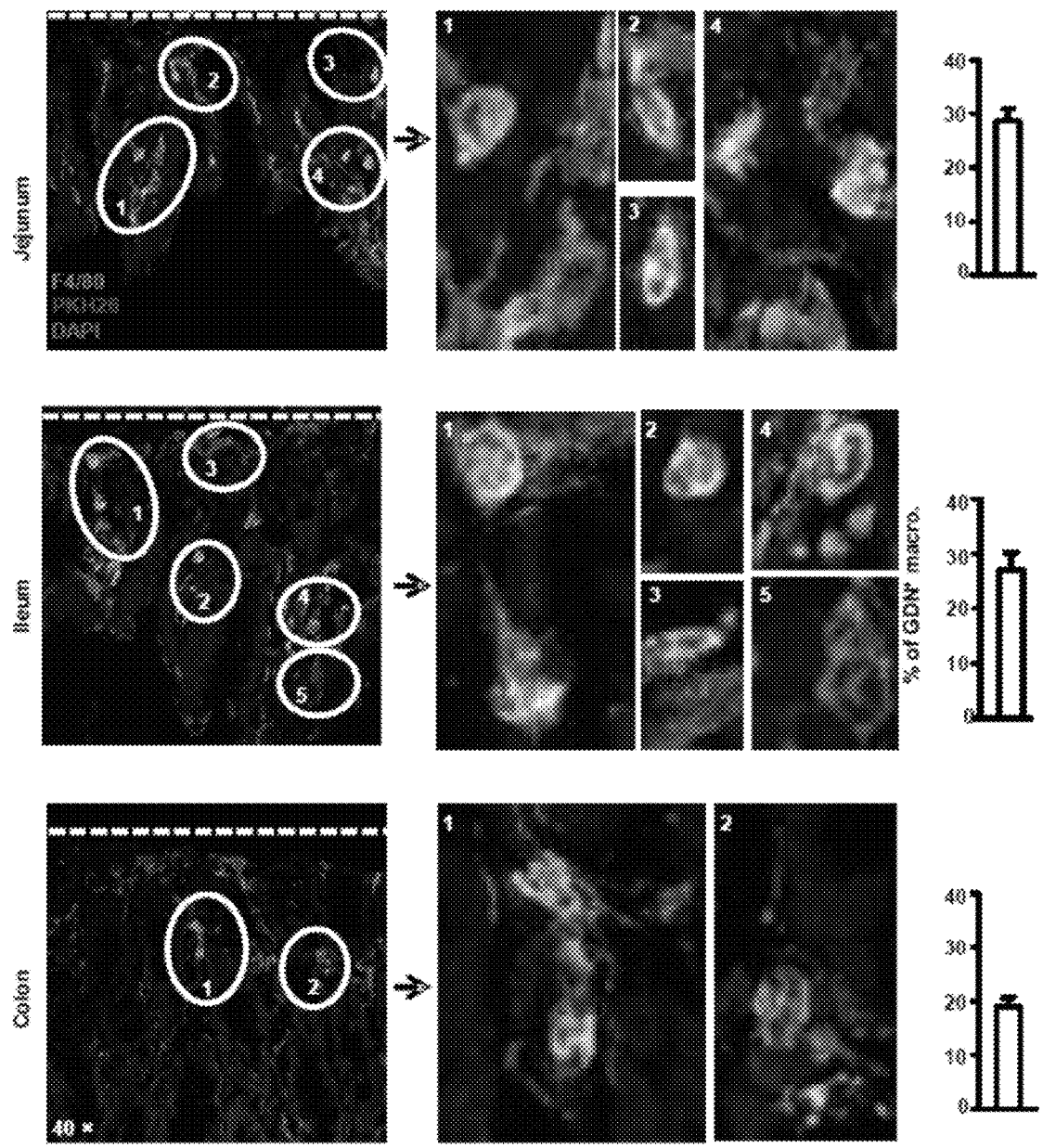
FIGS. 3A-3C include images and graphs showing that the majority of GDNs are taken up by intestinal and systemic macrophages including: images of sections of small intestine and colon (FIG. 3A); and images of Peyer's patches and MLN (FIG. 3B) and spleen and liver (FIG. 3C) revealing uptake of PKH-26 labeled GDNs specifically by F4/80$^+$ macrophages, where the percentage of macrophages that phagocytized GDNs is shown.
Figure 3B:
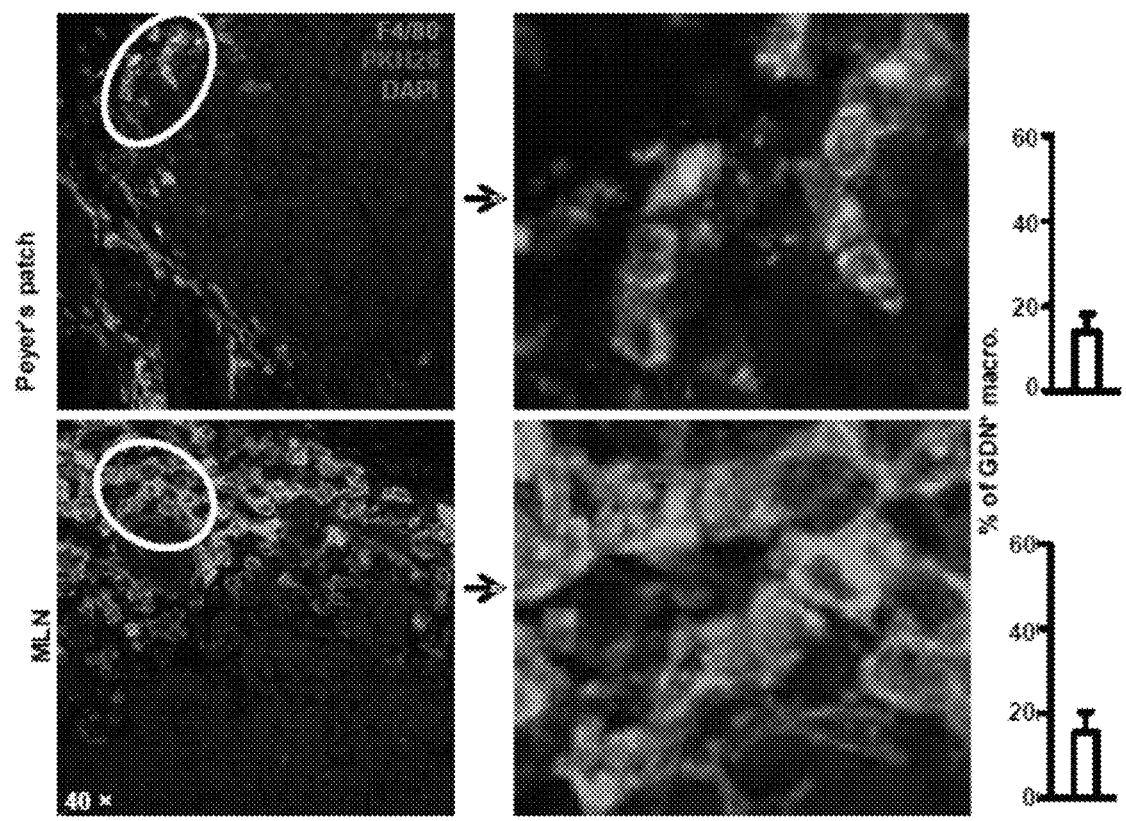
Figure 3C:
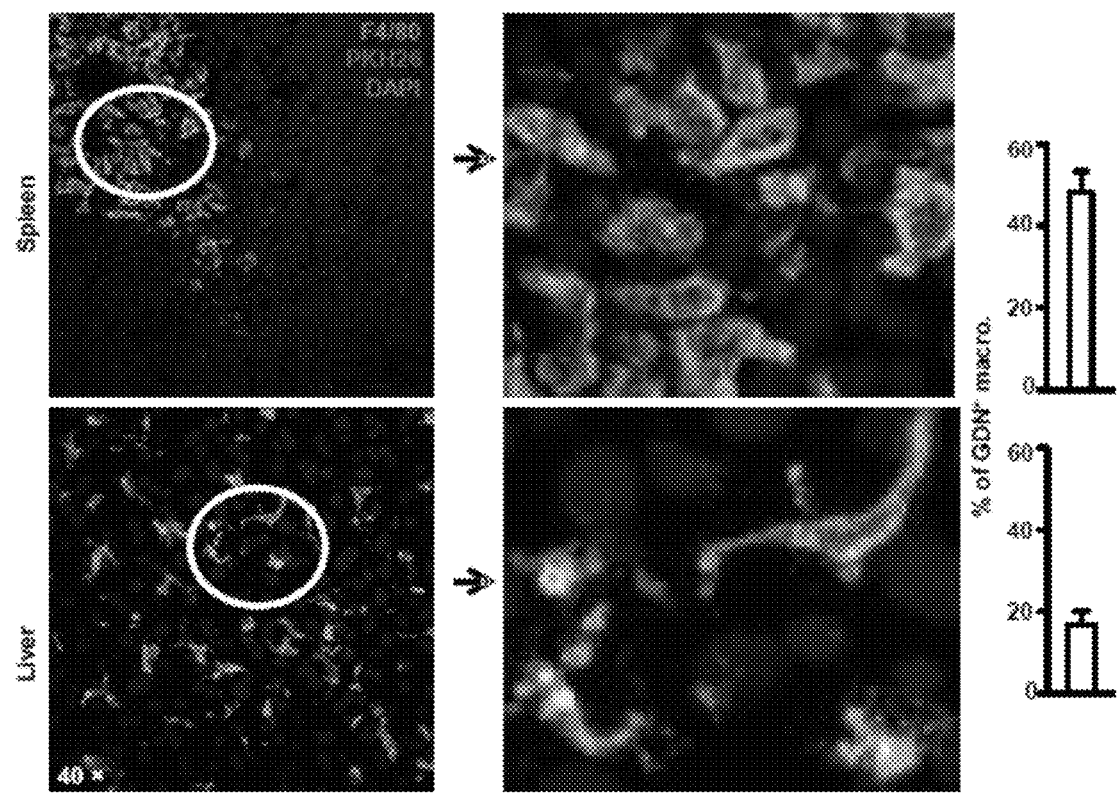
Figure 14:
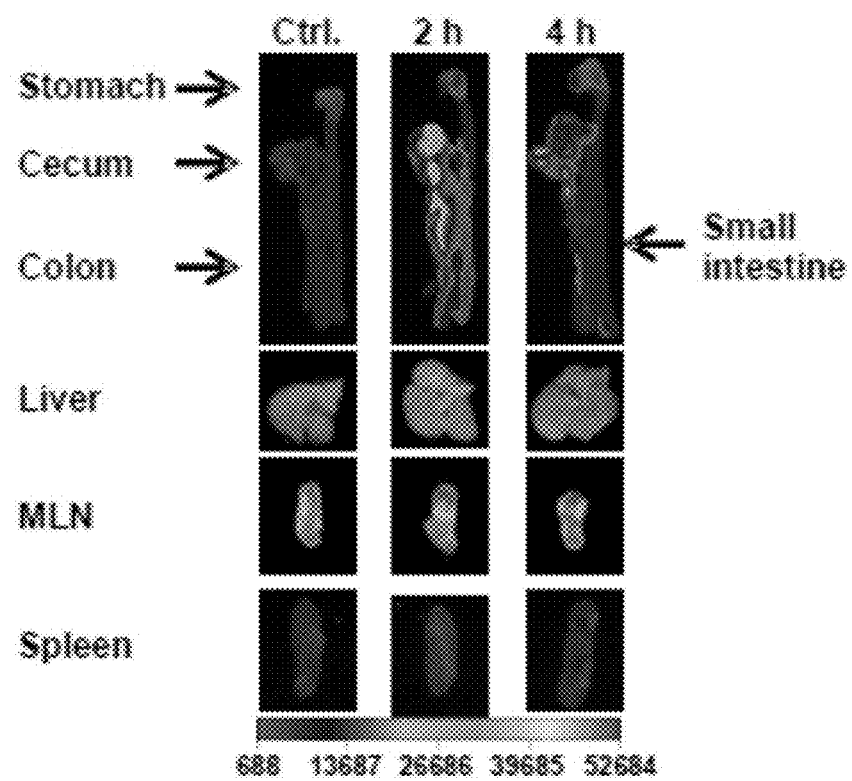
FIG. 14 includes images showing tissue biodistribution of orally administered GDNs, where mice fasted overnight were fed with DiR-labeled GDNs 2 h or 4 h before organs were harvested, and where the biodistribution of DiR-labeled GDNs was imaged with Kodak Image Station 4000MM Pro system.
Figure 15:
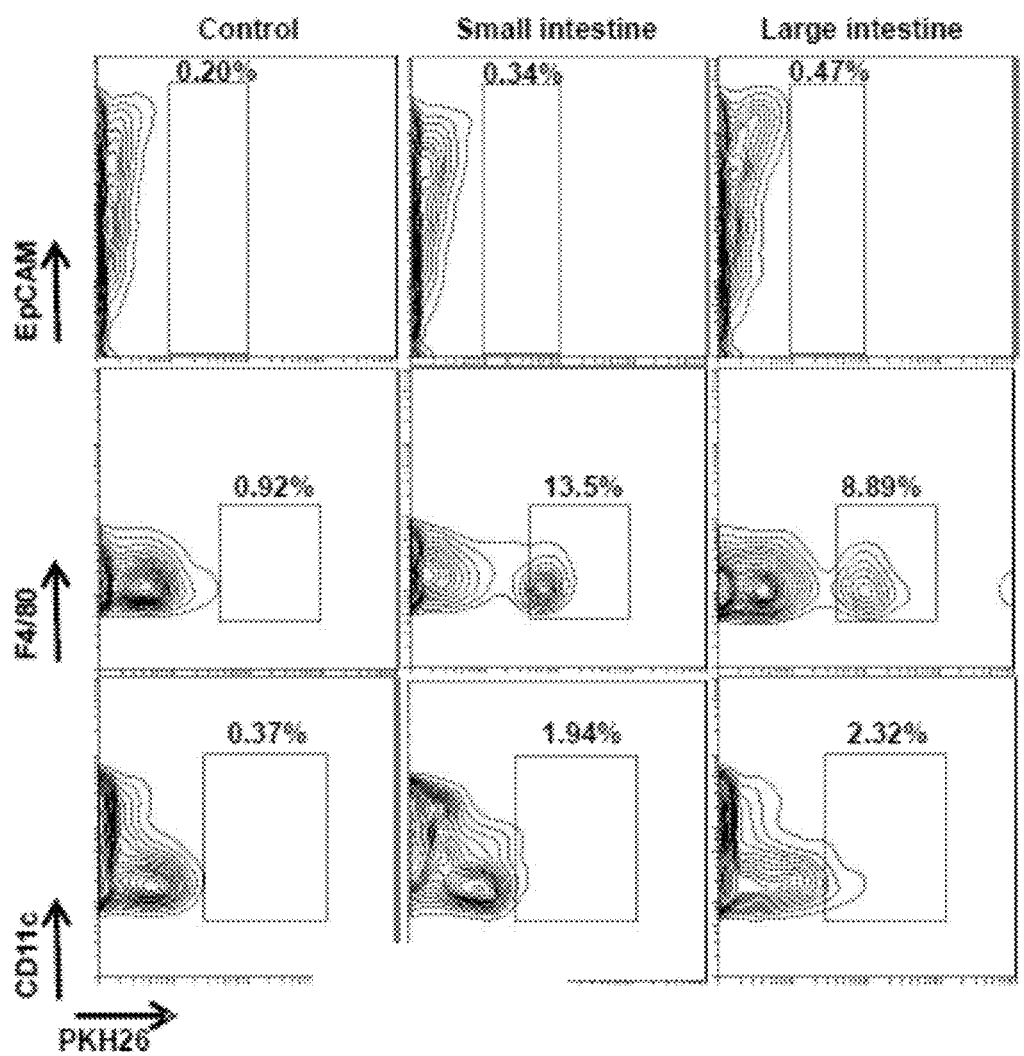
FIG. 15 includes graphs showing that intestinal macrophages are the major targets of orally administered GDNs, where mice fasted overnight were fed with PKH26-labeled GDNs 2 h and 4 h before harvesting the intestine, where intestinal epithelial cells were isolated and stained for EpCAM, and where lamina propria myeloid-derived cells were gated on CD11b and then further analyzed on F4/80 or CD11c.

GDNs biodistribution and cellular target was next determined after oral administration. Near-infrared imaging showed that DiR-labeled GDNs rapidly passed through the stomach, proximal small intestine and accumulated at the middle and distal part of small intestine, cecum and colon. By four hours post oral administration, large amounts of DiR-labeled GDNs were still visible in the large intestine (FIG. 14). Confocal analysis of tissue sections revealed that the majority of GDNs were colocalized with F4/80+ macrophages in the lamina propria of both small and large intestine (FIG. 3A). The 3D image constructed from z-series stacks indicated that GDNs were internalized by macrophages. Intestinal macrophages were further confirmed by FACS analysis as the major target of orally given GDNs (FIG. 15). The difference in percentage of PKH26$^+$ macrophages detected by confocal microscopy compared to FACS may be due to the difference in tissue processing, staining and sensitivity. Surprisingly, PKH26$^+$ macrophages were also readily detected in Peyer's patches, MLN, spleen, and liver (FIGS. 3B-3C).

Figure 4A:
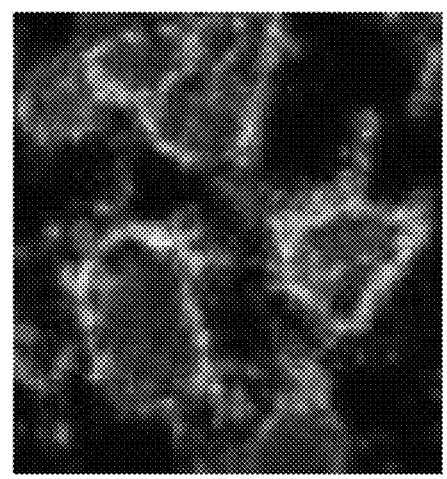
FIGS. 4A-4B include images and a graph showing that GDNs utilize both micropinocytosis and a clathrin-dependent uptake mechanism for entry into macrophages, including: an image showing the uptake of GDNs by Raw264.7 macrophages (FIG. 4A); an image showing Raw 264.7 macrophages that were pretreated with 50 μM amiloride (Amil.), 12.5 μM chlorpromazine (Chlor.) or 100 μM of indomethacin (Indo.) for 30 min and then incubated with 2 μg/ml PKH26-labeled GDNs for 3 h and subsequently cell surface stained with F4/80 antibody to exclude membrane contamination (FIG. 4B); and a graph showing the percentage of GDN uptake relative to control (FIG. 4C).
Figure 4B:
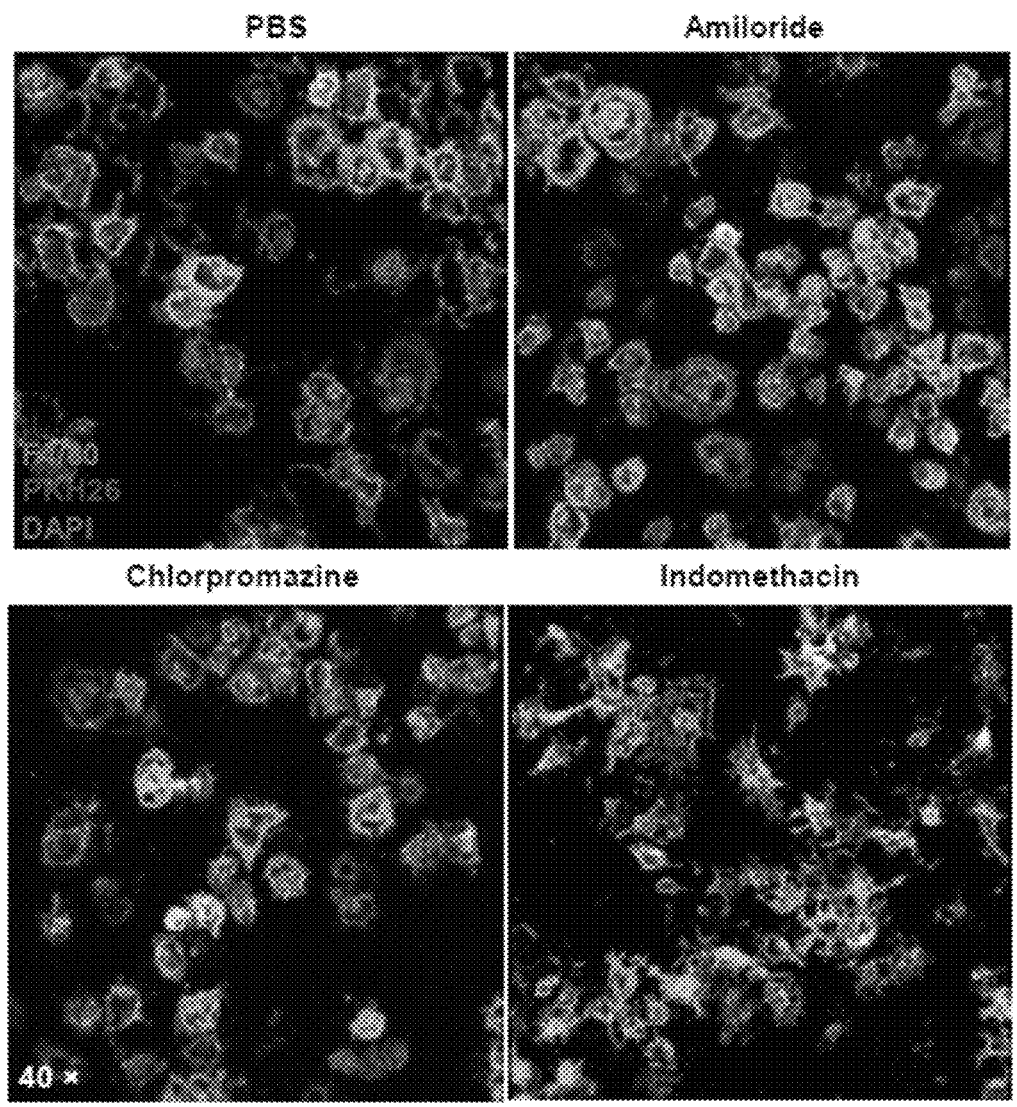
Figure 4C:
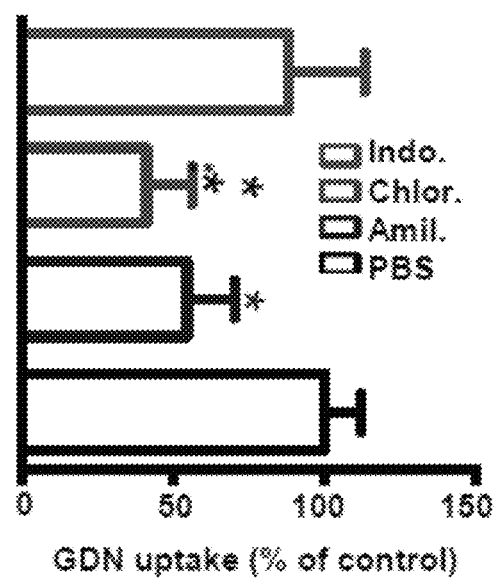

There are multiple pathways for internalization of particles, including phagocytosis, macropinocytosis, clathrin-mediated and caveolae-mediated endocytosis. To delineate the role of specific endocytosis pathways involved in GDN cellular internalization, a series of GDN uptake assays were performed in the presence of biochemical inhibitors to block specific pathways. Confocal analysis showed that the vesicles accumulated in the perinuclear region of the cells (FIG. 4A). Amiloride inhibits the process of macropinocytosis, GDN uptake was inhibited by 45.48±15.64% (FIGS. 4B-4C). Chlorpromazine inhibits clathrin-mediated endocytosis, which reduced the GDN uptake by 58.98±15.21%. Treatment of cells with indomethacin, an inhibitor of caveolae-mediated endocytosis did not significantly alter GDN uptake (FIGS. 4B-4C). These results indicated that GDNs were internalized via both macropinocytosis and clathrin-dependent pathways.

Example 4—GDNs Enhance the Anti-Inflammatory Capacity of Intestinal Macrophages

Figure 5A:
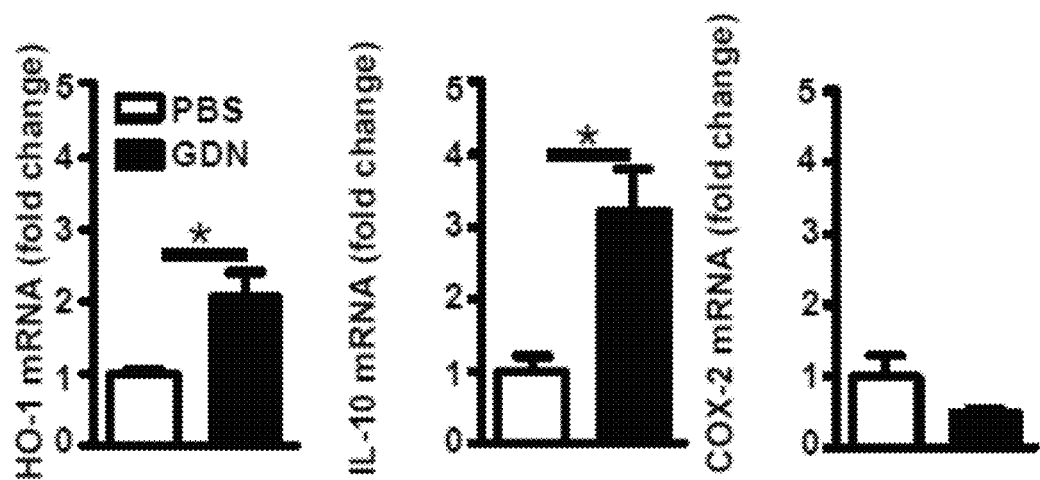
FIGS. 5A-5F include graphs and images showing that GDNs enhance the anti-inflammatory capacity of resident intestinal macrophages isolated from colons of B6 mice and treated with PBS or GDNs for 7 days, including: a graph showing the expression of HO-1, IL-10 and COX-2 as analyzed by real-time RT-PCR (FIG. 5A); an image showing the up-regulation of HO-1 expression by GDNs as confirmed by western blot (FIG. 5B); a graph showing amounts of IL-10 and TNF-α as measured by ELISA in the culture supernatants of isolated macrophages stimulated with heat-killed *E. coli* (MOI=50) for 24 h with 2 μg/ml of GDNs in the GDN treated group (FIG. 5C); representative images of a colon from mice orally given 2% DSS for 5 days, fasted overnight, and then gavaged twice with 30 mg/kg of PKH26 labeled GDNs 2 h and 4 h before harvesting, where confocal images showed the uptake of PKH26 labeled GDNs by F4/80$^+$ macrophages, where nuclei were labeled with DAPI, and where the dotted line indicates basement membrane (FIG. 5D); a graph showing the percentage of macrophages that phagocytized GDNs (FIG. 5E); and graphs showing the amounts of TNF-α, IL-1β, IL-6 and IL-10 as measured by ELISA in the culture supernatants of cultures of colonic macrophages that were isolated from mice pretreated with GDNs for 7 days and then given 2% DSS for 5 days with continued GDN administration and that were then incubated with GDNs for 36 hours (FIG. 5F).
Figure 5B:
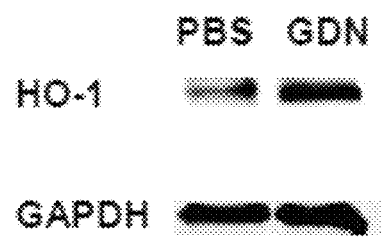
Figure 5C:
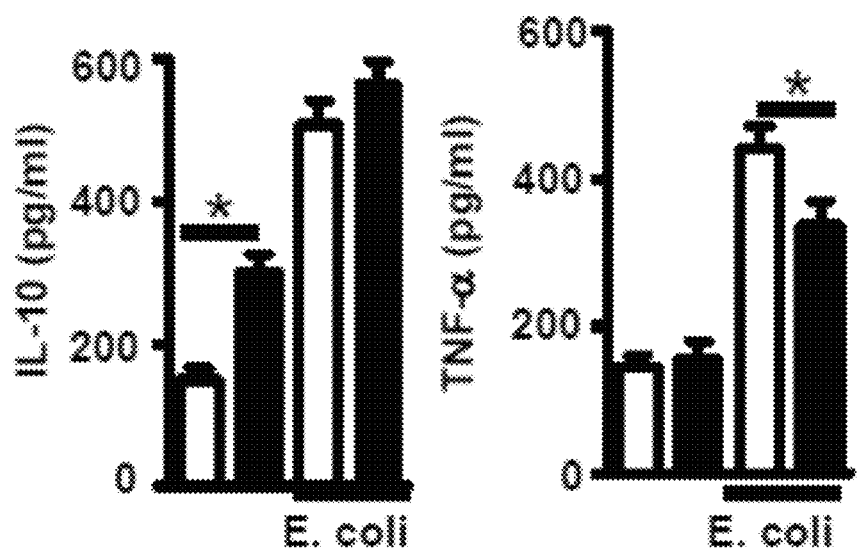
Figure 5D:
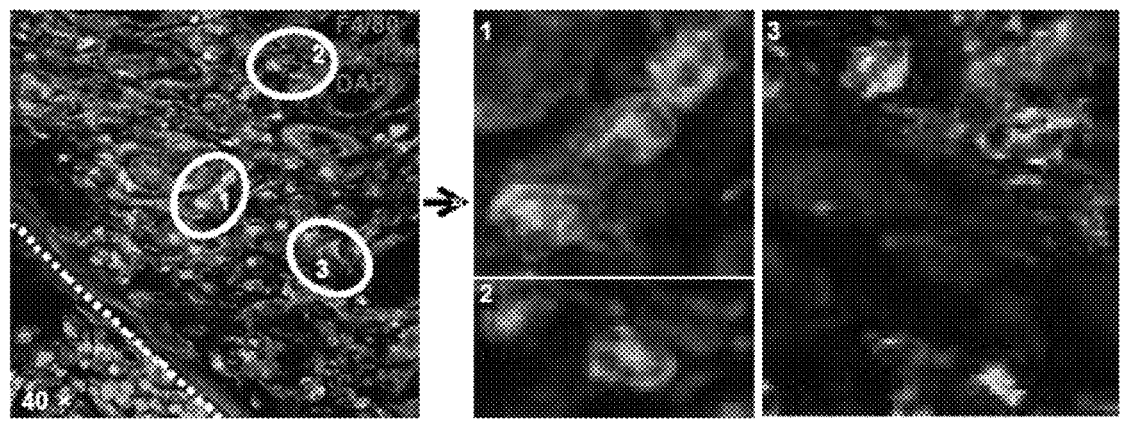

HO-1 and IL-10, expressed in macrophages, play a role in preventing colitis with their potent anti-inflammatory capacity. Colonic macrophages (CD11b$^+$F4/80$^+$ lamina propria macrophages, LPMs) isolated from mice pre-fed with GDNs for one week showed significantly enhanced HO-1 (2.06±0.35, P<0.05) and IL-10 expression (3.22±0.58, P<0.05) (FIG. 5$a$), and the augmented expression of HO-1 and IL-10 was further confirmed by western blot and ELISA, respectively (FIGS. 5B-5C).

Figure 5E:
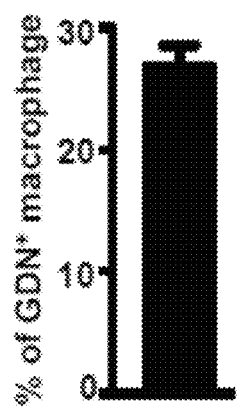
Figure 5F:
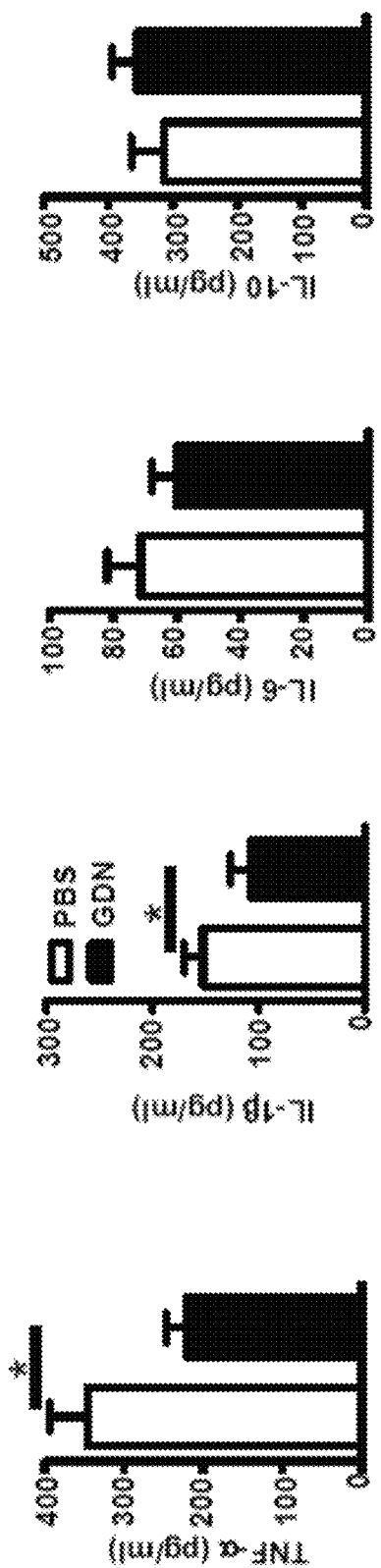

To determine whether this enhanced expression of HO-1 and Il-10 inhibited the sequential activation of LPMs, LPMs were isolated from mice pre-fed with GDNs, were stimulated with heat-killed $E. coli$ for 24 h, and the secretion of IL-10 and TNF-α was then measured in culture supernatants. In response to stimulation with $E. coli$, LPMs produced large amounts of IL-10 and the addition of GDNs did not further increase IL-10 secretion. However, GDN pre-treatment significantly inhibited the production of the pro-inflammatory cytokine TNF-α (FIG. 5C). Next, it was tested whether a reduction of TNF-α also took place in the DSS induced colitis mouse model. On day 5 after DSS-treatments, the number of F4/80$^+$ cells was increased dramatically (FIG. 5D) and GDNs were taken up by around 30% of the colonic F4/80$^+$ cells (FIG. 5E). Colonic macrophages were isolated and the production of pro-inflammatory cytokines was measured by ELISA. Macrophages isolated from inflamed colon produced large amounts of TNF-α (346.45±36.66 pg/ml), IL-1β (152.48±13.62 pg/ml), IL-10 (314.67±37.94 pg/ml) and to a lesser degree IL-6 (FIG. 5F). In contrast, colonic macrophages from GDN-treated mice secreted significantly less TNF-α (221.63±19.80 pg/ml, P=0.045) and IL-1β (107.95±14.67 pg/ml, P=0.021). These results suggested that the protective effect of GDNs in experimental colitis may be through induction of HO-1 and IL-10 expression in colonic macrophages, which in turn inhibits the secretion of the inflammatory cytokines IL-1β and TNF-α.

Figure 6A:
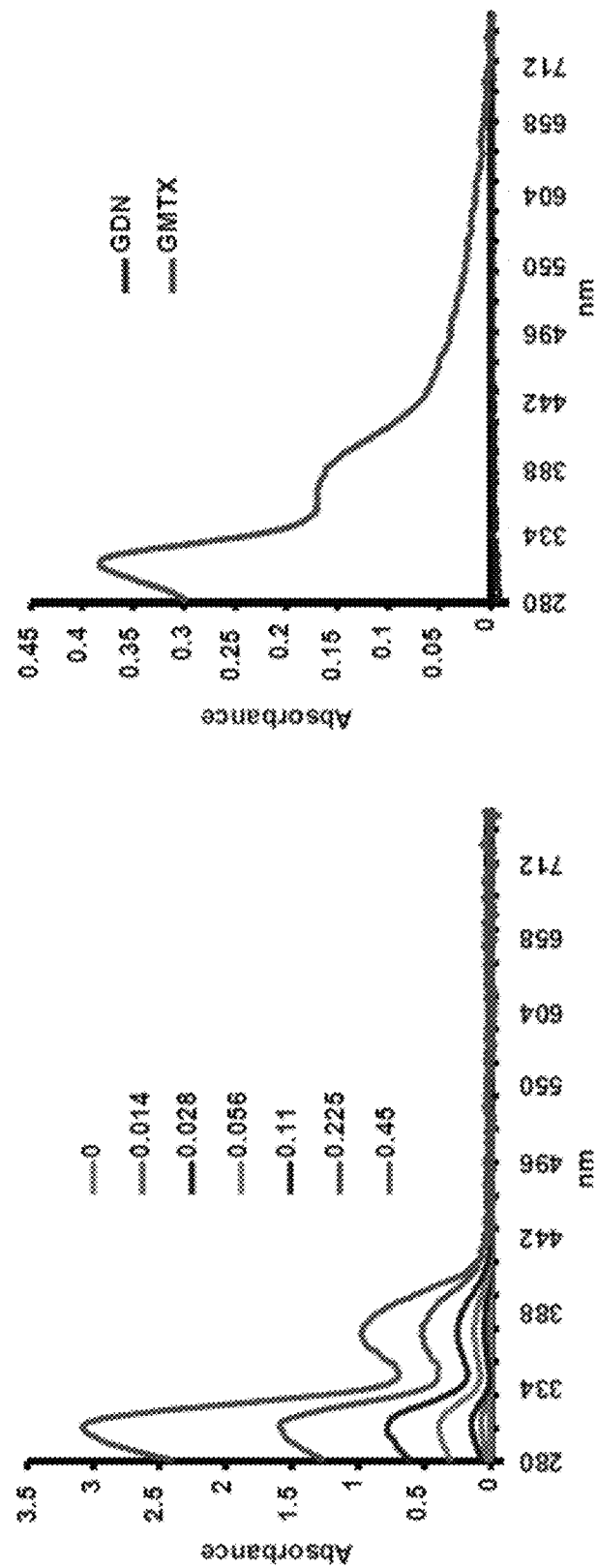
FIGS. 6A-6E include graphs and images showing the preparation and characterization of GDN-methotrexate (MTX) conjugates (GMTX), including: graphs showing the UV spectra of standard free MTX (mg/ml) and GMTX (FIG. 6A); graphs showing the size and surface charge of GMTX as measured using a Zetasizer (FIG. 6B); graphs showing the comparative anti-proliferative effect of GMTX vs. free MTX on a mouse macrophage cell line, where the bold numbers within each histogram represent the percentage of cells containing CFSE (FIG. 6C); confocal images showing the uptake of PKH26 labeled GMTX by F4/80$^+$ macrophages, where nuclei were labeled with DAPI, where the original magnification was 40× (left panel) with enlargement of the indicated area shown in the right panel, and where the dotted line indicates basement membrane (FIG. 6D); and a graph showing the percentage of macrophages that phagocytized GMTXs (FIG. 6E).
Figure 6B:
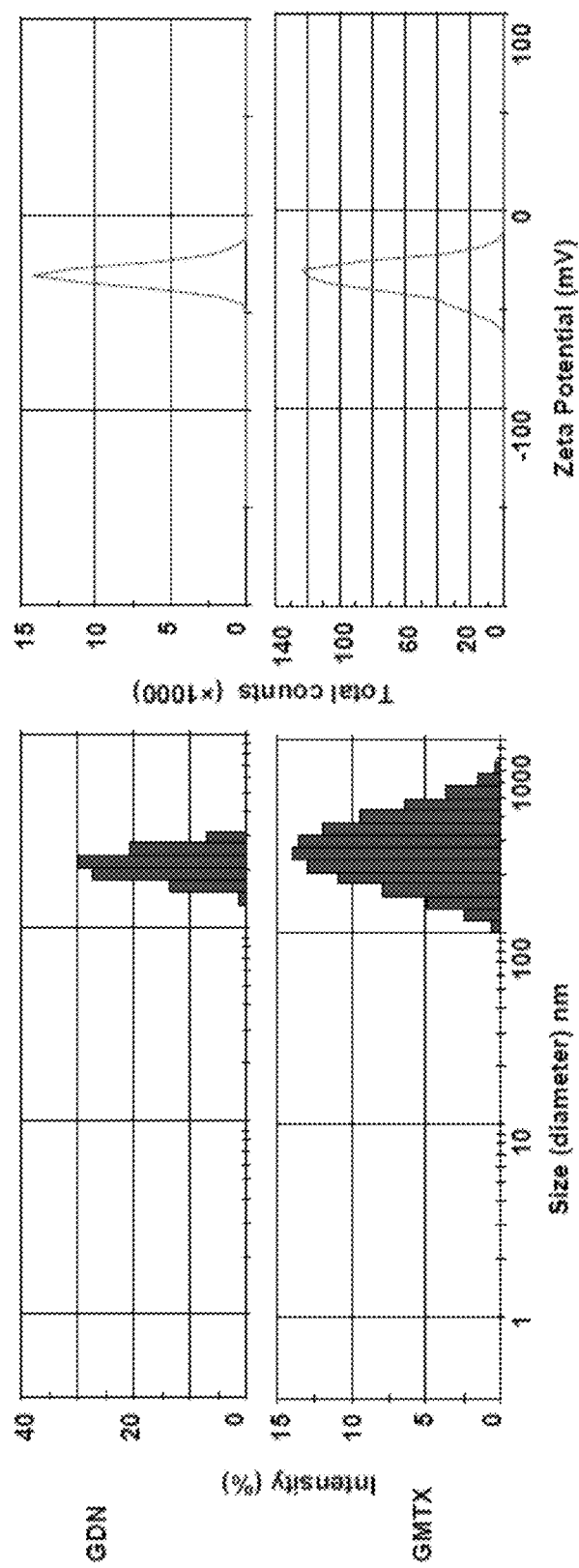
Figure 6C:
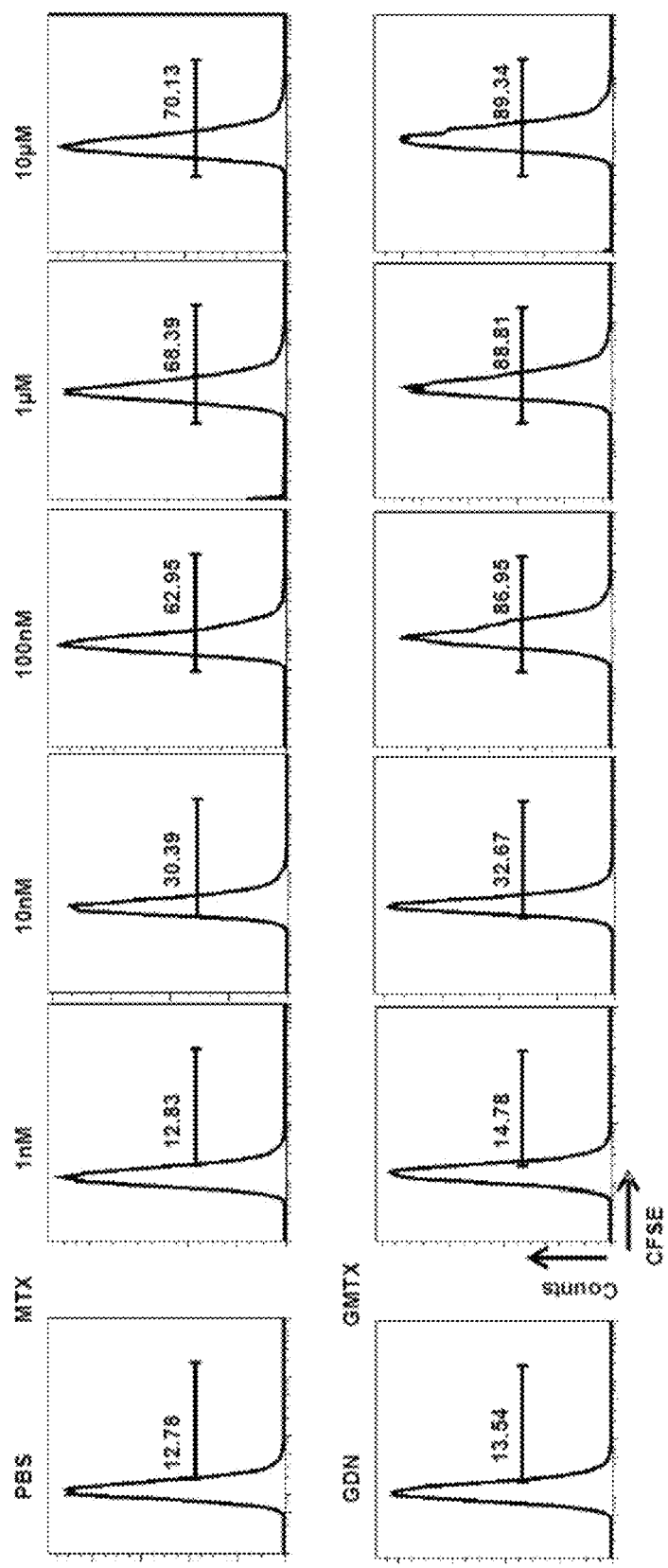
Figure 6D:
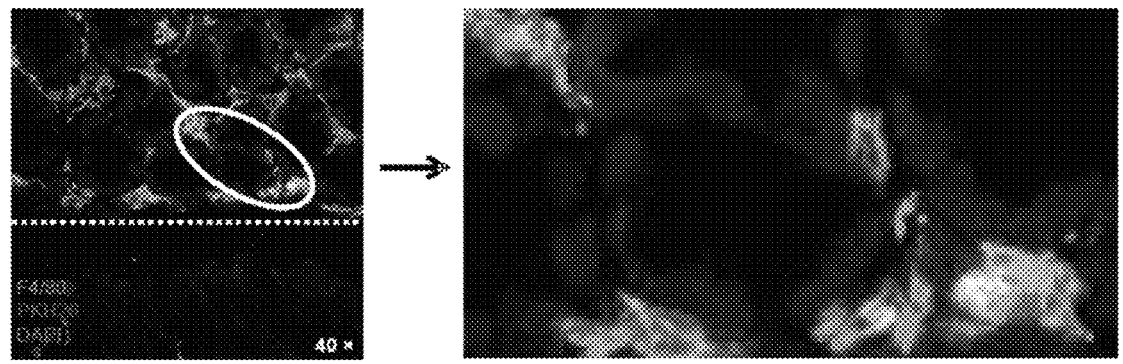
Figure 6E:
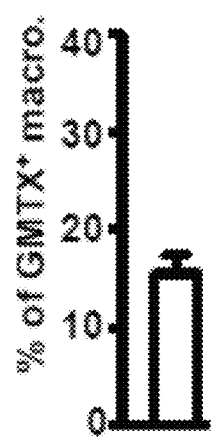
Figure 16:
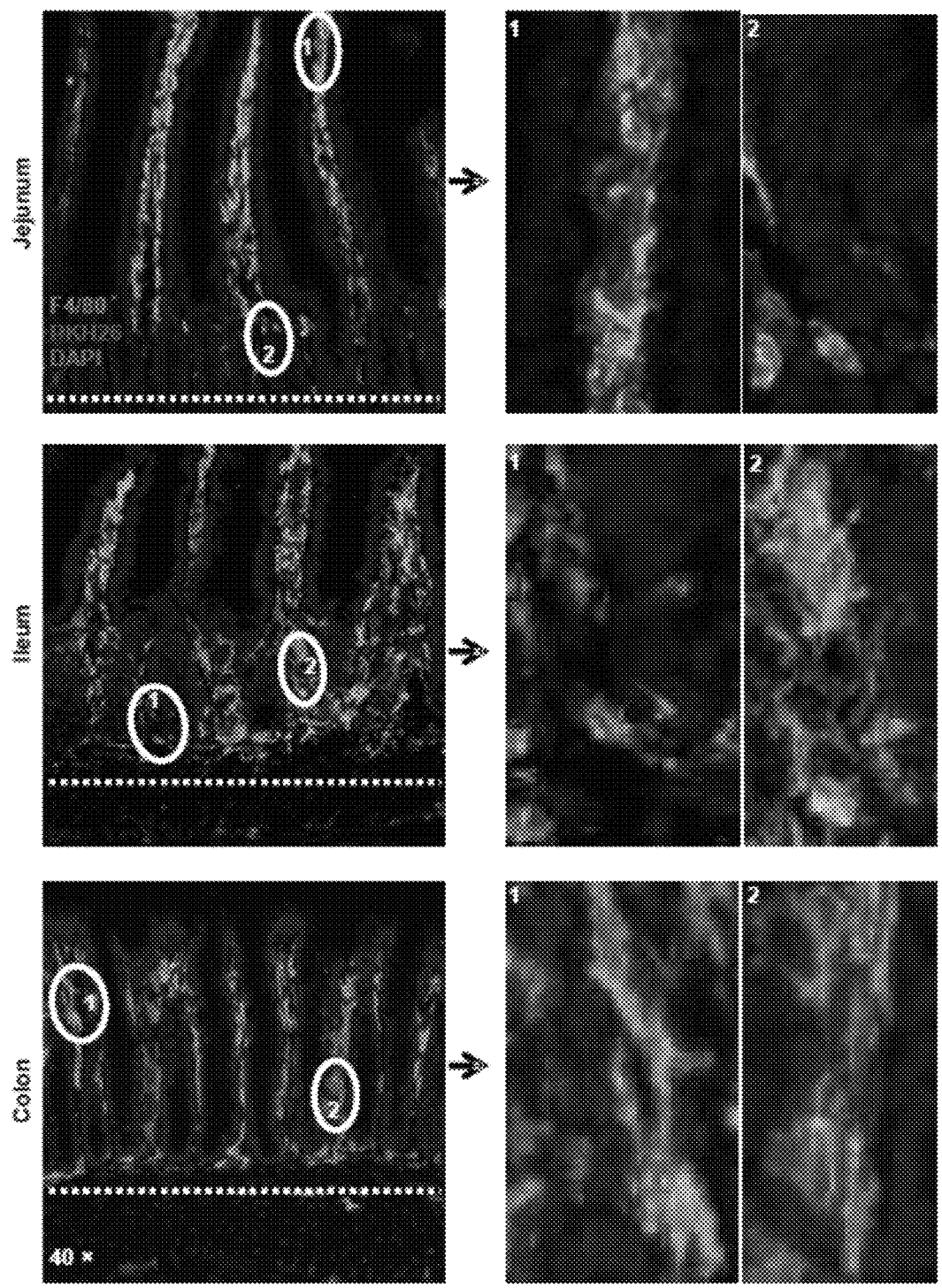
FIG. 16 includes images showing the uptake of liposomes in small and large intestines, where mice fasted overnight were orally administered two times commercially available liposome labeled with an equivalent amount of PKH26, where sections of jejunum, ileum and colon were stained with F4/80 to identify macrophages, where nuclei were labeled with DAPI, where the original magnification was 40× (left panels) with enlargement of the indicated area shown in the right panels, and where the dotted line indicates basement membrane.
Figure 17:
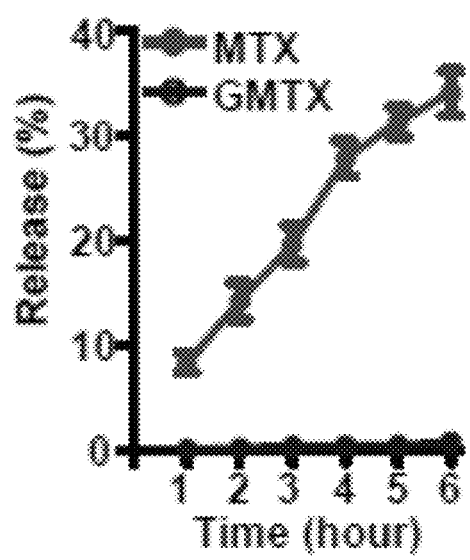
FIG. 17 is a graph showing the in vitro release curve of free MTX and GMTX in PBS at 37° C.

Example 5—Methotrexate Carried by GDNs (GMTX) Selectively Targets Lamina Propria Macrophages When comparing commercially available liposomes to GDNs, liposomes were much less efficient at transfecting intestinal macrophages after oral delivery, and uptake of liposomes by intestinal macrophages was hardly visible in both small and large intestine (FIG. 16). Since intestinal macrophages are one of the major immune cells in the intestine and targeted by GDNs, it was next determined whether GDNs can be used as an oral drug delivery vehicle. To determine their ability to be used as a vehicle, GDNs were conjugated with methotrexate (MTX), an immunosuppressant and anti-inflammatory agent. To evaluate the success of this conjugation, GMTX were first separated from free MTX through discontinued sucrose gradient centrifugation and extensive washing with PBS. The quantity of MTX in GMTX (FIG. 6A) and the stability of GMTX (FIG. 17) were measured by spectrometry analysis and the influence of conjugation on particle size and surface charge was determined using a nano zetasizer (FIG. 6B). To confirm the preservation of MTX function in GMTX, the anti-proliferation effect of GMTX was compared to free MTX. As determined by FACS analysis, GMTX showed a dose-dependent inhibition of cell proliferation similar to the effect of free MTX (FIG. 6C). Next, the cellular targeting of GMTX in vivo was observed after oral administration. As shown in FIG. 6D, orally delivered GMTX targeted to F4/80$^+$ macrophages localized in the lamina propria. Collectively, these results suggested that the conjugation of MTX to GDNs preserved the MTX function and successfully targets the majority of MTX to lamina propria macrophages.

Figure 7A:
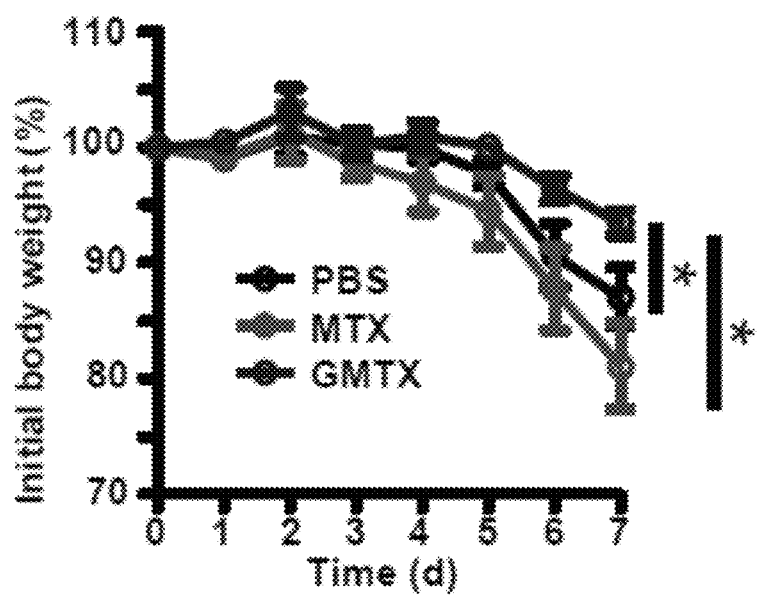
FIGS. 7A-7F include graphs and images showing the therapeutic effect of GMTX on active colitis, where the therapeutic effects of GMTX were evaluated by body weight (FIG. 7A), colon length (FIG. 7B), pathology changes (FIG. 7C), colitis score (FIG. 7D), epithelial integrity (FIG. 7E), and cytokine expression and secretion by inflamed colon (FIG. 7F).
Figure 7B:
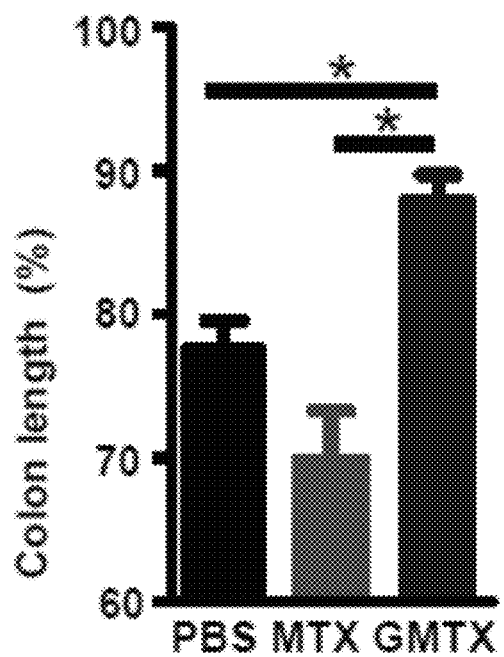
Figure 7C:
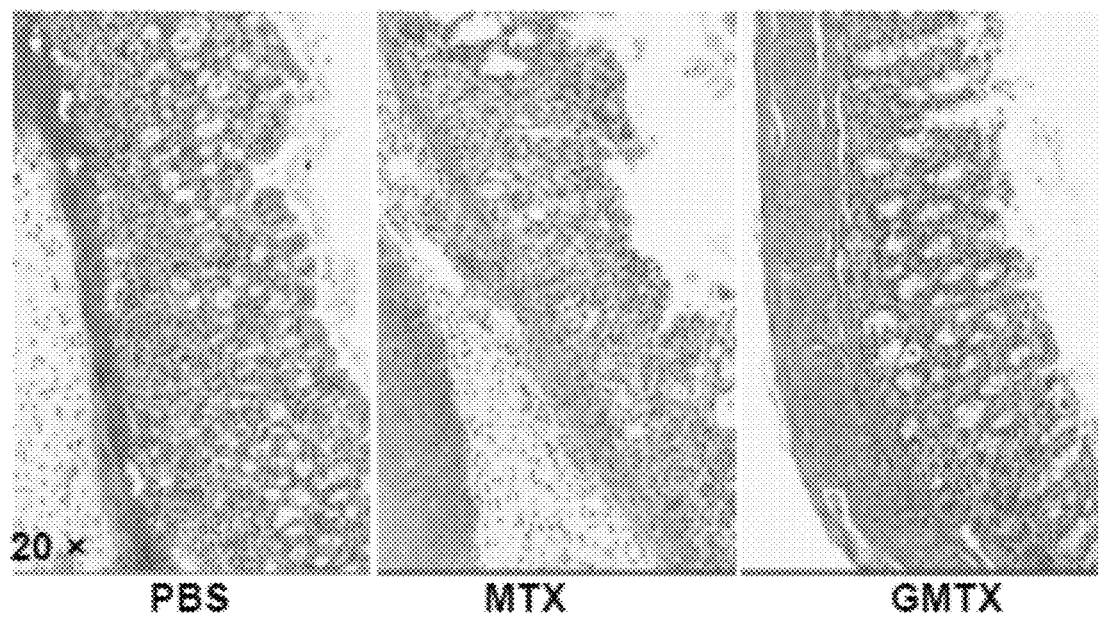
Figure 7D:
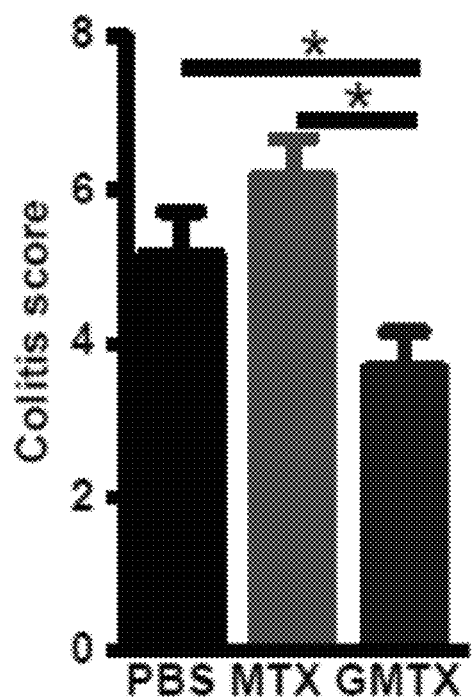
Figure 7E:
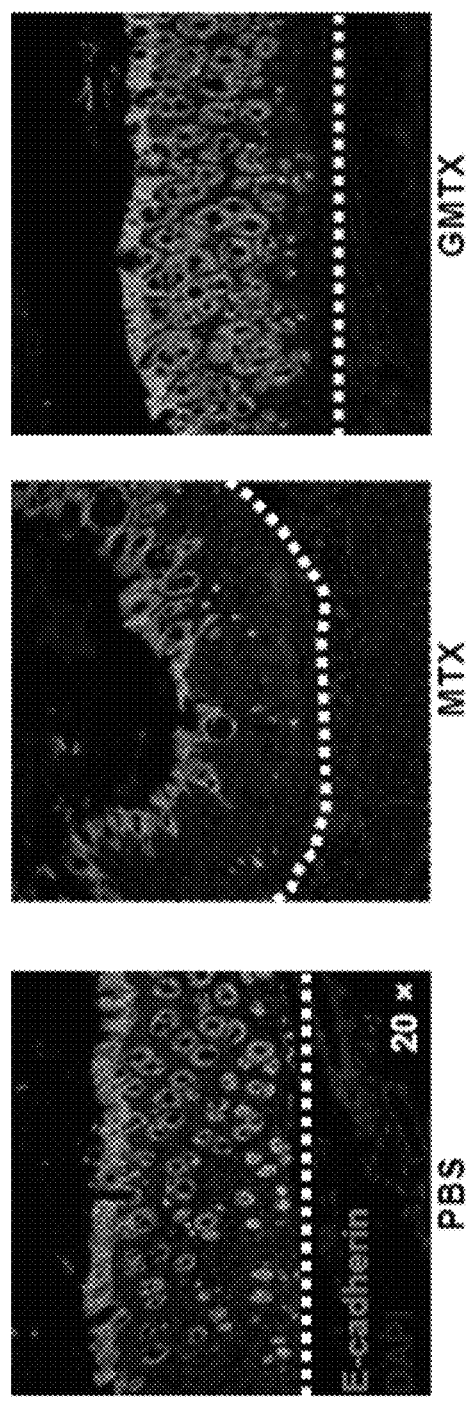
Figure 7F:
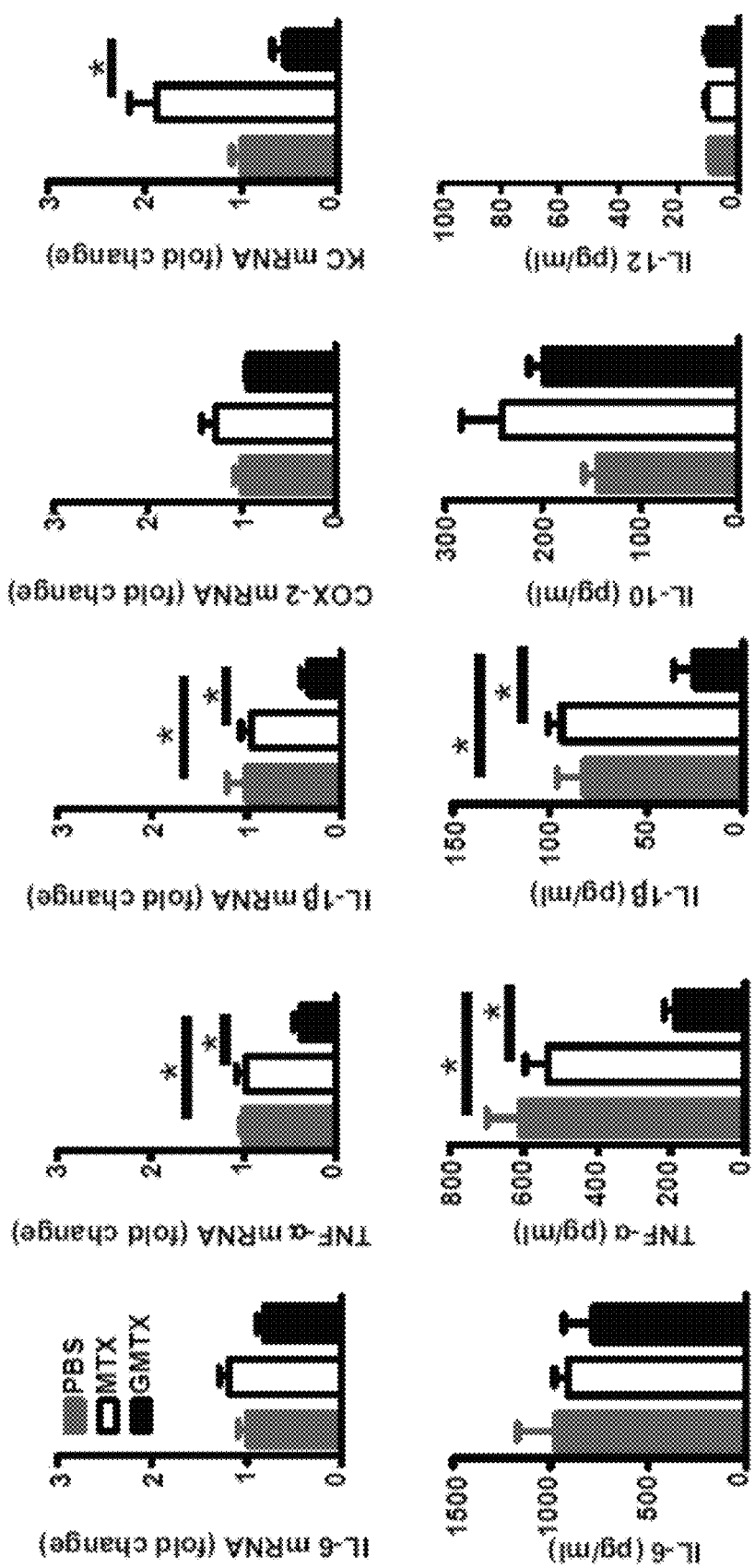

Example 6—The Therapeutic Effects of GMTX in the DSS-Induced Mouse Colitis Model The therapeutic effects of GMTX was next examined in acute colitis. Results showed that GMTX treated mice had a significant reduction in DSS-induced body weight loss and colon length shortening (FIGS. 7A-7B). These results were further supported by histological analysis. The results from H&E stained colon tissue indicated that colon tissue damage and inflammatory cell infiltration (FIGS. 7C-7D) of mice treated with GMTX were much less than those treated with free MTX or PBS. Noticeably and reproducibly, mice treated with free MTX even had aggravated symptoms of colitis in comparison with PBS treated mice in terms of the degree of colon tissue damage, colon length reduction and decreased expression of E-cadherin (FIG. 7E). The result of having a reduced inflammatory cell infiltration in the colon was consistent with a significant reduction of specific inflammatory cytokines which included TNF-α and IL-1β at the mRNA and protein level and a reduction of the expression of the neutrophil chemokine KC (FIG. 7F).

Figure 8A:
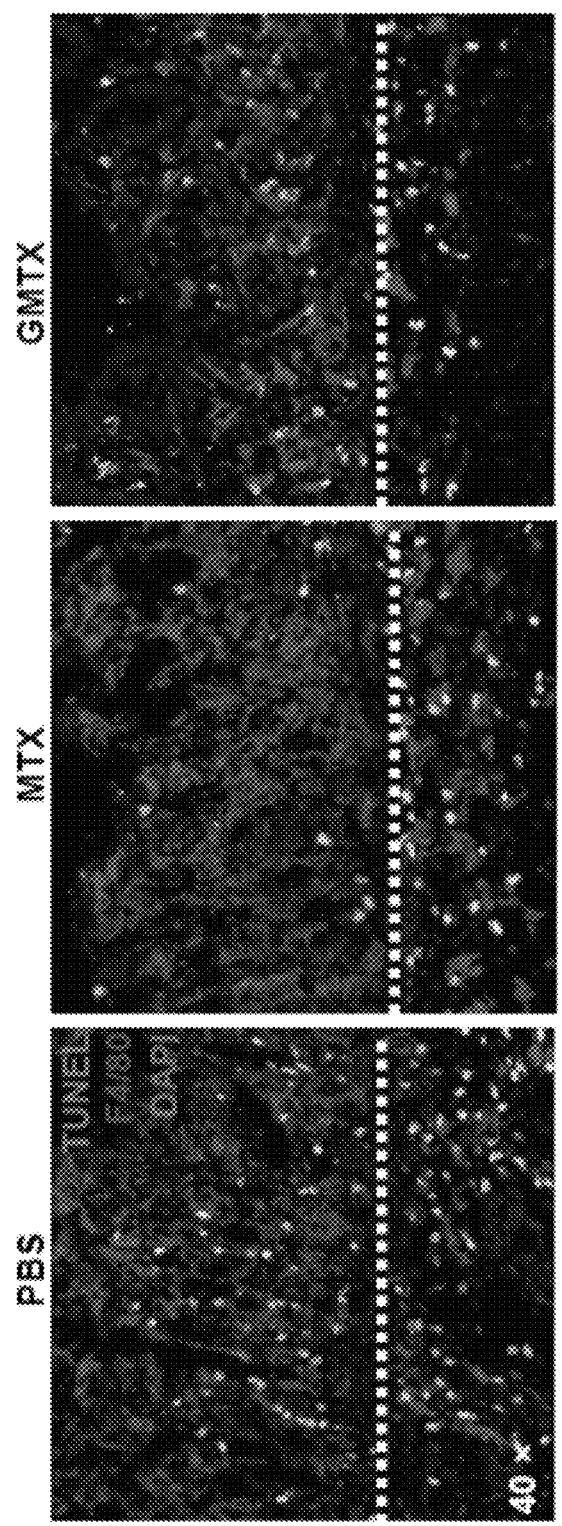
FIGS. 8A-8C include images and graphs showing the immunomodulation but not cytotoxic effect of GMTX on activated intestinal macrophages, where colitis was induced in mice with 2% DSS and then mice were given orally either PBS, MTX or GMTX on day 3, 5 and 6 of DSS treatment, including: images of colons collected on day 7 and stained with F4/80 and TUNEL (FIG. 8A); a graph showing the percentage of TUNEL$^+$ macrophages (FIG. 8B); and graphs showing the amounts of TNF-α, IL-1β, IL-6 and IL-10 as measured by ELISA in the culture supernatants of colonic macrophages that were isolated and cultured in 96-well plate for 36 h (FIG. 8C).
Figure 8B:
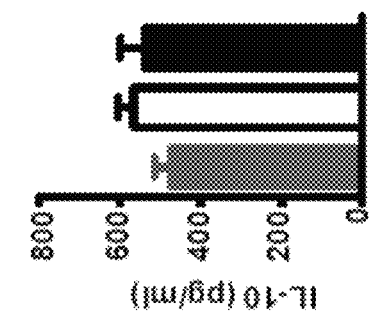
Figure 8B:
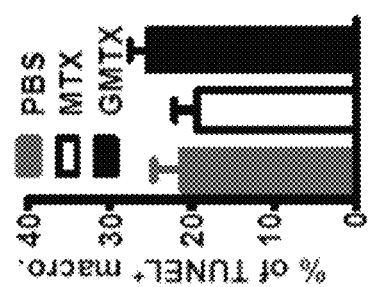
Figure 8C:
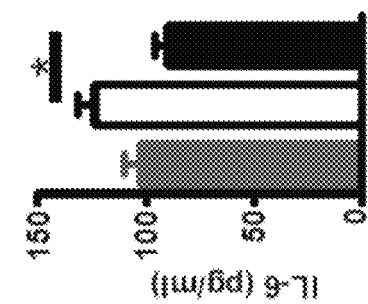
Figure 8C:
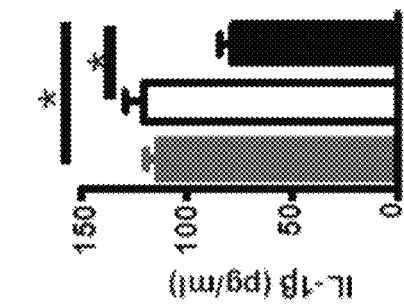
Figure 8C:
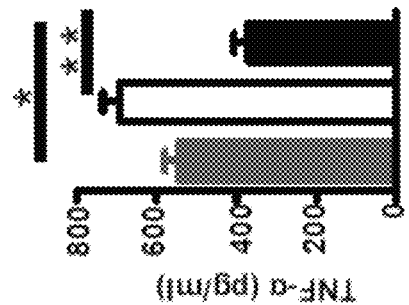

The effects of MTX on intestinal macrophages in the inflamed colon are unknown. First, the effect of MTX in the induction of apoptosis was tested on colonic macrophages. As shown in FIGS. 8A-8B, the percentage of TUNEL$^+$ macrophages did not show significant difference among treatments. Then, the effect of GMTX on colonic macrophage function was analyzed. As shown in FIG. 8C, GMTX treatment significantly reduced the production of pro-inflammatory cytokines TNF-α, IL-1β, and IL-6 by colonic macrophages. Collectively, the results suggested that GMTX treatment was superior to MTX in terms of anti-inflammatory effect with fewer side effects in the DSS mouse colitis model. These data thus demonstrated that GDNs are suitable as an oral delivery vehicle to target intestinal macrophages for treatment of intestinal inflammatory-related diseases.

Discussion of Examples 1-6

As described in the foregoing examples, nanovesicles isolated from an edible plant, i.e., grapefruit, were characterized and demonstrated to target intestinal macrophages. The results suggested that nanovesicles from beneficial grapefruit did not adversely affect intestinal immune homeostasis, but strengthened host anti-inflammatory capacity. The biological effect of grapefruit nanovesicles on macrophages was demonstrated in their protective effect in a DSS induced mouse colitis model. More significantly, the work provided insight on a grapefruit nanovesicle-based oral drug delivery vehicle for treatment of inflammation-related diseases. As proof of concept, using MTX carried by grapefruit nanovesicles (GMTX) as an example, GMTX treatment significantly enhanced the anti-inflammatory effect of MTX while MTX induced side effects were decreased remarkably in the DSS induced mouse colitis model. In addition, unlike nanovesicles synthesized artificially, oral administration of GDNs were found to cause no hepatotoxicity. Therefore, oral drug delivery by GDNs was thought to be a novel means to transport small molecule drugs to intestinal macrophages in a non-cytotoxic manner. Producing large quantities of nanovesicles from fruit was an additional advantage for accelerating the incorporation of this technology into clinical settings.

Maintaining oral tolerance to food antigens results from interaction between the intestinal immune system and food we eat daily. The results of the foregoing studies favor the hitherto unrecognized hypothesis that nanovesicles from grapefruit and perhaps other edible plants do not act as potential immune stimuli as they were thought to, but actively sustain/enhance anti-inflammatory responses against inflammatory insults by suppressing induction of inflammatory cytokines of intestinal macrophages. The unique propensity of these edible nanovesicles to enhance anti-inflammatory responses of intestinal macrophages offers attractive strategies to prevent or treat autoimmune diseases and colon cancer. Such approaches would exploit effective yet selective natural immunosuppressive mechanisms, thereby avoiding unwanted side effects caused by long term treatment with immunomodulatory drugs.

Furthermore, a GDN based delivery system could be further manipulated for achieving targeted oral delivery in general. Delivery of therapeutic agents via oral administration has many advantages over other administration routes, the most evidence being reduction of systemic exposure. Various delivery systems including nanotechnology and viral and non-viral delivery systems have been employed. Each of these approaches has advantages. However, potential toxicity, tissue specific targeting, hazardous effects on the environment and large scale economical production are challenging issues confronting these technologies. The above-described approach using edible nanovesicles has the advantage of inherent biocompatibility and biodegradability, the potential of being used as personalized oral delivery vehicles because grape exosome-like nanovesicles target intestinal stem cells and grapefruit nanovesicles target macrophages. Therefore, using edible nanovesicles as a delivery vehicle might allow personalize modulation of the function of recipient cells according to therapeutic aims.

Although the above data suggested that grapefruit GDNs are selectively taken up by intestinal macrophages and ameliorate dextran sulfate sodium (DSS) induced mouse colitis, the detailed molecular mechanism(s) responsible for the regulation of macrophage function remains to be determined. A number of potential GDN derived molecules could contribute to its anti-inflammatory response. Further analysis of the roles of GDN derived proteins (enzymes involved in lipid/carbohydrates metabolic pathways), lipids (PE and PC are dominated), and other unidentified substances, such as GDN derived glycosylated proteins in the regulation of macrophage function are challenging. Identifying those factors derived from GDNs will have potential impacts on developing preventive/therapeutic agents. For example, naringin is the most abundant flavonoid in grapefruit. The HPLC data showed that not only naringin, but also its metabolite, the functional component-naringenin, are detected in the GDNs. Another potent anti-inflammatory molecule, ω 3-serie fatty acid (22:6; ω 3-serie), might be present in the GDNs, however, our initial attempts failed to detect ω 3-serie fatty acid in GDNs.

The results from the foregoing studies indicated that the effects of GDNs could be altered by conjugation with a therapeutic agent. It was show that GDNs significantly inhibited the expression and secretion of IL-6 and IL-1α, but did not show a significant effect on TNF-α in DSS induced acute intestinal inflammation. In contrast, GMTX induced a significant suppression of the production of IL-1α and TNF-α, but did not have a significant effect on IL-6.

It is appreciated that maintaining a stable level of $PGE_2$ in the gut is important for keeping homeostasis of gut resident cells. In normal colon, $PGE_2$ is mainly derived from COX-1-expressing epithelial cells and COX-2-expressing stromal cells. The above data indicated that intestinal macrophages were the major targets of orally given GDNs. Therefore, a lack of significant change in the level of gut $PGE_2$ due to GDNs treatment was expected. During inflammation, although COX-2 mRNA is induced, the induction of $PGE_2$ regulated by COX-2 would be expected. However, levels of $PGE_2$ are regulated by the local balance between the COX-2-driven synthesis and 15-hydroxyprostaglandin dehydrogenase (15-PGDH)-mediated degradation of $PGE_2$. GDN treatment may affect both enzymes' activity as well as multiple factors that affect the stability of $PGE_2$ in the colon tissue.

From the foregoing studies, it was also found that GDNs were very heterogenic in size; it was speculated that the effect of each subpopulation of GDNs on macrophages may be different. In addition, some subpopulations of GDNs may be taken up through the endocytosis pathway; and others through micro/macro-pinocytosis. Blocking one pathway may lead to an alteration of the expression profiles of GDN targeted macrophages which could contribute to one subset population of GDNs or the same size GDNs being packed with different functional molecules. Demonstration of either assumption has to wait for the technology that allows separating the subsets of nanovesicles based on the size of GDNs, followed by mass spectrometer analysis.

The heterogeneity in size of GDNs is also affected by pH value. Under acid conditions like those found in the stomach, it was observed that the heterogeneity in size of GDNs decreased. A number of reasons may lead to the reduction of heterogeneity. One of them could be the increasing the affinity of interaction between certain GDN proteins or lipids or carbohydrates.

Throughout this document, various references are mentioned. All such references are incorporated herein by reference, including the references set forth in the following list:

REFERENCES

1. Powell, J J, Faria, N, Thomas-McKay, E, and Pele, L C (2010). Origin and fate of dietary nanoparticles and microparticles in the gastrointestinal tract. J Autoimmun 34: J226-233.
2. Powell, J J, Thoree, V, and Pele, L C (2007). Dietary microparticles and their impact on tolerance and immune responsiveness of the gastrointestinal tract. Br J Nutr 98 Suppl 1: S59-63.
3. Schneider, JC (2007). Can microparticles contribute to inflammatory bowel disease: innocuous or inflammatory? Exp Biol Med (Maywood) 232: 1-2.
4. Setser, C S, and Racette, WL (1992). Macromolecule replacers in food products. Crit Rev Food Sci Nutr 32: 275-297.
5. Badens, E, Magnan, C, and Charbit, G (2001). Microparticles of soy lecithin formed by supercritical processes. Biotechnology and Bioengineering 72: 194-204.
6. Bauer, C, et al. (2010). Colitis induced in mice with dextran sulfate sodium (DSS) is mediated by the NLRP3 inflammasome. Gut 59: 1192-1199.
7. Wang, Q, et al. (2013). Delivery of therapeutic agents by nanoparticles made of grapefruit-derived lipids. Nat Commun 4.
8. Ju, S, et al. (2013). Grape Exosome-like Nanoparticles Induce Intestinal Stem Cells and Protect Mice From DSS-Induced Colitis. Mol Ther 21: 1345-1357.
9. Cho, J Y, Chi, S-G, and Chun, H S (2011). Oral administration of docosahexaenoic acid attenuates colitis induced by dextran sulfate sodium in mice. Molecular Nutrition & Food Research 55: 239-246.
10. Stremmel, W, Merle, U, Zahn, A, Autschbach, F, Hinz, U, and Ehehalt, R (2005). Retarded release phosphatidylcholine benefits patients with chronic active ulcerative colitis. Gut 54: 966-971.
11. Inês Amaro, M, et al. (2009). Anti-inflammatory activity of naringin and the biosynthesised naringenin by naringinase immobilized in microstructured materials in a model of DSS-induced colitis in mice. Food Research International 42: 1010-1017.
12. Dou, W, et al. (2013). Protective effect of naringenin against experimental colitis via suppression of Toll-like receptor 4/NF-κB signalling. British Journal of Nutrition FirstView: 1-10.
13. Yan, F, et al. (2011). Colon-specific delivery of a probiotic-derived soluble protein ameliorates intestinal inflammation in mice through an EGFR-dependent mechanism. The Journal of Clinical Investigation 121: 2242-2253.
14. Liu, C, et al. (2006). Murine Mammary Carcinoma Exosomes Promote Tumor Growth by Suppression of NK Cell Function. The Journal of Immunology 176: 1375-1385.
15. Laulagnier, K, et al. (2004). Mast cell- and dendritic cell-derived exosomes display a specific lipid composition and an unusual membrane organization. Biochem J 380: 161-171.
16. Ju, S, et al. (2013). Grape Exosome-like Nanoparticles Induce Intestinal Stem Cells and Protect Mice From DSS-Induced Colitis. Mol Ther.
17. Morteau, O, et al. (2000). Impaired mucosal defense to acute colonic injury in mice lacking cyclooxygenase-1 or cyclooxygenase-2. The Journal of Clinical Investigation 105: 469-478.
18. Conner, S D, and Schmid, S L (2003). Regulated portals of entry into the cell. Nature 422: 37-44.
19. Ghigo, E, et al. (2008). Ameobal Pathogen Mimivirus Infects Macrophages through Phagocytosis. PLoS Pathog 4: e1000087.
20. Pollock, S, et al. (2010). Uptake and trafficking of liposomes to the endoplasmic reticulum. The FASEB Journal 24: 1866-1878.
21. Lee, T-S, and Chau, L-Y (2002). Heme oxygenase-1 mediates the anti-inflammatory effect of interleukin-10 in mice. Nat Med 8: 240-246.
22. Sheikh, S Z, et al. (2011). An Anti-Inflammatory Role for Carbon Monoxide and Heme Oxygenase-1 in Chronic Th2-Mediated Murine Colitis. The Journal of Immunology 186: 5506-5513.
23. Taheri, A, et al. (2011). Nanoparticles of Conjugated Methotrexate-Human Serum Albumin: Preparation and Cytotoxicity Evaluations. Journal of Nanomaterials 2011.
24. Majumdar, S, and Aggarwal, B B (2001). Methotrexate Suppresses NF-κB Activation Through Inhibition of IκBα Phosphorylation and Degradation. The Journal of Immunology 167: 2911-2920.
25. Desai, N (2012). Challenges in Development of Nanoparticle-Based Therapeutics. AAPS J 14: 282-295.
26. Pabst, O, and Mowat, A M (2012). Oral tolerance to food protein. Mucosal Immunol 5: 232-239.
27. Yamanaka, Y J, and Leong, KW (2008). Engineering strategies to enhance nanoparticle-mediated oral delivery. Journal of Biomaterials Science—Polymer Edition 19: 1549-1570.
28. Wilson, D S, Dalmasso, G, Wang, L, Sitaraman, S V, Merlin, D, and Murthy, N (2010). Orally delivered thioketal nanoparticles loaded with TNF-α-siRNA target inflammation and inhibit gene expression in the intestines. Nat Mater 9: 923-928.
29. Friend, D R (2005). New oral delivery systems for treatment of inflammatory bowel disease. Advanced Drug Delivery Reviews 57: 247-265.
30. Jourdan, P S, McIntosh, C A, and Mansell, R L (1985). Naringin Levels in Citrus Tissues: II. Quantitative Distribution of Naringin in *Citrus paradisi* MacFad. Plant Physiol 77: 903-908.
31. Newberry, R D, Stenson, W F, and Lorenz, RG (1999). Cyclooxygenase-2-dependent arachidonic acid metabolites are essential modulators of the intestinal immune response to dietary antigen. Nat Med 5: 900-906.
32. Newberry, R D, McDonough, J S, Stenson, W F, and Lorenz, RG (2001). Spontaneous and Continuous Cyclooxygenase-2-Dependent Prostaglandin E2 Production by Stromal Cells in the Murine Small Intestine Lamina Propria: Directing the Tone of the Intestinal Immune Response. The Journal of Immunology 166: 4465-4472.
33. Tai, H-H, Ensor, C M, Tong, M, Zhou, H, and Yan, F (2002). Prostaglandin catabolizing enzymes. Prostaglandins & Other Lipid Mediators 68-69: 483-493.
34. Sun, D, et al. (2010). A Novel Nanoparticle Drug Delivery System: The Anti-inflammatory Activity of Curcumin Is Enhanced When Encapsulated in Exosomes. Mol Ther 18: 1606-1614.

35. Deng, Z B, et al. (2012). Intestinal mucus-derived nanoparticles mediate activation of Wnt/beta-catenin signaling plays a role in induction of liver NKT cell anergy. Hepatology.
36. Bligh, E G, and Dyer, W J (1959). A rapid method of total lipid extraction and purification. Can J Biochem Physiol 37: 911-917.
37. Wanjie, S W, Welti, R, Moreau, R A, and Chapman, K D (2005). Identification and quantification of glycerolipids in cotton fibers: reconciliation with metabolic pathway predictions from DNA databases. Lipids 40: 773-785.
38. Li, X-H, Xiong, Z-L, Lu, S, Zhang, Y, and Li, F-M (2010). Pharmacokinetics of Naringin and its Metabolite Naringenin in Rats after Oral Administration of Rhizoma Drynariae Extract Assayed by UPLC-MS/MS. Chinese Journal of Natural Medicines 8: 40-46.
39. Ribeiro, I A, and Ribeiro, M H L (2008). Naringin and naringenin determination and control in grapefruit juice by a validated HPLC method. Food Control 19: 432-438.
40. Hermida L G, S-XM, Barnadas-Rodriguez R. (2009). Combined strategies for liposome characterization during in vitro digestion. Journal of Liposome Research 19: 207-219.
41. Majoros, I J, Thomas, T P, Mehta, C B, and Baker, J R (2005). Poly(amidoamine) Dendrimer-Based Multifunctional Engineered Nanodevice for Cancer Therapy. Journal of Medicinal Chemistry 48: 5892-5899.
42. Vaishnava, S, et al. (2011). The Antibacterial Lectin RegIIIγ Promotes the Spatial Segregation of Microbiota and Host in the Intestine. Science 334: 255-258.
43. Katz, J P, et al. (2002). The zinc-finger transcription factor Klf4 is required for terminal differentiation of goblet cells in the colon. Development 129: 2619-2628.
44. Fuhrer, A, Sprenger, N, Kurakevich, E, Borsig, L, Chassard, C, and Hennet, T (2010). Milk sialyllactose influences colitis in mice through selective intestinal bacterial colonization. The Journal of Experimental Medicine 207: 2843-2854.
45. Denning, T L, Wang, Y-c, Patel, SR, Williams, I R, and Pulendran, B (2007). Lamina propria macrophages and dendritic cells differentially induce regulatory and interleukin 17-producing T cell responses. Nat Immunol 8: 1086-1094.
46. Ismail, A S, et al. (2011). γδ intraepithelial lymphocytes are essential mediators of host-microbial homeostasis at the intestinal mucosal surface. Proceedings of the National Academy of Sciences 108: 8743-8748.
47. Wang, Y, et al. (2010). Lymphotoxin Beta Receptor Signaling in Intestinal Epithelial Cells Orchestrates Innate Immune Responses against Mucosal Bacterial Infection. Immunity 32: 403-413.
48. Allen, I C, et al. (2010). The NLRP3 inflammasome functions as a negative regulator of tumorigenesis during colitis-associated cancer. The Journal of Experimental Medicine 207: 1045-1056.
49. Riehl, T E, et al. (2006). Azoxymethane protects intestinal stem cells and reduces crypt epithelial mitosis through a COX-1-dependent mechanism. American Journal of Physiology—Gastrointestinal and Liver Physiology 291: G1062-G1070.
50. Kamada, N, et al. (2005). Abnormally Differentiated Subsets of Intestinal Macrophage Play a Key Role in Th1-Dominant Chronic Colitis through Excess Production of IL-12 and IL-23 in Response to Bacteria. The Journal of Immunology 175: 6900-6908
51. X. Xiang, A. Poliakov, C. Liu, Y. Liu, Z. B. Deng, J. Wang, Z. Cheng, S. V. Shah, G. J. Wang, L. Zhang, W. E. Grizzle, J. Mobley, H. G. Zhang, Induction of myeloid-derived suppressor cells by tumor exosomes. International journal of cancer. Journal international du cancer 124, 2621-2633 (2009).
52. Wang B, Zhuang X, Deng Z B, Jiang H, Mu J, Wang Q, Xiang X, Guo H, Zhang L, Dryden G, Yan J, Miller D, Zhang H G (2014). Targeted drug delivery to intestinal macrophages by bioactive nanovesicles released from grapefruit. Mol Ther. 22(3):522-34.

It will be understood that various details of the presently-disclosed subject matter can be changed without departing from the scope of the subject matter disclosed herein. Furthermore, the foregoing description is for the purpose of illustration only, and not for the purpose of limitation.

What is claimed is:

1. A composition, comprising:
   a microvesicle derived from an edible plant; and
   a therapeutic agent conjugated to the microvesicle, the therapeutic agent chemically-linked to a plasma membrane of the microvesicle with a cross-linking agent,
   wherein the therapeutic agent is a phytochemical agent selected from curcumin, resveratrol, baicalein, equol, fisetin, and quercetin, and
   wherein the cross-linking agent is selected from the group consisting of N-ethylcarbodiimide (EDC), dicyclohexyl carbodiimide (DCC), homobifunctional disuccinimidyl, disuccinimidyl tartrate, 3-3'-dithiobis-propionimidate (DTBP), and ethylene glycol bis-succinimidyl succinate (EGS).

2. The composition of claim 1, wherein the edible plant is a fruit or a vegetable.

3. The composition of claim 1, wherein the edible plant is selected from a grape, a grapefruit, a tomato, a ginger, a carrot, a broccoli, a cabbage, a lettuce, a blackberry, a cauliflower, and a spinach.

4. A pharmaceutical composition, comprising a composition according to claim 1 and a pharmaceutically-acceptable vehicle, carrier, or excipient.

5. A method for treating an inflammatory disorder, comprising administering to a subject in need thereof an effective amount of a composition of claim 1.

6. The method of claim 5, wherein the inflammatory disorder is selected from the group consisting of sepsis, septic shock, colitis, inflammation-promoted cancer, and arthritis.

7. The method of claim 5, wherein the inflammatory disorder is inflammation-promoted cancer, and wherein the inflammation-promoted cancer is colon cancer.

8. The method of claim 5, wherein the composition is administered orally or intranasally.

9. The method of claim 5, wherein administering the composition reduces an amount of an inflammatory cytokine in a subject.

10. The method of claim 9, wherein the inflammatory cytokine is selected from the group consisting of tumor necrosis factor-α, interleukin-1β, and interleukin-6.

11. The method of claim 5, wherein the edible plant is a fruit or a vegetable.

12. The method of claim 5, wherein the edible plant is selected from a grape, a grapefruit, a tomato, a ginger, a carrot, a broccoli, a cabbage, a lettuce, a blackberry, a cauliflower, and a spinach.

13. The method of claim 5, wherein the inflammatory disorder is colitis.

14. A method for treating a cancer, comprising administering to a subject in need thereof an effective amount of a composition of claim 1.

* * * * *